US012485299B2

(12) United States Patent
Song et al.

(10) Patent No.: US 12,485,299 B2
(45) Date of Patent: Dec. 2, 2025

(54) ANTIBODY-IMMUNE AGONIST CONJUGATE AND APPLICATIONS THEREOF

(71) Applicant: GENEQUANTUM HEALTHCARE (SUZHOU) CO., LTD., Suzhou (CN)

(72) Inventors: Paul H. Song, Suzhou (CN); Gang Qin, Suzhou (CN); Chong Liu, Suzhou (CN)

(73) Assignee: GENEQUANTUM HEALTHCARE (SUZHOU) CO., LTD., Suzhou (CN)

( * ) Notice: Subject to any disclaimer, the term of this patent is extended or adjusted under 35 U.S.C. 154(b) by 168 days.

(21) Appl. No.: 18/366,028

(22) Filed: Aug. 7, 2023

(65) Prior Publication Data

US 2023/0372511 A1 Nov. 23, 2023

Related U.S. Application Data

(62) Division of application No. 17/689,198, filed on Mar. 8, 2022, now Pat. No. 11,717,576.

(30) Foreign Application Priority Data

Mar. 8, 2021 (WO) ................ PCT/CN2021/079609

(51) Int. Cl.
*A61K 47/68* (2017.01)
*A61P 35/00* (2006.01)

(52) U.S. Cl.
CPC ...... *A61K 47/6851* (2017.08); *A61K 47/6803* (2017.08); *A61K 47/6849* (2017.08); *A61P 35/00* (2018.01)

(58) Field of Classification Search
None
See application file for complete search history.

(56) References Cited

U.S. PATENT DOCUMENTS

| | | | | |
|---|---|---|---|---|
| 5,229,490 | A | 7/1993 | Tam | |
| 9,872,923 | B2 | 1/2018 | Grawunder et al. | |
| 10,030,066 | B2 | 7/2018 | Jin et al. | |
| 11,717,576 | B2 | 8/2023 | Song et al. | |
| 2009/0169547 | A1 * | 7/2009 | Sahin ...................... | A61P 35/04 424/139.1 |
| 2010/0129314 | A1 | 5/2010 | Singh et al. | |
| 2011/0014216 | A1 | 1/2011 | Brecht et al. | |
| 2013/0309256 | A1 | 11/2013 | Lyon et al. | |

(Continued)

FOREIGN PATENT DOCUMENTS

| | | |
|---|---|---|
| CN | 102973947 | 3/2007 |
| CN | 1938046 | 3/2013 |

(Continued)

OTHER PUBLICATIONS

Herceptin® [trastuzumab], FDA product label insert 2010 (Year: 2010).*

(Continued)

*Primary Examiner* — Karl J Puttlitz
(74) *Attorney, Agent, or Firm* — Hoxie & Associates LLC

(57) ABSTRACT

The present disclosure relates to a linking unit molecule for targeting molecule-drug conjugate, and the corresponding conjugate, the preparation and use thereof, and in particular relates to an antibody-immune agonist conjugate (AIAC) as a novel type of cancer therapy.

21 Claims, 20 Drawing Sheets

Specification includes a Sequence Listing.

(56) References Cited

U.S. PATENT DOCUMENTS

| | | | |
|---|---|---|---|
| 2016/0193355 A1 | 7/2016 | Qin et al. | |
| 2017/0112944 A1 | 4/2017 | Qin et al. | |
| 2022/0185881 A1 | 6/2022 | Yang et al. | |
| 2022/0378930 A1 | 12/2022 | Song et al. | |
| 2024/0181072 A1 | 6/2024 | Song et al. | |

FOREIGN PATENT DOCUMENTS

| | | | |
|---|---|---|---|
| JP | S595150 | 1/1984 | |
| JP | 2006-514081 | 4/2006 | |
| WO | WO 2007/028639 | 3/2007 | |
| WO | WO 2012/142659 | 10/2012 | |
| WO | WO 2013/003555 | 1/2013 | |
| WO | WO 2014/055877 | 4/2014 | |
| WO | WO 2014/056333 | 4/2014 | |
| WO | WO 2018/170179 | 9/2018 | |
| WO | 2020/016662 A2 | 1/2020 | |
| WO | 2020/200196 A1 | 10/2020 | |
| WO | WO 2021/136475 | 7/2021 | |
| WO | WO 2021/136483 | 7/2021 | |
| WO | WO-2021136483 A1 * | 7/2021 | ......... A61K 47/6803 |
| WO | WO 2022/188743 | 9/2022 | |

OTHER PUBLICATIONS

Alley et al., "Contribution of Linker Stability to the Activities of Anticancer Immunoconjugates," Bioconjug Chem., vol. 19, No. 3, pp. 759-765, (2008); DOI: 10.1021/bc7004329; Abstract Only—1 page.

Bauer et al. "Clickable Tyrosine Binding Bifunctional Linkers for Preparation of DNA-Protein Conjugates" Bioconjugate Chemistry, vol. 24, No. 6, Jun. 9, 2013, pp. 1094-1101.

Bentley, et al., "Mutagenesis Studies of Substrate Recognition and Catalysis in the Sortase A Transpeptidase from *Staphylococcus aureus*," The Journal of Biological Chemistry, vol. 283, No. 21, pp. 14762-14771, (2008).

Blaustein, Robert O., "Kinetics of Tethering Quaternary Ammonium Compounds to K+ Channels," The Journal of General Physiology, vol. 120, pp. 203-216, (2002).

Chudasama et al., "Semi-Mechanistic Population Pharmacokinetic Model of Multivalent Trastuzumab Emtansine in Patients with Metastatic Breast Cancer," Clinical Pharmacology & Therapeutics, vol. 92, No. 4, pp. 520-527, (2012); DOI: 10.1038/clpt.2012.153; Abstract Only—2 pages.

Extended European Search Report, EP 15786402.6 dated Nov. 10, 2017.

Guo, et al., "New Method for Site-Specific Modification of Liposomes with Proteins Using Sortase A-Mediated Transpeptidation," Bioconjugate Chemistry, vol. 23, No. 3, pp. 650-655, (2012).

Gupta, et al., "A Bioorthogonal Chemoenzymatic Strategy for Defined Protein Dendrimer Assembly," ChemBioChem, vol. 13, No. 17, 2489-2494, (2012).

Handl, et al., "Hitting multiple targets with multimeric ligands," Expert Opin. Ther. Targets, vol. 8, No. 6, (2004).

International Search Report issued in International Application No. PCT/CN2014/076414, mailed Jul. 18, 2014, 1 page.

International Search Report PCT/CN2015/077887 Dated Aug. 28, 2015.

Jiang, et al., "End-Point Immobilization of Recombinant Thrombomodulin via Sortase-Mediated Ligation," Bioconjug Chem., vol. 23, No. 3, pp. 643-649, (2012).

JP 2016-563404 Office Action dated Feb. 5, 2019.

Kornberger et al. ("Kornberger", mAbs. 2014, 2, 354-366, published online Dec. 9, 2013). (2013).

Leung, et al., "Alkyne-Aldehyde Reductive C—C Coupling through Ruthenium-Catalyzed Transfer Hydrogenation: Direct Regio- and Stereoselective Carbonyl Vinylation to Form Trisubstituted Allylic Alcohols in the Absence of Premetallated Reagents," Chemistry, vol. 17, No. 44, pp. 1-15, (2011).

Lyon et al., "Self-Hydrolyzing Maleimides Improve the Stability and Pharmacological Properties of Antibody-Drug Conjugates," Nat Biotechnol., vol. 32, No. 10, pp. 1059-1062, (2014); DOI: 10.1038/nbt.2968; Abstract Only—1 page.

Madej et al.. "Engineering of an anti-epidermal growth factor receptor antibody to single chain format and labeling by Sortase A-mediated protein ligation" Biotechnology and Bioengineering, vol. 109, No. 6, Jun. 1, 2012, pp. 1461-1470.

Mao, et al., "Sortase-Mediated Protein Ligation: A New Method for Protein Engineering," J. Am. Chem. Soc., vol. 126, pp. 2670-2671, (2004).

Mattson, et al., "A practical approach to crosslinking," Molecular Biology Reports, vol. 17, pp. 167-183, (1993).

Nair, et al., "The Thiol-Michael Addition Click Reaction: A Powerful and Widely Used Tool in Materials Chemistry," American Chemical Society, vol. 26, pp. 724-744, (2014).

Nelson, et al., "A Biosynthetic Strategy for Re-engineering the *Staphylococcus aureus* Cell Wall with Non-native Small Molecules," ACS Chemical Biology, vol. 5, No. 12, pp. 1147-1155, (2010).

Parthasarathy et al., "Sortase A as a Novel Malecular "Stapler" for Sequence-Specific Protein Conjugation," Bioconjugate Chem., vol. 18, pp. 469-476, (2007).

Ponte et al., "Understanding How the Stability of the Thiol-Maleimide Linkage Impacts the Pharmacokinetics t>f Lysine-Linked Antibody-Mayansinoin Conjugates", Bioconjugate Chemistry, vol. 27, No. 7, Jul. 20, 2016, pp. 1588-1598.

Popp, et al., "Sortagging: a versatile method for protein labeling," Nature Chemical Biology, vol. 3, No. 11, pp. 707-708, (2007).

Pritz, et al., "Synthesis of Protein Mimics with Nonlinear Backbone Topology by a Combined Recombinant, Enzymatic, and Chemical Synthesis Strategy," Angewandte Chemie, International Edition, vol. 47, No. 10, pp. 3642-3645, (2008).

Registry (STM) [online], (Search Date: Dec. 18, 2017) CAS No. 125739-96-0, (1990); 1 page.

Sastry, et al., "Amino acid sequence of pilin isolated from Pseudomonas aeruginosa PAK," Federation of European Biochemical Societies, vol. 151, No. 2, pp. 253-256, (1983).

Sequence ID WP_010081207.1, full sequence, 2 pages, May 24, 2013 (CSP).

Shen et al. "Conjugation site modulates the in vivo stability and therapeutic activity of antibody-drug conjugates" Nature Biotechnology, vol. 3, No. 2, Jan. 22, 2012, pp. 184-189.

Swee, et al., "Sortase-mediated modification of αDEC2 affords optimization of antigen presentation and immunization against a set of viral epitopes," PNAS, vol. 110, No. 4, pp. 1428-1433, (2013).

Ta, et al., "Enzymatic Antibody Tagging: Toward a Universal Biocompatible Targeting Tool," TCM, vol. 22, No. 4, pp. 105-111, (2012).

Tanaka, et al., "Site-Specific Protein Modification on Living Cells Catalyzed by Sortase," ChemBioChem, vol. 9, No. 5, pp. 802-807, (2008).

Thomas, et al., "Application of a Trifunctional Reactive Linker for the Construction of Antibody-Drug Hybrid Conjugates," Bioorg. Med. Chem. Lett., vol. 18, No. 21, pp. 5785-5788, (2008).

Tsukiji, et al., "Sortase-Mediated Ligation: A Gift from Gram-Positive Bacteria to Protein Engineering," ChemBioChem, vol. 10, pp. 787-798, (2009).

Tumey et al. "Mild Method for Succinimide Hydrolysis on ADCs: Impact on ADC Potency, Stability, Exposure and Efficacy," Bioconjugate Chem, 2014, 25, 1871-1880 (2014).

* cited by examiner

LU102

LU105

LU106

LU107

LU108

LU109

LU110

ANTIBODY-IMMUNE AGONIST CONJUGATE AND APPLICATIONS THEREOF

CROSS-REFERENCE TO RELATED APPLICATIONS

This application is a divisional of U.S. patent application Ser. No. 17/689,198 filed on Mar. 8, 2022, which is a U.S. Non-Provisional Application under 35 U.S.C. § 111(a), which claims priority to and the benefit of International Application No. PCT/CN2021/079609 filed on Mar. 8, 2021, the contents of each of which are hereby incorporated by reference in their entirety.

REFERENCE TO A SEQUENCE LISTING

The contents of the electronic sequence listing (2023-08-06-GQH-09-USD-SequenceListingST26.xml; Size: 47,932 bytes; and Date of Creation: Aug. 6, 2023) is incorporated herein by reference.

TECHNICAL FIELD

The present disclosure relates to the biopharmaceutical field, particularly to a linking unit for targeting molecule-immune agonist conjugate, and the corresponding conjugate, the preparing process and use thereof.

BACKGROUND

In the developmental and clinical circumstances, targeted delivery of therapeutic agents remains a great challenge for cancer therapies. The present targeting molecule-drug conjugates that are approved by FDA are mainly antibody-drug conjugates (ADCs) wherein the drug (warhead) is usually a small molecule cytotoxin.

Immunotherapy is a new modality of cancer therapy that has shown great power. While immune checkpoint blockage represented by CLTA-4 and PD-1/L1 monoclonal antibody, which are basically T cell-based therapy, was approved for various cancer indications, there are also a lot of efforts exploring other mechanisms of immune system to fight against cancer. Targeting myeloid cells, majorly macrophages, DCs, has emerged as a promising direction. Activating macrophages and DCs by agonists or by macrophage checkpoint inhibitors enhances not only their capacity of phagocytosis to clear tumor cells, but also their functions of antigen presentation, which would more robustly ignite adaptive anti-tumor immunity.

TLR7/8 are two important pattern recognition receptors that are located in the endosomal membrane of macrophages, DCs, and monocytes. They naturally sense the ssRNAs derived from virus, mediate the activation of immune cells and release of pro-inflammation cytokines. A lot of researches have demonstrated that TLR7/8 agonists have anti-tumor activity. Imiquimod, a TLR7 agonist, has been approved for the treatment of genital warts, superficial basal cell carcinoma, and actinic keratosis by topical administration. Resiquimod, a TLR7/8 dual agonist, has been approved for the treatment of cutaneous T cell lymphoma. Nevertheless, the side effects induced by systemic administration of TLR7/8 agonist restricted their usage in broader spectrum of cancers.

The present invention provides an antibody-immune agonist conjugate (AIAC), a novel type of tumor targeting therapy.

SUMMARY

In one aspect, provide is a compound of formula (I):

(I)

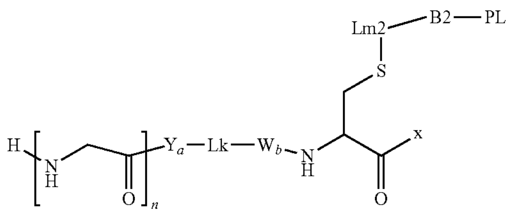

wherein n is an integer of 3 to 10;

Lm2 is

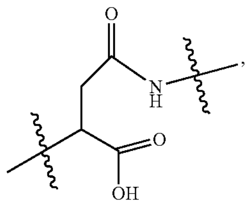,
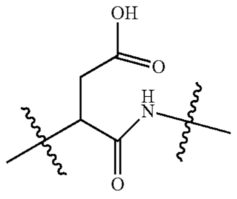

or a mixture thereof;

x is selected from hydrogen, OH, $NH_2$, an amino acid fragment comprising 1-10 amino acids, a nucleotide fragment comprising 1-10 nucleotides;

Lk is a combination of $L_1$-$L_2$-$L_3$;

$L_1$ and $L_3$ are each independently selected from: —$CH_2$—, —NH—, —C(O)—, —NHC(O)—, —C(O)NH—; and combination of a $C_{1-4}$ alkylene with one of the following groups: —$CH_2$—, —NH—, —C(O)—, —NHC(O)—, —C(O)NH—;

$L_2$ is absent or is a $C_{7-34}$ alkylene, and wherein one or more (—$CH_2$—) structures in the alkylene is optionally replaced by —O—;

Y and W are each independently absent, PABC or selected from a spacer comprising 1-10, preferably 1-6, more preferably 1-4 amino acids;

B2 is selected from the following group or their combination: —$(CH_2)_k$C(O)—, —$(CH_2)_k$C(O)-Val-Cit-PABC—, —$(CH_2)_k$C(O)-Val-Cit-PABC—(NH—$CR^1R^2$—C(O))$_d$—, —$(CH_2)_{k1}$C(O)—NH—$(C_2H_4$—O)$_j$—$(CH_2)_{k2}$C(O)-Lys-, —$(CH_2)_k$C(O)—NH—$(C_2H_4$—O)$_j$—, —$(CH_2)_k$C(O)—(NH—$CR^1R^2$—C(O))$_d$—NH—$(C_2H_4$—O)$_j$—, —$(CH_2)_k$C(O)—(NH—$CR^1R^2$—C(O))$_d$;

a and b are each independently 0 or 1;

each k, k1 and k2 are independently an integer of 0 to 10, preferably 0, 1 or 2; especially 1 or 2;

d is an integer of 1 to 10, especially 1 or 2;

j is an integer of 1 to 10, especially 1, 3, or 4;

$R^1$ and $R^2$ are each independently selected from: hydrogen, —OH, —$NH_2$, —$C_{1-6}$ alkyl, —O—$C_{1-6}$ alkyl, —NH—$C_{1-6}$ alkyl, —$C_{1-6}$ alkyl-$NH_2$, —N($C_{1-6}$ alkyl)-$C_{1-6}$ alkyl, —$C_{1-6}$ alkyl-O—$C_{1-6}$ alkyl, —$C_{1-6}$ alkyl-NH—$C_{1-6}$ alkyl, —C(O)—$C_{1-6}$ alkyl, —NHC(O)—$C_{1-6}$ alkyl, —C(O)—$NH_2$, —C(O)NH—$C_{1-6}$ alkyl, —C(O)N($C_{1-6}$ alkyl)-$C_{1-6}$ alkyl, —S(═O)$_2$—$C_{1-6}$ alkyl, —NHS(═O)$_2$—$C_{1-6}$ alkyl, —S(═O)$_2$O—$C_{1-6}$ alkyl, —S(═O)$_2$NH—$C_{1-6}$ alkyl and —S(═O)$_2$N($C_{1-6}$ alkyl)-$C_{1-6}$ alkyl;

PL is a payload which is an immune agonist.

In another aspect, provided is an antibody-drug conjugates, with the formular (II):

(II)

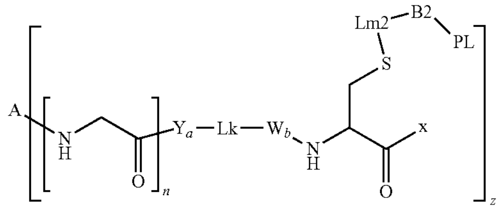

wherein, n, Y, Lk, W, Lm2, B2, x, PL, a and b are as defined in formula (I);

z is an integer of 1 to 20;

A is a targeting molecule which is an antibody or an antigen binding fragment.

The antibody-immune agonist conjugates (AIACs) of the present invention provides a novel type of tumor targeting therapy. In vitro experiments demonstrate that the AIACs can induce higher TNFα production compared to naked unmodified antibody. In vivo experiments of the AIACs show anti-tumor effect.

BRIEF DESCRIPTION OF THE DRAWINGS

FIG. 23: Tumor volume change over time in SCID Beige mice with NCI N87 CDX model dosed with: Vehicle (PBS pH 6.5), antibody, and conjugates AC102-6-1-1 and AC102-8-1-1 at 5 mg/kg.

FIG. 24: Tumor volume change over time in SCID Beige mice with NCI N87 CDX model dosed with 0.5, 1, and 3 mg/kg AC102-8-1-1.

FIG. 25: Tumor volume change over time in SCID Beige mice with JIMT1 CDX model dosed with 5 mg/kg AC102-8-1-1.

FIG. 26: Tumor volume change over time in MC38 model overexpressing hHER2 dosed with 3 mg/kg and 10 mg/kg AC102-6-1-1.

FIG. 27: Tumor volume change over time in MC38 model overexpressing hHER2 dosed with 3 mg/kg and 10 mg/kg AC102-8-1-1.

FIG. 28: Tumor volume change over time in NCI-N87 xenograft model dosed with 5 mg/kg AC102-6-2-1 and AC102-8-2-1.

FIG. 29: Tumor volume change over time in MDA-MB-468 xenograft model dosed with 3 mg/kg AC102-8-2-1 and AC201-1-2-1.

FIG. 30: Tumor volume change over time in NUGC4 model dosed with 5 mg/kg AC102-8-3-1 and antibodies.

DETAILED DESCRIPTION

Figure 1:
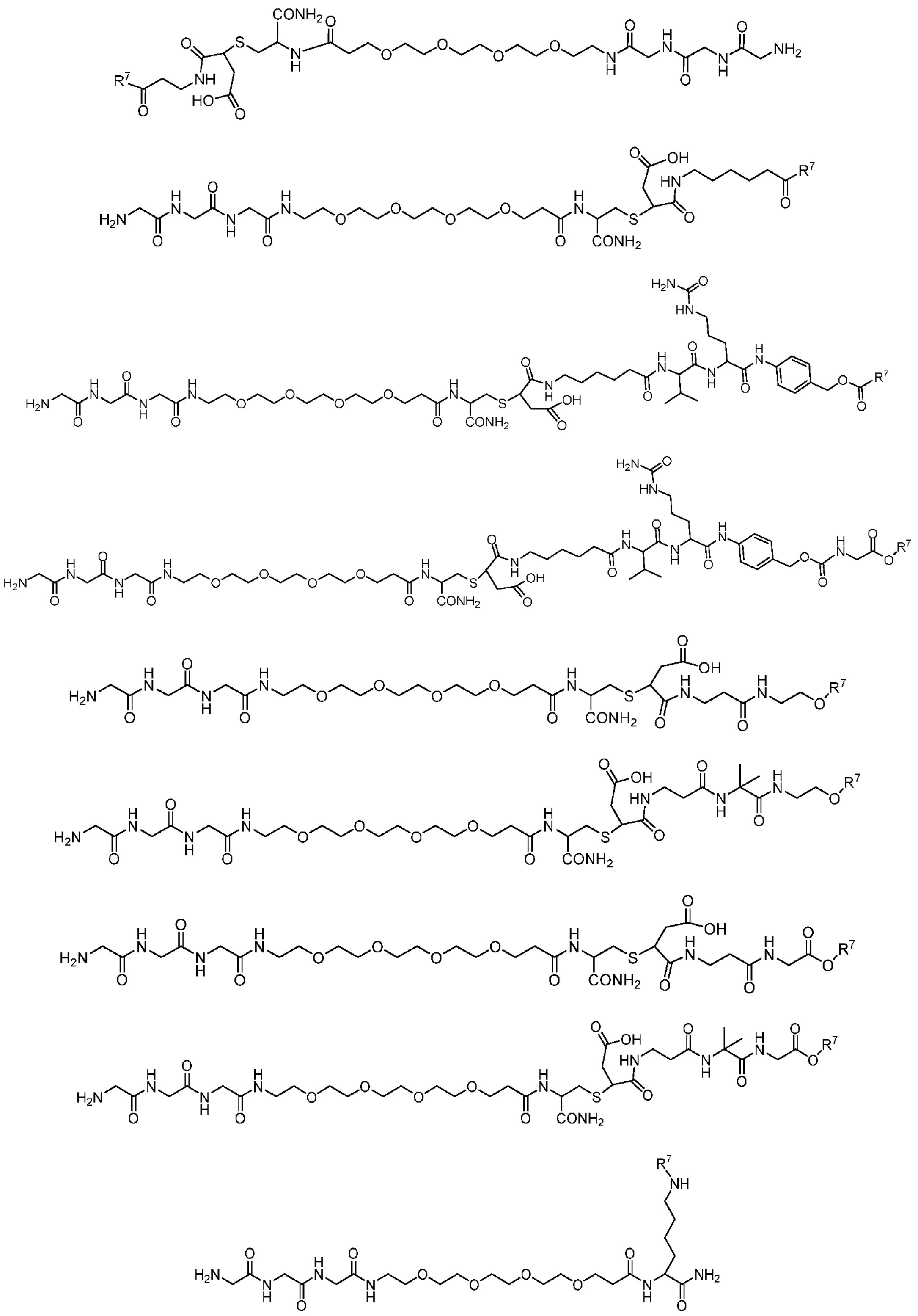
FIG. 1: Illustrative examples of the compound of formula (I'). R' is as defined herein.

The specific embodiments are provided below to illustrate technical contents of the present disclosure. Those skilled in the art can easily understand other advantages and effects of the present disclosure through the contents disclosed in the specification. The present disclosure can also be implemented or applied through other different specific embodiments. Various modifications and variations can be made by those skilled in the art without departing from the spirit of the present disclosure.

Definitions

Unless otherwise defined hereinafter, all technical and scientific terms used herein have the same meaning as commonly understood by those skilled in the art. The techniques used herein refer to those that are generally understood in the art, including the variants and equivalent substitutions that are obvious to those skilled in the art. While the following terms are believed to be readily comprehensible by those skilled in the art, the following definitions are set forth to better illustrate the present disclosure. When a trade name is present herein, it refers to the corresponding commodity or the active ingredient thereof. All patents, published patents applications and publications cited herein are hereby incorporated by reference.

When a certain amount, concentration, or other value or parameter is set forth in the form of a range, a preferred range, or a preferred upper limit or a preferred lower limit, it should be understood that it is equivalent to specifically revealing any range formed by combining any upper limit or preferred value with any lower limit or preferred value, regardless of whether the said range is explicitly recited. Unless otherwise stated, the numerical ranges listed herein are intended to include the endpoints of the range and all integers and fractions (decimals) within the range. For example, the expression "i is an integer of 2 to 20" means that i is any integer of 2 to 20, for example, i can be 2, 3, 4, 5, 6, 7, 8, 9, 10, 11, 12, 13, 14, 15, 16, 17, 18, 19 or 20. Other similar expressions should also be understood in a similar manner.

Unless otherwise stated herein, singular forms like "a" and "the" include the plural forms. The expression "one or more" or "at least one" may mean 1, 2, 3, 4, 5, 6, 7, 8, 9 or more.

The terms "about" and "approximately", when used in connection with a numerical variable, generally mean that the value of the variable and all values of the variable are within experimental error (for example, within a 95% confidence interval for the mean) or within ±10% of a specified value, or a wider range.

The term "stoichiometric ratio" means matching various substances according to a certain amount by weight. For example, in the present disclosure, the active ingredient is mixed with a filler, a binder, and a lubricant in a designated weight ratio.

The term "optional" or "optionally" means the event described subsequent thereto may, but not necessarily happen, and the description includes the cases wherein the said event or circumstance happens or does not happen.

The expression "comprising" or similar expressions "including," "containing" and "having" are open-ended, and do not exclude additional unrecited elements, steps, or ingredients. The expression "consisting of" excludes any element, step, or ingredient not designated. The expression "consisting essentially of" means that the scope is limited to the designated elements, steps or ingredients, plus elements, steps or ingredients that are optionally present that do not substantially affect the essential and novel characteristics of the claimed subject matter. It should be understood that the expression "comprising" encompasses the expressions "consisting essentially of" and "consisting of".

The term "targeting molecule" refers to a molecule that has an affinity for a particular target (e.g., receptor, cell surface protein, cytokine, etc.). A targeting molecule can deliver the payload to a specific site in vivo through targeted delivery. A targeting molecule can recognize one or more targets. The specific target sites are defined by the targets it recognizes. For example, a targeting molecule that targets a receptor can deliver a payload to a site containing a large number of the receptor. Examples of targeting molecules include, but are not limited to antibodies, antibody fragments, binding proteins for a given antigen, antibody mimics, scaffold proteins having affinity for a given target, ligands, and the like.

As used herein, the term "antibody" is used in a broad way and particularly includes intact monoclonal antibodies, polyclonal antibodies, monospecific antibodies, multispecific antibodies (e.g., bispecific antibodies), and antibody fragments, as long as they have the desired biological activity. The antibody may be of any subtype (such as IgG, IgE, IgM, IgD, and IgA) or subclass, and may be derived from any suitable species. In some embodiments, the antibody is of human or murine origin. The antibody may also be a fully human antibody, humanized antibody or chimeric antibody prepared by recombinant methods.

Monoclonal antibodies are used herein to refer to antibodies obtained from a substantially homogeneous population of antibodies, i.e., the individual antibodies constituting the population are identical except for a small number of possible natural mutations. Monoclonal antibodies are highly specific for a single antigenic site. The word "monoclonal" refers to that the characteristics of the antibody are derived from a substantially homogeneous population of antibodies and are not to be construed as requiring some particular methods to produce the antibody.

An intact antibody or full-length antibody essentially comprises the antigen-binding variable region(s) as well as the light chain constant region(s) ($C_L$) and heavy chain constant region(s) ($C_H$), which could include $C_H1$, $C_H2$, $C_H3$ and $C_H4$, depending on the subtype of the antibody. An antigen-biding variable region (also known as a fragment variable region, Fv fragment) typically comprises a light chain variable region ($V_L$) and a heavy chain variable region ($V_H$). A constant region can be a constant region with a native sequence (such as a constant region with a human native sequence) or an amino acid sequence variant thereof. The variable region recognizes and interacts with the target antigen. The constant region can be recognized by and interacts with the immune system.

An antibody fragment may comprise a portion of an intact antibody, preferably its antigen binding region or variable region. Examples of antibody fragments include Fab, Fab', $F(ab')_2$, Fd fragment consisting of $V_H$ and $C_H1$ domains, Fv fragment, single-domain antibody (dAb) fragment, and isolated complementarity determining region (CDR). The Fab fragment is an antibody fragment obtained by papain digestion of a full-length immunoglobulin, or a fragment having the same structure produced by, for example, recombinant expression. A Fab fragment comprises a light chain (comprising a $V_L$ and a $C_L$) and another chain, wherein the said other chain comprises a variable domain of the heavy chain ($V_H$) and a constant region domain of the heavy chain ($C_H1$). The $F(ab')_2$ fragment is an antibody fragment obtained by pepsin digestion of an immunoglobulin at pH 4.0-4.5, or a fragment having the same structure produced by, for example, recombinant expression. The $F(ab')_2$ fragment essentially comprises two Fab fragments, wherein each heavy chain portion comprises a few additional amino acids, including the cysteines that form disulfide bonds connecting the two fragments. A Fab' fragment is a fragment comprising one half of a $F(ab')_2$ fragment (one heavy chain and one light chain). The antibody fragment may comprise a plurality of chains joined together, for example, via a disulfide bond and/or via a peptide linking unit. Examples of antibody fragments also include single-chain Fv (scFv), Fv, dsFv, diabody, Fd and Fd' fragments, and other fragments, including modified fragments. An antibody fragment typically comprises at least or about 50 amino acids, and typically at least or about 200 amino acids. An antigen-binding fragment can include any antibody fragment that, when inserted into an antibody framework (e.g., by substitution of the corresponding region), can result in an antibody that immunospecifically binds to the antigen.

Antibodies according to the present disclosure can be prepared using techniques well known in the art, such as the following techniques or a combination thereof: recombinant techniques, phage display techniques, synthetic techniques, or other techniques known in the art. For example, a genetically engineered recombinant antibody (or antibody mimic) can be expressed by a suitable culture system (e.g., *E. coli* or mammalian cells). The engineering can refer to, for example, the introduction of a ligase-specific recognition sequence at its terminals.

HER2 refers to human epidermal growth factor receptor-2, which belongs to the epidermal growth factor (EGFR) receptor tyrosine kinase family. In the present application, the terms ErbB2 and HER2 have the same meaning and can be used interchangeably.

TROP2 is a transmembrane glycoprotein encoded by the Tacstd2 gene. TROP2 is an intracellular calcium signal transducer and is overexpressed in a variety of tumors.

CLDN18.2 (Claudin-18 isoform 2) is a member of the human claudin family. CLDN18.2 is a pan-cancer target expressed in primary lesions and metastases of several human cancer types.

As used herein, the term "targeting molecule-drug conjugate" is referred to as "conjugate". Examples of conjugates include, but are not limited to, antibody-drug conjugates.

A small molecule compound refers to a molecule with a size comparable to that of an organic molecule commonly used in medicine. The term does not encompass biological macromolecules (e.g., proteins, nucleic acids, etc.), but encompasses low molecular weight peptides or derivatives thereof, such as dipeptides, tripeptides, tetrapeptides, pentapeptides, and the like. Typically, the molecular weight of the small molecule compound can be, for example, about 100 to about 2000 Da, about 200 to about 1000 Da, about 200 to about 900 Da, about 200 to about 800 Da, about 200 to about 700 Da, about 200 to about 600 Da, about 200 to about 500 Da.

Immune agonist refers to an agonist which can induce or enhance immune response to the tumor, such through activation of immune cells, including but not limited to DCs, B cells, macrophages, NK cells, and T cells. The non-limiting examples of immune agonists such as TLR agonists, including but not limited to agonists of TLR7 and/or TLR8 and/or TLR9 (e.g., Imiquimod, Resiquimod, 852A and VTX-2337) and STING agonists (e.g., ADU-S100 and MK-1454) are known in the art.

Linking unit refers to a functional group that covalently bonds two or more moieties in a compound or material. For example, the linking unit can serve to covalently bond adjuvant moieties of targeting molecule(s) and/or payload (s).

A spacer is a structure that is located between different structural modules and can spatially separate the structural modules. The definition of spacer is not limited by whether it has a certain function or whether it can be cleaved or degraded in vivo. Examples of spacers include but are not limited to amino acids and non-amino acid structures, wherein non-amino acid structures can be, but are not limited to, amino acid derivatives or analogues. "Spacer sequence" refers to an amino acid sequence serving as a spacer, and examples thereof include but are not limited to a single amino acid such as Leu, Gln, etc., a sequence containing a plurality of amino acids, for example, a sequence containing two amino acids such as GA, etc., or, for example, GGGGS, GGGGSGGGGS, GGGGSGGGGSGGGGS, etc. Other examples of spacers include, for example, self-immolative spacers such as PABC (p-aminobenzyloxycarbonyl), and the like.

The term "alkyl" refers to a straight or branched saturated aliphatic hydrocarbon group consisting of carbon atoms and hydrogen atoms, which is connected to the rest of the molecule through a single bond. The alkyl group may contain 1 to 20 carbon atoms, referring to $C_1$-$C_{20}$ alkyl group, for example, $C_1$-$C_4$ alkyl group, $C_1$-$C_3$ alkyl group, $C_1$-$C_2$ alkyl, $C_3$ alkyl, $C_4$ alkyl, $C_3$-$C_6$ alkyl. Non-limiting examples of alkyl groups include but are not limited to methyl, ethyl, propyl, butyl, pentyl, hexyl, isopropyl, isobutyl, sec-butyl, tert-butyl, isopentyl, 2-methylbutyl, 1-methylbutyl, 1-ethylpropyl, 1,2-dimethylpropyl, neopentyl, 1,1-dimethylpropyl, 4-methylpentyl, 3-methylpentyl, 2-methylpentyl, 1-methylpentyl, 2-ethylbutyl, 1-ethylbutyl, 3,3-dimethylbutyl, 2,2-dimethyl butyl, 1,1-dimethylbutyl, 2,3-dimethylbutyl, 1,3-dimethylbutyl or 1,2-dimethylbutyl, or their isomers. A bivalent radical refers to a group obtained from the corresponding monovalent radical by removing one hydrogen atom from a carbon atom with free valence electron(s). A bivalent radical have two connecting sites which are connected to the rest of the molecule. For example, an "alkylene" or an "alkylidene" refers to a saturated divalent hydrocarbon group, either straight or branched. Examples of alkylene groups include but are not limited to methylene ($-CH_2-$), ethylene ($-C_2H_4-$), propylene ($-C_3H_6-$), butylene ($-C_4H_8-$), pentylene ($-C_5H_{10}-$), hexylene ($-C_6H_{12}-$), 1-methylethylene ($-CH(CH_3)CH_2-$), 2-methylethylene ($-CH_2CH(CH_3)-$), methylpropylene, ethylpropylene, and the like.

As used herein, when a group is combined with another group, the connection of the groups may be linear or branched, provided that a chemically stable structure is formed. The structure formed by such a combination can be connected to other moieties of the molecule via any suitable atom in the structure, preferably via a designated chemical bond. For example, when describing a combination of a $C_{1-4}$ alkylene with one of the groups including $-CH_2-$, $-NH-$, $-C(O)-$, $-NHC(O)-$, $-C(O)NH-$, the $C_{1-4}$ alkylene may form a linear connection with the above groups, such as $C_{1-4}$ alkylene-$CH_2-$, $C_{1-4}$ alkylene-NH—, $C_{1-4}$ alkylene-C(O)—, $C_{1-4}$ alkylene-NHC(O)—, $C_{1-4}$ alkylene-C(O)NH—, $-CH_2-C_{1-4}$ alkylene, $-NH-C_{1-4}$ alkylene, $-C(O)-C_{1-4}$ alkylene, $-NHC(O)-C_{1-4}$ alkylene, $-C(O)NH-C_{1-4}$ alkylene. The resulting bivalent structure can be further connected to other moieties of the molecule.

The term "heterocycle", employed alone or in combination with other terms, (and variations thereof such as "heterocyclic", or "heterocyclyl") broadly refers to a single aliphatic ring, usually with 3 to 12 ring atoms, containing at least 2 carbon atoms in addition to one or more, preferably one to three heteroatoms independently selected from oxygen, sulfur, nitrogen and phosphorus as well as combinations comprising at least one of the foregoing heteroatoms. Alternatively, a heterocycle as defined above may be multicyclic ring system (e.g. bicyclic) in which two or more rings may be fused or bridged or spiro together, wherein at least one such ring contains one or more heteroatoms independently selected from oxygen, sulfur, nitrogen and phosphorus.

The heterocyclyl may be, for example, a four-membered ring, such as azetidinyl, oxetanyl, or a five-membered ring, such as tetrahydrofuranyl, dioxolinyl, pyrrolidinyl, imidazolidinyl, pyrazolidinyl, pyrrolinyl, oxopyrrolidinyl, 2-oxo-imidazolidine-1-yl; or six-membered ring, such as tetrahydropyranyl, piperidinyl, morpholinyl, dithianyl, thiomorpholinyl, piperazinyl, 1,1-dioxo-1,2-thiazinane-2-yl or trithianyl; or a seven-membered ring, such as a diazepine ring. Optionally, the heterocyclyl can be benzo-fused.

The heterocyclyl may be bicyclic without limitation, for example, a five-membered fused five-membered ring, such as hexahydrocyclopentane[c]pyrrole-2(1H)-yl; or a five-membered fused six-membered bicyclic ring, such as hexahydropyrrolo[1,2-a]pyrazine-2(1H)-yl.

As mentioned above, the heterocycle may be unsaturated, that is, it may contain one or more double bonds without limitation. For example, an unsaturated heterocycle containing a nitrogen atom may be 1,6-dihydropyrimidine, 1,2-dihydropyrimidine, 1,4-dihydropyrimidine, 1,6-dihydropyridine, 1,2-dihydropyridine, 1,4-dihydropyridine, 2,3-dihydro-1H-pyrrole, 3,4-dihydro-1H-pyrrole, 2,5-dihydro-1H-pyrrolyl, 4H-[1,3,4]thiadiazinyl, 4,5-dihydrooxazolyl or 4H-[1,4]thiazinyl ring, the unsaturated heterocycle containing an oxygen atom may be 2H-pyran, 4H-pyran, or 2,3-dihydrofuran, and the unsaturated heterocycle containing a sulfur atom may be 2H-thiopyran or 4H-thiopyran. The heterocycle can be benzo-fused without limitation, such as dihydroisoquinolinyl ring.

The term "heteroaryl" should be understood to preferably mean a monovalent monocyclic, bicyclic, or tricyclic aromatic ring system having 5, 6, 7, 8, 9 or 10 ring atoms ("5- to 10-membered heteroaryl"), especially 5 or 6 or 9 or 10 ring atoms, and at least one of the ring atoms (suitably 1-4, more suitably 1, 2 or 3) may be the same or different heteroatoms such as oxygen, nitrogen, or sulfur ring system. In addition, the heteroaryl can be benzo-fused in each case. In particular, the heteroaryl is selected from the group consisting of thienyl, furyl, pyrrolyl, oxazolyl, thiazolyl, imidazolyl, pyrazolyl, isoxazolyl, isothiazolyl, oxadiazolyl, triazolyl, thiodiazolyl, etc. and their benzo derivatives, such as benzofuranyl, benzothienyl, benzoxazolyl, benzisoxazolyl, benzimidazolyl, benzotriazolyl, indazole, indolyl, isoindolyl, etc.; or pyridyl, pyridazinyl, pyrimidinyl, pyrazinyl, triazinyl, etc. and their benzo-fused derivatives, such as quinolinyl, quinazolinyl, isoquinolinyl, etc. or azocinyl, indolizinyl, purinyl, etc. and their benzo derivatives; or cinnolinyl, phthalazinyl, quinazolinyl, quinoxalinyl, naphthyridinyl, carbazolyl, acridinyl, etc.

Compound of Formula (I')

In one aspect, provide is a compound of formula (I') (formula (I'-1) or formula (I'-2)):

$$D1\text{-}Y_a\text{-}Lk\text{-}W_b\text{-}A2_p\text{-}Lm2_p\text{-}B2 \quad (I'\text{-}1)$$

$$B1\text{-}Lm1_p\text{-}A1_p\text{-}W_b\text{-}Lk\text{-}Y_a\text{-}D2 \quad (I'\text{-}2)$$

wherein,

D1 and D2 are independently a moiety comprising a recognition sequence of the ligase acceptor or donor substrate;

B1 and B2 are each independently a combination of 1) a $C_{2-30}$ alkylene and wherein one or more —$CH_2$— structures in the alkylene is optionally replaced by —$CR^1R^2$—, —O—, —C(O)—, —$NR^3$—, Cleavable sequence 1, or spacer Sp1; and 2) a terminal group;

the terminal group is hydrogen or $R^7$;

$R^7$ is a group which can leave when reacting with a group in the payload;

$R^1$, $R^2$ and $R^3$ are each independently selected from hydrogen, —OH, —$NH_2$, —$C_{1-6}$ alkyl, —O—$C_{1-6}$ alkyl, —NH—$C_{1-6}$ alkyl, —$C_{1-6}$ alkyl-$NH_2$, —N($C_{1-6}$ alkyl)-$C_{1-6}$ alkyl, —$C_{1-6}$ alkyl-O—$C_{1-6}$ alkyl, —$C_{1-6}$ alkyl-NH—$C_{1-6}$ alkyl, —C(O)—$C_{1-6}$ alkyl, —NHC(O)—$C_{1-6}$ alkyl, —C(O)—$NH_2$, —C(O)NH—$C_{1-6}$ alkyl, —C(O)N($C_{1-6}$ alkyl)-$C_{1-6}$ alkyl, —S(=O)$_2$—$C_{1-6}$ alkyl, —NHS(=O)$_2$—$C_{1-6}$ alkyl, —S(=O)$_2$O—$C_{1-6}$ alkyl, —S(=O)$_2$NH—$C_{1-6}$ alkyl and —S(=O)$_2$N($C_{1-6}$ alkyl)-$C_{1-6}$ alkyl;

Lm1 and Lm2 are each independently a ring-opened succinimide moiety;

A1 and A2 are each independently is a moiety conjugated with Lm1 or Lm2 through a disulfide bond, a thioether bond, a thioester bond, or a urethane bond, Lk is a combination of $L_1$-$L_2$-$L_3$;

$L_1$ and $L_3$ are each independently selected from:

—$CH_2$—, —NH—, —C(O)—, —NHC(O)—, —C(O)NH—; and combination of a $C_{1-4}$ alkylene with one of the following groups: —$CH_2$—, —NH—, —C(O)—, —NHC(O)—, —C(O)NH—;

$L_2$ is absent or is a $C_{7-34}$ alkylene, and wherein one or more (—$CH_2$—) structures in the alkylene is optionally replaced by —O—;

$L_1$, $L_2$ and $L_3$ are each optionally and independently substituted with 1, 2 or 3 substituents selected from —$OR^4$ and —$NR^5R^6$;

$R^4$, $R^5$ and $R^6$ are each independently selected from hydrogen, —$C_{1-6}$ alkyl, —C(O)—$C_{1-6}$ alkyl and —S(=O)$_2$—$C_{1-6}$ alkyl;

Y and W are each independently absent or selected from a Cleavable sequence 2, spacer Sp2, and the combination thereof;

Cleavable sequence 1 comprises an amino acid sequence which can be cleaved by enzyme, and Cleavable sequence 1 comprises 1-10 amino acids;

Cleavable sequence 2 comprises an amino acid sequence which can be cleaved by enzyme, and Cleavable sequence 2 comprises 1-10 amino acids;

Sp1 and Sp2 are each independently selected from a spacer sequence containing 1-20 amino acids, PABC, and the combination thereof;

a, b and p are each independently 0 or 1.

In one embodiment, a and b are both 0. In one embodiment, a is 1, b is 0. In one embodiment, p is 0.

In one embodiment, $R^1$ and $R^2$ are both hydrogen, or both —$C_{1-6}$ alkyl. In one embodiment, $R^1$ and $R^2$ are each independently selected from hydrogen, —C(O)—$C_{1-6}$ alkyl, —C(O)—$NH_2$, —C(O)NH—$C_{1-6}$ alkyl, —C(O)N($C_{1-6}$ alkyl)-$C_{1-6}$ alkyl, —S(=O)$_2$—$C_{1-6}$ alkyl, —S(=O)$_2$O—$C_{1-6}$ alkyl, —S(=O)$_2$NH—$C_{1-6}$ alkyl and —S(=O)$_2$N($C_{1-6}$ alkyl)-$C_{1-6}$ alkyl, or are each independently selected from —$C_{1-6}$ alkyl, —C(O)—$NH_2$, —C(O)NH—$C_{1-6}$ alkyl, —C(O)N($C_{1-6}$ alkyl)-$C_{1-6}$ alkyl, and —S(=O)$_2$—$C_{1-6}$ alkyl, —S(=O)$_2$O—$C_{1-6}$ alkyl, —S(=O)$_2$NH—$C_{1-6}$ alkyl and —S(=O)$_2$N($C_{1-6}$ alkyl)-$C_{1-6}$ alkyl. In one embodiment, $R^1$ and $R^2$ are both hydrogen, or both —$C_{1-6}$ alkyl, or are each independently selected from hydrogen, —C(O)—$C_{1-6}$ alkyl and —S(=O)$_2$—$C_{1-6}$ alkyl, or are each independently selected from —$C_{1-6}$ alkyl, —C(O)—$C_{1-6}$ alkyl and —S(=O)$_2$—$C_{1-6}$ alkyl.

In one embodiment, $L^1$, $L^2$ and $L^3$ are independently substituted with 1, 2, or 3 substituents selected from $—OR^4$ and $—NR^5R^6$. Substitutions occur, for example, on $—CH_3$, $—CH_2—$ or

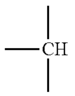

structure, especially on $—CH_2—$.

In one embodiment, $L^1$ is —NH—, or is a combination of a $C_{1-4}$ alkylene with —NH—. In another embodiment, $L^1$ is —C(O)—, or is a combination of a $C_{1-4}$ alkylene with —C(O)—.

In one embodiment, $L^3$ is —NH—, or is a combination of a $C_{1-4}$ alkylene with —NH—. In another embodiment, $L^3$ is —C(O)—, or is a combination of a $C_{1-4}$ alkylene with —C(O)—.

In one embodiment, $L^2$ is a $C_{7-34}$ alkylene, wherein the alkylene is a straight or a branched alkylene group, and optionally one or more of the $—CH_2—$ structures in the alkylene can be replaced by —O—, and the alkylene is optionally substituted with 1, 2 or 3 substituents selected from $—OR^4$ and $—NR^5R^6$. In yet another embodiment, $L^2$ is selected from bivalent groups optionally substituted with 1, 2 or 3 substituents selected from $—OR^4$ and $—NR^5R^6$, wherein the said bivalent groups are as follows: methylene, ethylene, propylene, butylene, pentylene, hexylene, 1-methylethylene, 2-methylethylene, 2-methylpropylene and 2-ethylpropylene.

In another embodiment, $L^2$ is $—(C_2H_4—O)_i—C_{1-4}$ alkylene; i is an integer of 2 to 10. In one embodiment, $L^2$ is $C_{1-4}$ alkylene-$(O—C_2H_4)_i—$. "$—(C_2H_4—O)_i—$" or "$—(O—C_2H_4)_i—$" represents a structure formed by polymerization of PEG units, wherein i indicates the number of PEG units. In another embodiment, $L^2$ is $—(C_2H_4—O)_i—C_{1-2}$ alkylene. In a particular embodiment, $L^2$ is $—(C_2H_4—O)_i—C_2H_4—$. In another embodiment, $L^2$ is a $C_{1-2}$ alkylene-$(O—C_2H_4)_i—$. In a particular embodiment, $L^2$ is $—C_2H_4—(O—C_2H_4)_i—$. In one embodiment, i is selected from the following values: 2-10, 2-8, 2-6, 2-4 or 4-6. In a particular embodiment, i is 4.

In one embodiment, Y and W are each independently absent or selected from Cleavable 1, spacer Sp2, and the combination thereof. In a particular embodiment, a is 0 and therefore Y is absent. In another particular embodiment, b is 0 and therefore W is absent. In yet another particular embodiment, Y and W are both absent. In one embodiment, Cleavable sequence 2 comprises an amino acid sequence that can be recognized as enzyme substrate and can be cleaved by the enzyme. In a particular embodiment, Cleavable sequence 2 can be enzymatically cleaved in the cell, especially in the lysosomal. In another particular embodiment, Cleavable sequence 2 can be cleaved by protease, in particular by cathepsins. In yet another particular embodiment, Cleavable sequence 2 can be cleaved by glutaminase. In one embodiment, Cleavable sequence 2 is selected from a cathepsin restriction site, a glutaminase restriction site, and combinations thereof. In one embodiment, Cleavable sequence 2 is selected from Phe-Lys, Val-Cit, Val-Lys, GLy-Phe-Leu-Gly, Ala-Leu-Ala-Leu and the combination thereof.

In one embodiment, Y and W are each independently absent or selected from spacer Sp2. In another embodiment, Sp2 is a spacer sequence comprising 1-10, preferably 1-6, more preferably 1-4 amino acids. In a particular embodiment, Sp2 is Leu. In another particular embodiment, Sp2 is Gln. In one embodiment, Sp2 is PABC. In yet another embodiment, Y and W are each independently selected from Phe-Lys-PABC, Val-Cit-PABC, and Val-Lys-PABC.

In one embodiment, the amino acids comprised by Y and/or W may be natural or unnatural. In a particular embodiment, Y is amino acid fragment 1. Amino acid fragment 1 comprises 1-30 natural or unnatural amino acids, which are each independently the same or different. And amino acid fragment 1 is selected from: a cleavable sequence comprising 1-10 amino acids, a spacer sequence comprising 1-20 amino acids, and the combination thereof. In another particular embodiment, W is amino acid fragment 2. Amino acid fragment 2 comprises 1-30 natural or unnatural amino acids, which are each independently the same or different. And amino acid fragment 2 is selected from: a cleavable sequence comprising 1-10 amino acids, a spacer sequence comprising 1-20 amino acids, and the combination thereof.

Moiety Comprising Recognition Sequence of the Ligase Acceptor or Donor Substrate In one embodiment, the ligase is a transpeptidase. In one embodiment, the ligase is selected from a natural transpeptidase, an unnatural transpeptidase, variants thereof, and the combination thereof. Unnatural transpeptidase enzymes can be, but are not limited to, those obtained by engineering of natural transpeptidase. In a preferred embodiment, the ligase is selected from a natural Sortase, an unnatural Sortase, and the combination thereof. The species of natural Sortase include Sortase A, Sortase B, Sortase C, Sortase D, Sortase *L. plantarum*, etc. (US20110321183A1). The type of ligase corresponds to the ligase recognition sequence and is thereby used to achieve specific conjugation between different molecules or structural fragments. In one embodiment, the recognition sequence of the ligase acceptor substrate is selected from oligomeric glycine, oligomeric alanine, and a mixture of oligomeric glycine/alanine having a degree of polymerization of 3-10. In a particular embodiment, the recognition sequence of the ligase acceptor substrate is Gr, wherein G is glycine (Gly), and n is an integer of 3 to 10. In another particular embodiment, the ligase is Sortase A from *Staphylococcus aureus*. Accordingly, the ligase recognition sequence may be the typical recognition sequence LPXTG of the enzyme. In yet another particular embodiment, the recognition sequence of the ligase donor substrate is LPXTGJ, and the recognition sequence of the ligase acceptor substrate is Gr wherein X can be any single amino acid that is natural or unnatural; J is absent, or is an amino acid fragment comprising 1-10 amino acids, optionally labeled. In one embodiment, J is absent. In yet another embodiment, J is an amino acid fragment comprising 1-10 amino acids, wherein each amino acid is independently any natural or unnatural amino acid. In another embodiment, J is Gm, wherein m is an integer of 1 to 10. In yet another particular embodiment, the recognition sequence of the ligase donor substrate is LPETG. In another particular embodiment, the recognition sequence of the ligase donor substrate is LPETGG. In one embodiment, the ligase is Sortase B from *Staphylococcus aureus* and the corresponding donor substrate recognition sequence can be NPQTN. In another embodiment, the ligase is Sortase B from *Bacillus anthracia* and the corresponding donor substrate recognition sequence can be NPKTG. In yet another embodiment, the ligase is Sortase A from *Streptococcus pyogenes* and the corresponding donor substrate recognition sequence can be LPXTGJ, wherein J is as defined above. In another embodiment, the ligase is Sortase subfamily 5 from *Streptomyces coelicolor*, and the corresponding donor substrate recognition sequence can be LAXTG. In yet another embodiment, the ligase is Sortase A from *Lactobacillus plantarum* and the corresponding donor substrate recognition sequence can be LPQTSEQ. The ligase recognition sequence can also be other totally new recognition sequence for transpeptidase optimized by manual screening.

Moiety Comprising Reactive Group

Reactive Group for Connection with Payload

In one embodiment, B1 or B2 is used for connection to the payload. For connection with the payload, the compound of formula (I') comprises a reactive group. In one embodiment, B1 or B2 in the compound of formula (I') is connected to the payload through an amide bond or an ester bond or an ether bond. In one embodiment, the reactive group in B1 or B2 in formula (I') is independently a reactive group for condensation reaction, nucleophilic addition or electrophilic addition (such as reactive C=O moiety, reactive C=C—C=O moiety, amino group, amine group, hydroxy group, thiol group), or a reactive group for substitution reaction (such as a leaving group attached to an O, C, N or S atom). In one embodiment, the reactive group in B1 or B2 is independently selected from carboxyl group, sulfonic acid group, phosphoryl group with free —OH end, active ester, aldehyde group, isocyanate group, acceptor group of Michael addition (such as maleimide group), amino group, amine group, hydroxy group, thiol group, pyridyldithiol group and haloacetic group. In a specific embodiment, the reactive group in B1 or B2 which is used to connect to the payload is independently selected from amino group, amine group, hydroxy group, thiol group, carboxyl group and active ester. In another specific embodiment, B1 or B2 are connected to the payload through a group selected from —OH and —COOH, especially the hydroxy group of an alkyl alcohol or the carboxyl group of an alkyl carboxylic acid.

In one embodiment, the reactive group in B1 or B2 is independently amino group, amine group or hydroxy group, which reacts with corresponding groups (such as carboxyl group, sulfonic acid group, phosphoryl group with free —OH end, active ester, acid chloride or isocyanate group) in the payload. In another embodiment, the reactive group in B1 or B2 is independently carboxyl group, sulfonic acid group, phosphoryl group with free —OH end, active ester or isocyanate group, which reacts with corresponding groups (such as amino group, amine group or hydroxy group) in the payload.

In one embodiment, the reactive group in B1 or B2 is independently amino group, hydroxy group or thiol group, which reacts with corresponding groups (such as halogen, hydroxy group, thiol group, aldehyde group) in the payload. In another embodiment, the reactive group in B1 or B2 is independently hydroxy group, which reacts with corresponding groups (such as such as halogen or hydroxy group) in the payload.

B1 and B2

In one embodiment, B1 and B2 each independently is a combination of 1) and 2):

1) one of or a combination of two or more of the bivalent groups selected from: $—(CH_2)_kC(O)—$, $—NR^3—$, $—(C_2H_4—O)_i—$, $—(NH—CR^1R^2—C(O))_d—$, $—(C_2H_4)_g—$, $—C(O)(CH_2)_k—$, $—(O—C_2H_4)_i—$, $—(C(O)—CR^1R^2—NH)_d—$, Cleavable sequence 1, and spacer Sp1 and 2) a terminal group; wherein the terminal group is hydrogen or $R^7$;

k is an integer of 0 to 20, j is an integer of 1 to 20, d is an integer of 1 to 20, g is an integer of 1 to 20;

each $—(CH_2)_kC(O)—$, $—C(O)(CH_2)_k—$ and $—(C_2H_4)_g—$ are independently unsubstituted or substituted by one or more groups selected from —OH, $—NH_2$, a $C_{1-6}$ alkyl, $—O—C_{1-6}$ alkyl, $—NH—C_{1-6}$ alkyl, $—C_{1-6}$ alkyl-$NH_2$, $—N(C_{1-6}$ alkyl)-$C_{1-6}$ alkyl, $—C(O)—C_{1-6}$ alkyl, $—NHC(O)—C_{1-6}$ alkyl, $—S(=O)_2—C_{1-6}$ alkyl and $—NHS(=O)_2—C_{1-6}$ alkyl.

In one embodiment, the terminal group is hydrogen. In one embodiment, $R^7$ is hydroxy or

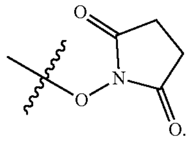 [SMILES: *ON1C(=O)CCC1=O]

In one embodiment, the terminal group $R^7$ represents the part of structure which would not appear in the product molecule resulting from the reaction of B1 or B2 with the payload, and thus in the linking unit-payload intermediate (c.f. below) the structure moiety corresponding to B1 or B2 is the said one of or the combination of two or more of the bivalent groups.

In one embodiment, each $—(CH_2)_kC(O)—$, $—C(O)(CH_2)_k—$ and $—(C_2H_4)_g—$ are independently unsubstituted or substituted by one or more groups selected from —OH, $C_{1-6}$ alkyl, $—O—C_{1-6}$ alkyl, $—N(C_{1-6}$ alkyl)-$C_{1-6}$ alkyl, $—C(O)—C_{1-6}$ alkyl, $—NHC(O)—C_{1-6}$ alkyl, $—S(=O)_2—C_{1-6}$ alkyl and $—NHS(=O)_2—C_{1-6}$ alkyl, more preferably substituted by one or more groups selected from $—C_{1-6}$ alkyl or $—NHC(O)—C_{1-6}$ alkyl. In another embodiment, each $—(CH_2)_kC(O)—$, $—C(O)(CH_2)_k—$ and $—(C_2H_4)_g—$ are independently unsubstituted or substituted by one or more groups selected from $—C(O)—NH_2$, $—NH_2$, $—C_{1-6}$ alkyl-$NH_2$, $—NH—C_{1-6}$ alkyl, preferably substituted by one or more groups selected from $—C(O)—NH_2$, $—C_{1-6}$ alkyl-$NH_2$, $—NH—C_{1-6}$ alkyl.

In one embodiment, k is selected from the following values: 0, 1, 2-10, 2-9, 2-8, 2-7, 2-6, 2-5, 2-4 or 2-3, preferably 0, 1 or 2; especially 1 or 2. In one embodiment, j is selected from the following values: 1-10, 1-9, 1-8, 1-7, 1-6, 1-5, 1-4, especially 1, 3, or 4. In one embodiment, d is selected from the following values: 1-10, 1-8, 1-6, 1-4, 1-3, 1-2. In a particular embodiment, d is 1 or 2. In a particular embodiment, d is 1. In one embodiment, g is selected from the following values: 2-10, 2-9, 2-8, 2-7, 2-6, 2-5, 2-4.

It is to be understood that when there are two or more $—(CH_2)_kC(O)—$ groups in the molecule, the value of each k is selected independently. In some embodiments, the "k"s in the molecule are denoted with or without additional numbers, for example k1, k2, k3, etc., wherein the numbers do not indicate any sequence, but are used merely to differentiate the "k"s. The other footnotes such as g, j, d should be understood in a similar way.

It is to be understood that when there are two or more $R^x$ (x being 1, 2, 3, 4, 5, 6, 7, etc.), each $R^x$ is selected independently. In some embodiments, the "x"s in the molecule are denoted with or without additional apostrophe (') or apostrophes (such as '', ''', '''', etc.), for example R, $R^{1'}$, $R^{1''}$, $R^{1'''}$, $R^{2'}$, $R^{2''}$, $R^{2'''}$, etc. The other $R^x$s such as $R^3$, $R^4$, $R^5$, $R^6$, $R^7$, such as $R^3$, $R^4$, $R^5$, $R^6$, $R^7$ should be understood in a similar way.

In another embodiment, Cleavable sequence 1 comprises an enzymatic cleavage site which is selected from an oligomeric peptide that is sensitive to protease, a cathepsin cleavage site, a glutaminase cleavage site, and the combination thereof. In a particular embodiment, Cleavable sequence 1 is selected from Phe-Lys, Val-Cit, and Val-Lys.

In another embodiment, Sp1 is a spacer sequence comprising 1-10, preferably 1-6, more preferably 1-4 amino acids. In one embodiment, Sp1 is PABC.

In one embodiment, B1 and B2 are each optionally derivatized lysine. In another embodiment, the derivatization of lysine in is selected from: 1) amidation of the carboxyl group, the resulting amide $NH_2$ being optionally substituted with a $C_{1-6}$ alkyl group; 2) linkage of the carboxyl group and/or the amino group to an amino acid fragment comprising 1-10 amino acids or a nucleotide fragment comprising 1-10 nucleotides, wherein the amino acid fragment is preferably Gly.

In one embodiment, when the terminal group combines with the bivalent group(s), the following bivalent groups each forms the following structure moiety: —$(CH_2)_k$C(O)— forms —$(CH_2)_k$C(O)—OH; —$NR^3$— forms —$NHR^3$ or $R^3$HN—; —$(C_2H_4$—$O)_i$— forms —$(C_2H_4$—$O)_i$—H; —(NH—$CR^1R^2$—C(O))$_d$— forms —(NH—$CR^1R^2$—C(O))$_d$OH; —$(C_2H_4)_g$— forms —$(C_2H_4)_g$—H, —$(C_2H_4)_g$—OH, H—$(C_2H_4)_g$— or HO—$(C_2H_4)_g$—; —C(O)$(CH_2)_k$— forms HO—C(O)$(CH_2)_k$—; —(O—$C_2H_4)_i$— forms H—(O—$C_2H_4)_i$—; —(C(O)—$CR^1R^2$—NH)$_d$— forms HO—(C(O)—$CR^1R^2$—NH)$_d$—, wherein each —$(CH_2)_k$C(O)—, —C(O)$(CH_2)_k$— and —$(C_2H_4)_g$— are independently unsubstituted or substituted by the one or more groups defined as above.

In one embodiment, B2 is selected from —$(CH_2)_k$C(O)—OH, —(NH—$CR^1R^2$—C(O))$_d$—OH, —NH—$(C_2H_4$—$O)_i$—H, -Val-Cit-PABC, -(Lys-$NH_2$), —$(CH_2)_k$C(O)—(NH—$CR^1R^2$—C(O))$_d$—OH, —$(CH_2)_k$C(O)—NH—$(C_2H_4$—$O)_i$—H, —(NH—$CR^1R^2$—C(O))$_d$—NH—$(C_2H_4$—$O)_i$—H, —$(CH_2)_k$C(O)—(NH—$CR^1R^2$—C(O))$_d$—NH—$(C_2H_4$—$O)_i$—H, —$(CH_2)_{k1}$C(O)—NH—$(C_2H_4$—$O)_i$—$(CH_2)_{k2}$C(O)-(Lys-OH), -Val-Cit-PABC—(NH—$CR^1R^2$—C(O))$_d$—OH, —$(CH_2)_k$C(O)-Val-Cit-PABC and —$(CH_2)_k$C(O)-Val-Cit-PABC—(NH—$CR^1R^2$—C(O))$_d$—OH.

In one embodiment, B2 is selected from —$(CH_2)_k$C(O)—OH, —(NH—$CR^1R^2$—C(O))$_d$—OH, —NH—$(C_2H_4$—$O)_i$—H, -Val-Cit-PABC, -(Lys-$NH_2$), —$(CH_2)_k$C(O)—(NH—$CR^1R^2$—C(O))$_d$—OH, —$(CH_2)_k$C(O)—NH—$(C_2H_4$—$O)_i$—H, —(NH—$CR^1R^2$—C(O))$_d$—NH—$(C_2H_4$—$O)_i$—H, —$(CH_2)_{k1}$C(O)—NH—$(C_2H_4$—$O)_i$—$(CH_2)_{k2}$C(O)-(Lys-OH), -Val-Cit-PABC—(NH—$CR^1R^2$—C(O))$_d$—OH, —$(CH_2)_k$C(O)-Val-Cit-PABC and —$(CH_2)_k$C(O)-Val-Cit-PABC—(NH—$CR^1R^2$—C(O))$_d$—OH.

In one embodiment, B2 is selected from —$(CH_2)_k$C(O)—OH, —(NH—$CR^1R^2$—C(O))$_d$—OH, —NH—$(C_2H_4$—$O)_i$—H, -Val-Cit-PABC, -(Lys-$NH_2$), —$(CH_2)_k$C(O)—(NH—$CR^1R^2$—C(O))$_d$—OH, —$(CH_2)_k$C(O)—NH—$(C_2H_4$—$O)_i$—H, —(NH—$CR^1R^2$—C(O))$_d$—NH—$(C_2H_4$—$O)_i$—H, —$(CH_2)_{k1}$C(O)—NH—$(C_2H_4$—$O)_i$—$(CH_2)_{k2}$C(O)-(Lys-OH), -Val-Cit-PABC—(NH—$CR^1R^2$—C(O))$_d$—OH and —$(CH_2)_k$C(O)-Val-Cit-PABC.

In one embodiment, B2 is -(Lys-$NH_2$). In one embodiment, B1 is (Lys-$NH_2$)—.

In one embodiment, B2 is selected from —$(CH_2)_k$C(O)—OH, —$(CH_2)_k$C(O)—(NH—$CR^1R^2$—C(O))$_d$—OH, —$(CH_2)_k$C(O)— NH—$(C_2H_4$—$O)_i$—H, —$(CH_2)_k$C(O)—(NH—$CR^1R^2$—C(O))$_d$— NH—$(C_2H_4$—$O)_i$—H, —$(CH_2)_k$C(O)-Val-Cit-PABC and —$(CH_2)_k$C(O)-Val-Cit-PABC—(NH—$CR^1R^2$—C(O))$_d$—OH.

In one embodiment, B2 is selected from —$(CH_2)_k$C(O)—OH, —$(CH_2)_k$C(O)—(NH—$CR^1R^2$—C(O))$_d$—OH, —$(CH_2)_k$C(O)—NH—$(C_2H_4$—$O)_i$—H, —$(CH_2)_k$C(O)-Val-Cit-PABC and —$(CH_2)_k$C(O)-Val-Cit-PABC—(NH—$CR^1R^2$—C(O))$_d$—OH.

In one embodiment, B2 is selected from —$(CH_2)_k$C(O)—OH, —$(CH_2)_k$C(O)—(NH—$CR^1R^2$—C(O))$_d$—OH, —$(CH_2)_k$C(O)—NH—$(C_2H_4$—$O)_i$—H and —$(CH_2)_k$C(O)-Val-Cit-PABC.

In one embodiment, B1 is selected from HO—C(O)$(CH_2)_k$—, HO—(C(O)—$CR^1R^2$—NH)$_d$—, H—(O—$C_2H_4)_i$—NH—, (Lys-$NH_2$)—, HO—(C(O)—$CR^1R^2$—NH)$_d$—C(O)$(CH_2)_k$—, H—(O—$C_2H_4)_i$—NH—C(O)$(CH_2)_k$—, H—(O—$C_2H_4)_i$—NH—(C(O)—$CR^1R^2$—NH)$_d$—, H—(O—$C_2H_4)_i$—NH—(C(O)—$CR^1R^2$—NH)$_d$C(O)$(CH_2)_k$—, (Lys-OH)—C(O)$(CH_2)_{k1}$—(O—$C_2H_4)_i$—NH—C(O)$(CH_2)_{k2}$—, HO—(C(O)—$CR^1R^2$—NH)$_d$-Val-Cit-PABC—, and HO—(C(O)—$CR^1R^2$—NH)$_d$-Val-Cit-PABC—C(O)$(CH_2)_{k1}$—.

In one embodiment, B1 is selected from HO—C(O)$(CH_2)_k$—, HO—(C(O)—$CR^1R^2$—NH)$_d$—, H—(O—$C_2H_4)_i$—NH—, (Lys-$NH_2$)—, HO—(C(O)—$CR^1R^2$—NH)$_d$—C(O)$(CH_2)_k$—, H—(O—$C_2H_4)_i$—NH—C(O)$(CH_2)_k$—, H—(O—$C_2H_4)_i$—NH—(C(O)—$CR^1R^2$—NH)$_d$—, (Lys-OH)—C(O)$(CH_2)_{k1}$—(O—$C_2H_4)_i$—NH—C(O)$(CH_2)_{k2}$—, HO—(C(O)—$CR^1R^2$—NH)$_d$-Val-Cit-PABC—, and HO—(C(O)—$CR^1R^2$—NH)$_d$-Val-Cit-PABC—C(O)$(CH_2)_{k1}$—.

In one embodiment, $R^1$ and $R^2$ are both hydrogen or both —$C_1$, alkyl, preferably both hydrogen or both —$C_{1-3}$ alkyl, more preferably both hydrogen or both —$C_{1-2}$ alkyl, especially both hydrogen or both methyl. In one embodiment, $R^3$ is hydrogen or —$C_{1-6}$ alkyl, preferably hydrogen or —$C_{1-2}$ alkyl, especially hydrogen.

A and Lm

In one embodiment, A1 and A2 in formula (I') are each independently a residue resulted from a reactive group which is selected from amino compound, thiol compound, pyridyldithiol compound and isocyanate. In another embodiment, A1 and A2 are each independently a moiety conjugated with Lm1 or Lm2 through a reactive group selected from a amino group, thiol group, pyridyldithio group, and isocyanate group. In a particular embodiment, A1 and A2 are each independently selected from optionally derivatized amino acids, preferably optionally derivatized cysteines or lysines.

In another particular embodiment, A1 and A2 are each independently selected from optionally derivatized cysteines. In a preferred embodiment, the derivatization of cysteine is selected from: 1) amidation of the carboxyl group, the resulting amide $NH_2$ being optionally substituted with a $C_{1-6}$ alkyl group; 2) acylation of the amino group; and 3) linkage of the carboxyl group and/or the amino group to an amino acid fragment comprising 1-10 amino acids or a nucleotide fragment comprising 1-10 nucleotides, wherein the amino acid fragment is preferably Gly. In a particular embodiment, the derivatization of cysteine refers to amidation or linkage to glycine for the carboxyl group of cysteine.

In one embodiment, A2 is

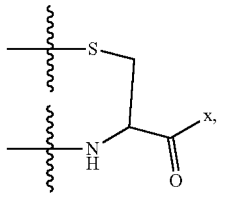

wherein x is selected from hydrogen, OH, $NH_2$, an amino acid fragment comprising 1-10 amino acids, and a nucleotide fragment comprising 1-10 nucleotides, preferably $NH_2$. In one embodiment, A1 is

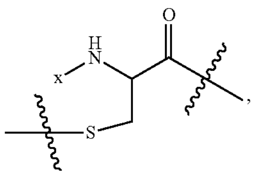

wherein x is selected from hydrogen, an amino acid fragment comprising 1-10 amino acids, and a nucleotide fragment comprising 1-10 nucleotides, preferably $NH_2$. In one embodiment, acylation of the amino group refers to the substitution with a $C_{1-6}$ alkylcarbonyl group for the amino group of cysteine.

In one embodiment, the linkage between the A moiety and the Lm moiety can be formed through the following way: the thiol group in the cysteine structure reacts with a maleimide group comprised by Lm, resulting in a thiosuccinimide structure.

In a particular embodiment, the thiol group in the cysteine structure is connected to the maleimide group by Michael addition.

Thiosuccinimide is unstable under physiological conditions and is liable to reverse Michael addition which leads to cleavage at the conjugation site. Moreover, when another thiol compound is present in the system, thiosuccinimide may also undergo thiol exchange with the other thiol compound. Both of these reactions cause the fall-off of the payload and result in toxic side effects. In the present disclosure, the ring opening of the succinimide is conducted using a ring opening reaction after the step of Michael addition. After ring opening, the succinimide no longer undergoes reverse Michael addition or thiol exchange, and thus the product is more stable. Method of ring opening reaction can be found in WO2015165413A1.

The ring-opened compound of formula (I') can be purified by semi-preparative/preparative HPLC or other suitable separation means to obtain payload-bearing formula (I') compound with high purity and defined composition, regardless of the efficiency of the succinimide ring opening reaction.

In one embodiment, Lm1 and Lm2 are each independently

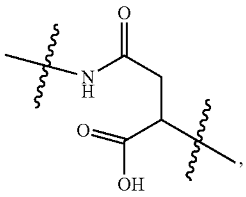,
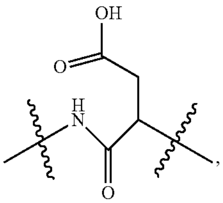,
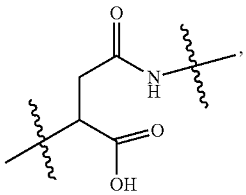,
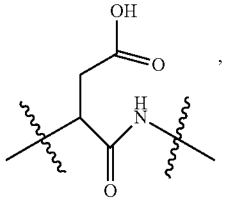, a mixture of

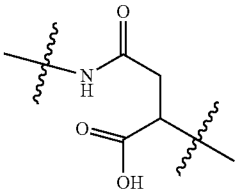
and
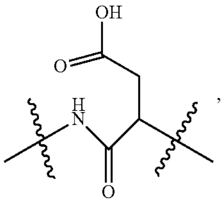, or a mixture of

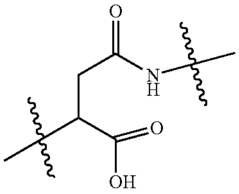
and
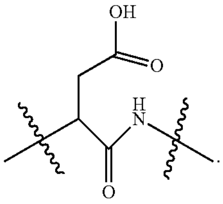.

In one embodiment, Lm1 is

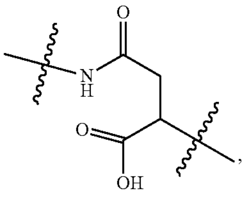,
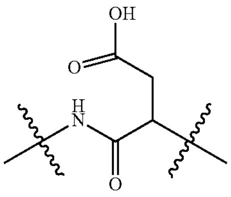

or a mixture thereof. In one embodiment, Lm2 is

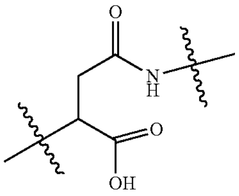,
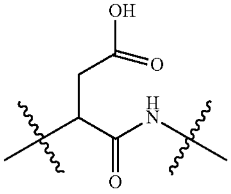

or a mixture thereof.

Specific Embodiment of the Formula (I') Compound

1. Formula (I') Compounds Wherein a and Lm Present

The linking unit of formula (I'-1), wherein p is 1, D1 is $G_n$, G is glycine, A2 is

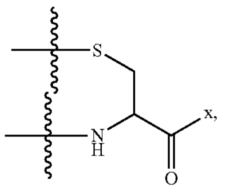

which is the remaining residue of

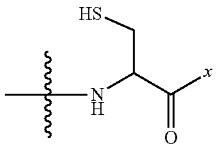

after the reaction of the thiol group with Lm2; and the structure of the compound of formula (I'-1) is as shown in the following formula (I'-1-1):

(I'-1-1)

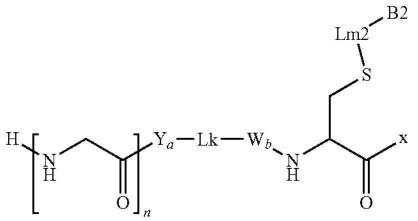

wherein n is an integer of 3 to 10, Lm2 is

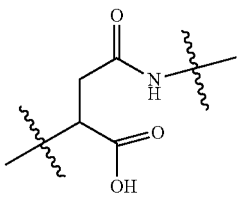
,
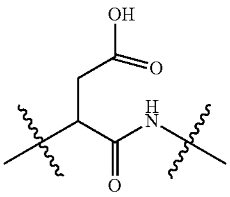

or a mixture thereof;

x is selected from hydrogen, OH, $NH_2$, an amino acid fragment comprising 1-10 amino acids, a nucleotide fragment comprising 1-10 nucleotides;

Y, Lk and W are as defined in formula (I'), respectively.

In a preferred embodiment, in formula (I'-1-1), x is selected from OH, $NH_2$ and Gly, especially $NH_2$.

In a particular embodiment, in formula (I'-1-1), a is 0, b is 0, n=3, Lk is $L^1$-$L^2$-$L^3$, $L^1$ is —NH—, $L^3$ is —C(O)—, $L^2$ is —$(C_2H_4—O)_i$—$C_2H_4$—, i=4, and x is $NH_2$, and the structure of the linking unit is as follows (linking unit LN102):

(LN102)

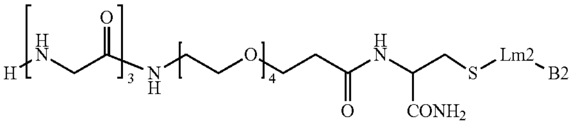

In one embodiment, in linking unit LN102, B2 is selected from the table below:

| |
|---|
| —$(CH_2)_k$C(O)—$R^7$ |
| —$(CH_2)_k$C(O)-Val-Cit-PABC |
| —$(CH_2)_k$C(O)-Val-Cit-PABC-(NH—$CR^1R^2$—C(O))$_d$—$R^7$ |
| —$(CH_2)_{k1}$C(O)—NH—$(C_2H_4—O)_i$—$(CH_2)_{k2}$C(O)-Lys-$R^7$ |
| —$(CH_2)_k$C(O)—NH—$(C_2H_4—O)_i$—H |
| —$(CH_2)_k$C(O)—(NH—$CR^1R^2$—C(O))$_d$—NH—$(C_2H_4—O)_i$—H |
| —$(CH_2)_k$C(O)—(NH—$CR^1R^2$—C(O))$_d$—$R^7$ |

In one embodiment, in linking unit LN102, B2 is selected from the table below:

| |
|---|
| —$(CH_2)_k$C(O)—$R^7$ |
| —$(CH_2)_k$C(O)-Val-Cit-PABC |
| —$(CH_2)_k$C(O)-Val-Cit-PABC-(NH—$CR^1R^2$—C(O))$_d$—$R^7$ |
| —$(CH_2)_{k1}$C(O)—NH—$(C_2H_4—O)_i$—$(CH_2)_{k2}$C(O)-Lys-$R^7$ |
| —$(CH_2)_k$C(O)—NH—$(C_2H_4—O)_i$—H |
| —$(CH_2)_k$C(O)—(NH—$CR^1R^2$—C(O))$_d$—$R^7$ |

In one embodiment, in linking unit LN102, Lm2 is

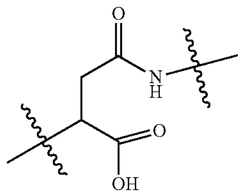
,
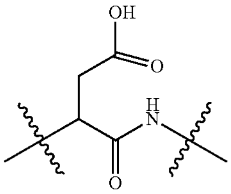

or a mixture thereof, B2 is —$(CH_2)_k$C(O)—$R^7$, k is 2, and the structure of the linking unit is a mixture of the following two structures (linking unit LN102-1):

(LN102-1)

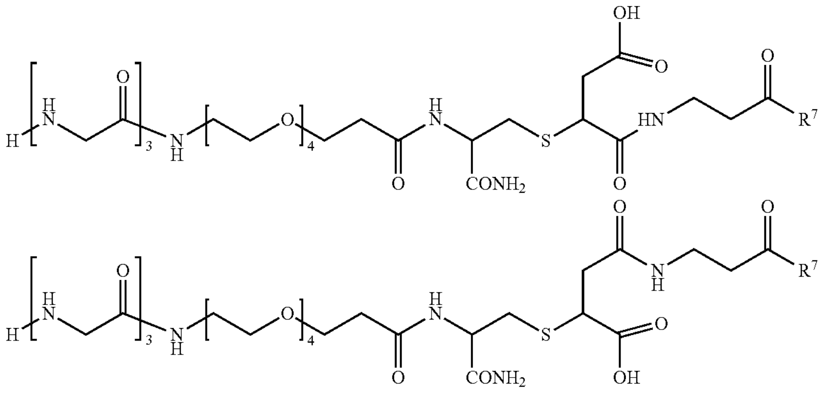

In one embodiment, in linking unit LN102, Lm2 is

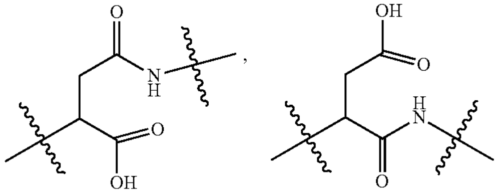 [SMILES: *NC(=O)CC(*)C(=O)O ; *NC(=O)C(*)CC(=O)O]

or a mixture thereof, B2 is —$(CH_2)_k$C(O)—$R^7$, k is 5, and the structure of the linking unit is a mixture of the following two structures (linking unit LN102-2):

(LN102-2)

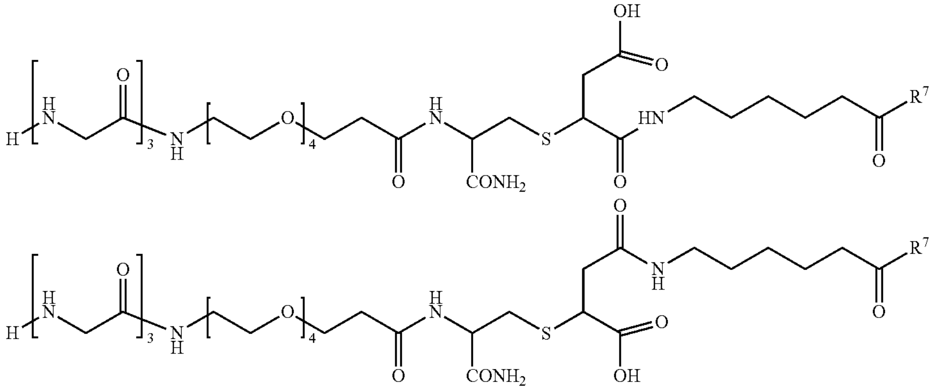

In one embodiment, in linking unit LN102, Lm2 is

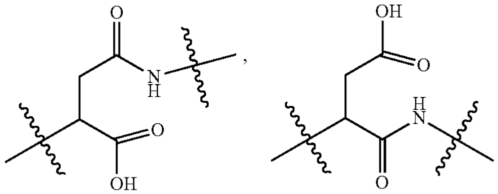 [SMILES: *NC(=O)CC(*)C(=O)O ; *NC(=O)C(*)CC(=O)O]

or a mixture thereof, B2 is —$(CH_2)_k$C(O)-Val-Cit-PABC, k is 5, and the structure of the linking unit is a mixture of the following two structures (linking unit LN102-3):

(LN102-3)
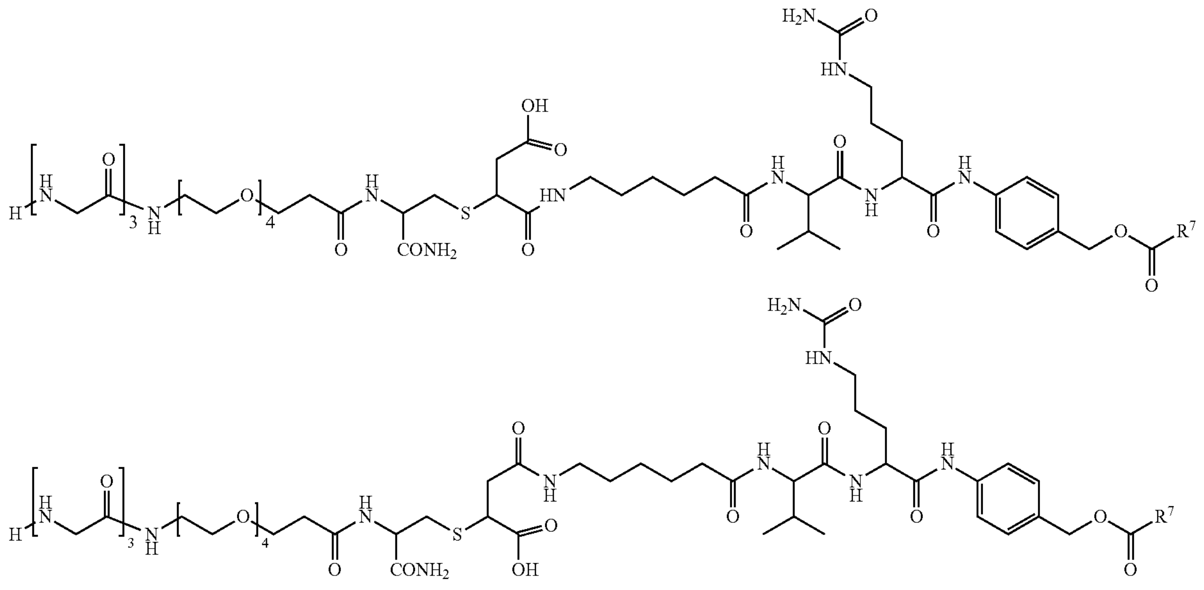
In one embodiment, in linking unit LN102, Lm2 is
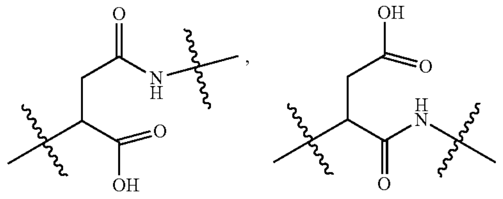 [SMILES: *NC(=O)CC(*)C(=O)O ; *NC(=O)C(*)CC(=O)O]
or a mixture thereof, B2 is $-(CH_2)_kC(O)$-Val-Cit-PABC—$(NH-CR^1R^2-C(O))_d-R^7$, k is 5, d is 1, $R^1$ and $R^2$ are hydrogen, and the structure of the linking unit is a mixture of the following two structures (linking unit LN102-4):
(LN102-4)
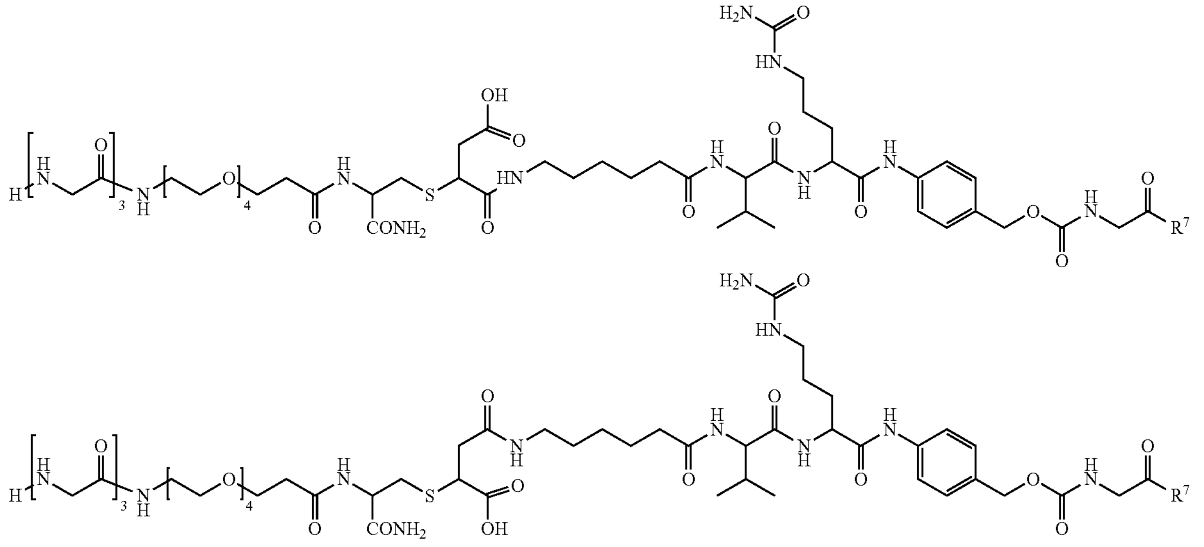

In one embodiment, in linking unit LN102, Lm2 is

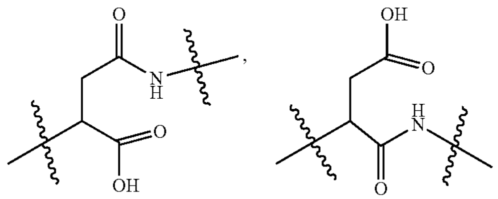 [SMILES: *NC(=O)CC(*)C(=O)O ; *NC(=O)C(*)CC(=O)O]

or a mixture thereof, B2 is —$(CH_2)_k$C(O)—NH—$(C_2H_4$—$O)_j$—H, k is 2, j is 1, and the structure of the linking unit is a mixture of the following two structures (linking unit LN102-6):

(LN102-6)

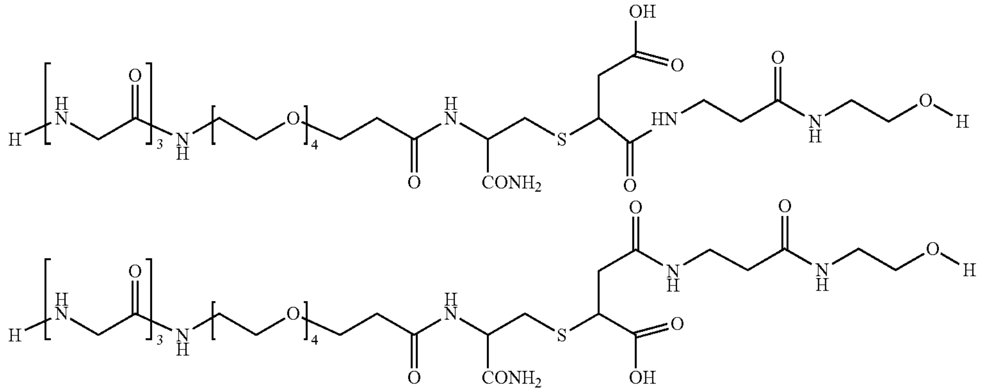

In one embodiment, in linking unit LN102, Lm2 is

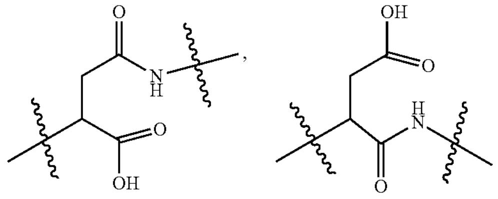 [SMILES: *NC(=O)CC(*)C(=O)O ; *NC(=O)C(*)CC(=O)O]

or a mixture thereof, B2 is —$(CH_2)_k$C(O)—(NH—$CR^1R^2$—$C(O))_d$—NH—$(C_2H_4$—$O)_j$—H, k is 2, d is 1, j is 1, $R^1$ and $R^2$ are methyl, and the structure of the linking unit is a mixture of the following two structures (linking unit LN102-7):

(LN102-7)

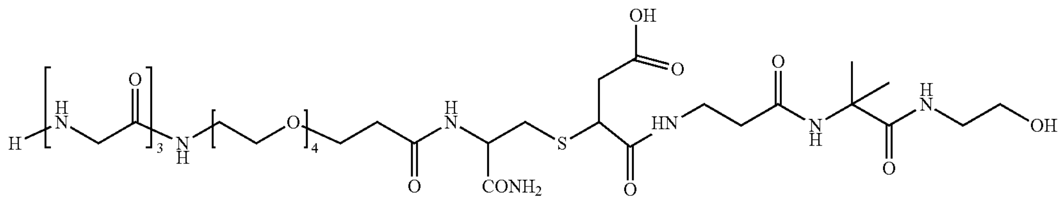

-continued

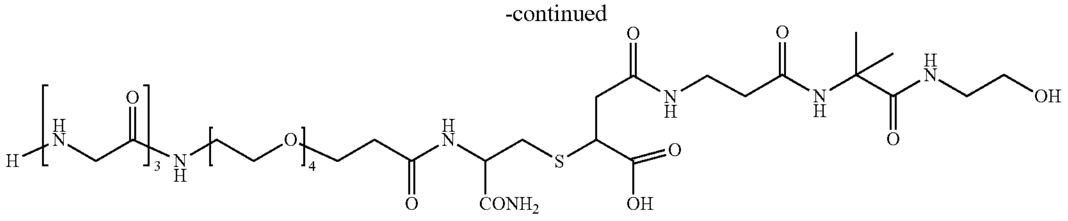

In one embodiment, in linking unit LN102, Lm2 is

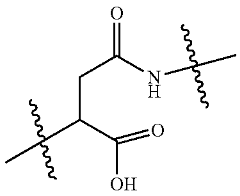

,

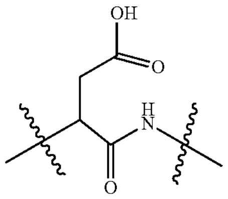

or a mixture thereof, B2 is —$(CH_2)_k$C(O)—(NH—$CR^1R^2$—C(O))$_d$—, k is 2, d is 1, $R^1$ and $R^2$ are hydrogen, and the structure of the linking unit is a mixture of the following two structures (linking unit LN102-8):

(LN102-8)

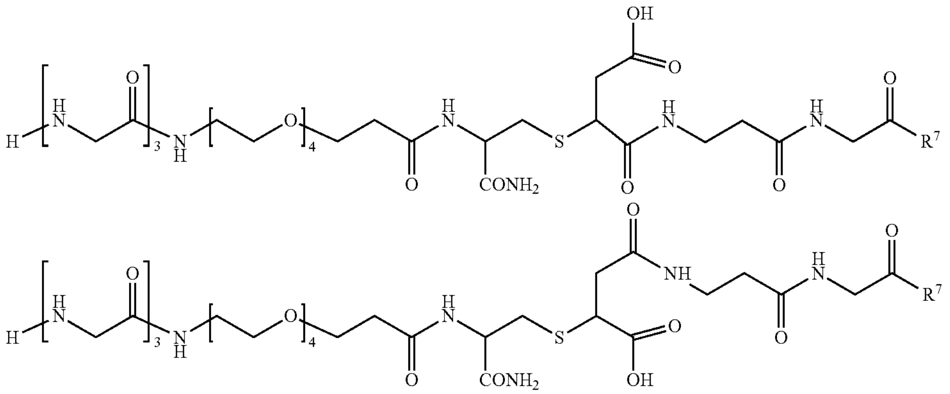

In one embodiment, in linking unit LN102, Lm2 is

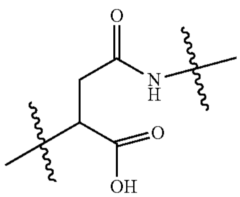

,

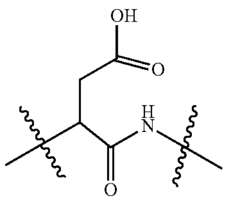

or a mixture thereof, B2 is —$(CH_2)_k$C(O)—(NH—$CR^1R^2$—C(O))$_d$—$R^7$, k is 2, d is 2, $R^1$ and $R^2$ are methyl, $R^{1'}$ and $R^{2'}$ are hydrogen, and the structure of the linking unit is a mixture of the following two structures (linking unit LN102-11):

(LN102-11)

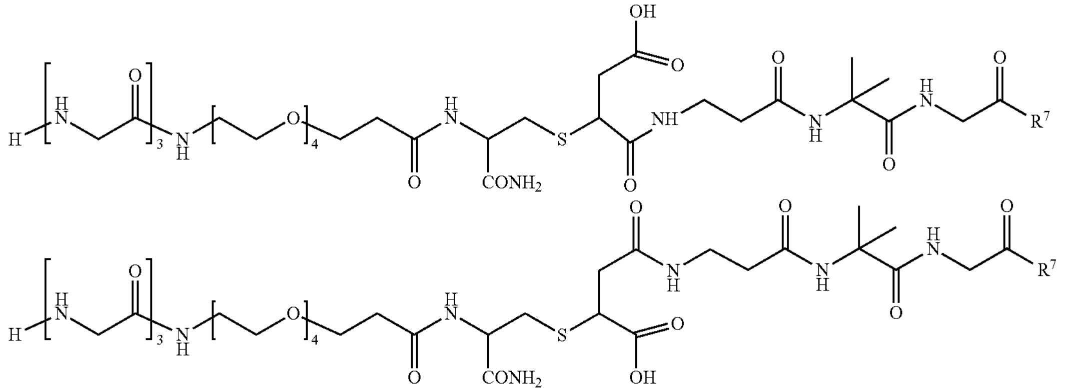

In a particular embodiment, in formula (I'-1-1), a is 0, b is 0, n=3, B2 is —Cys-$NH_2$, and the structure of the linking unit is as follows (linking unit LN105):

(LN105)

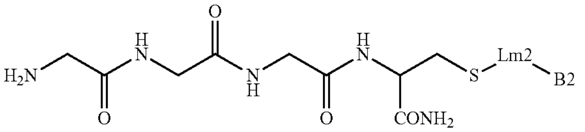

In a particular embodiment, in formula (I'-1-1), a is 0, b is 0, n=3, Lk is $L^1$-$L^2$-$L^3$, $L^1$ is —NH—, $L^3$ is —C(O)—, $L^2$ is —$(C_2H_4$—$O)_i$—$C_2H_4$—, i=4, x is OH, and the structure of the linking unit is as follows (linking unit LN106):

(LN106)

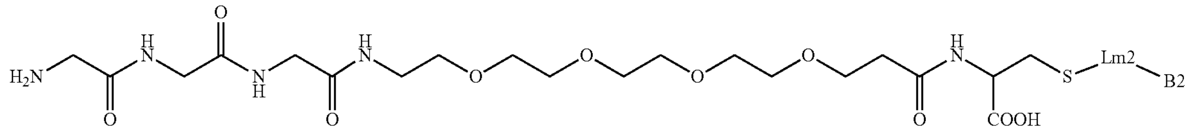

In a particular embodiment, in formula (I'-1-1), a is 1, b is 0, Y is L, L is leucine (Leu), n=3, Lk is $L^1$-$L^2$-$L^3$, $L^1$ is —NH—, $L^3$ is —C(O)—, $L^2$ is —$(C_2H_4$—$O)_i$—$C_2H_4$—, i=4, x is $NH_2$, and the structure of the linking unit is as follows (linking unit LN107):

(LN107)

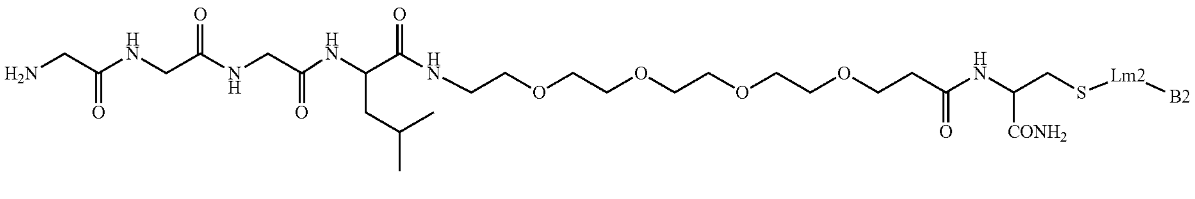

In yet a particular embodiment, in formula (I'-1-1), a is 1, b is 0, Y is Q, Q is glutamine (Gin), n=3, Lk is $L^1$-$L^2$-$L^3$, $L^1$ is —NH—, $L^3$ is —C(O)—, $L^2$ is —$(C_2H_4$—$O)_i$—$C_2H_4$—, i=4, x is $NH_2$, and the structure of the linking unit is as follows (linking unit LN108):

(LN108)

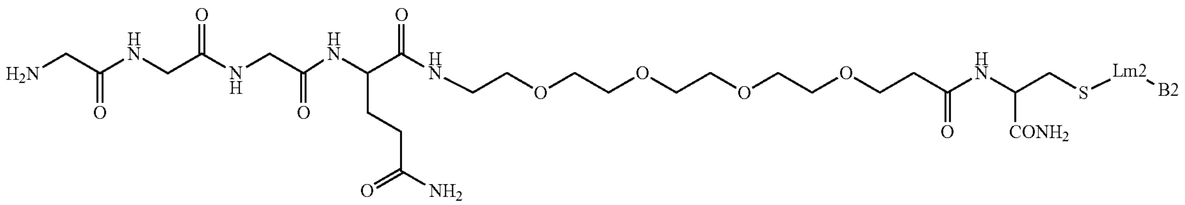

In a particular embodiment, in formula (I'-1-1), a is 0, b is 0, n=3, Lk is $L^1$-$L^2$-$L^3$, $L^1$ is —NH—, $L^3$ is —C(O)—, $L_2$ is —$C_5H_{10}$—, and the structure of the linking unit is as follows (linking unit LN109):

(LN109)

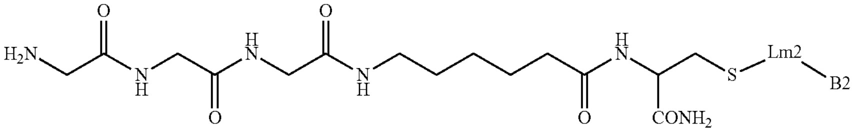

In yet a particular embodiment, in formula (I'-1-1), a is 0, b is 0, n=3, Lk is $L^1$-$L^2$-$L^3$, $L^1$ is —NH—, $L^3$ is —C(O)—, $L^2$ is —$C_5H_{10}$— group substituted with one —$NR^1R^2$ group, $R^1$ is hydrogen, $R^2$ is —C(O)$CH_3$, x is $NH_2$, and the structure of the linking unit is as follows (linking unit LN110):

(LN110)

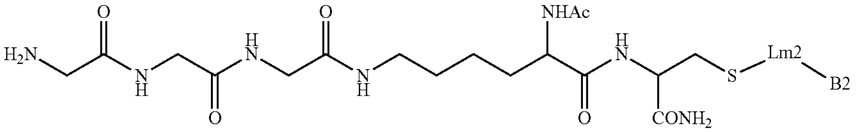

The linking unit of formula (I'-2), when D2 is LPXTG and A1 is

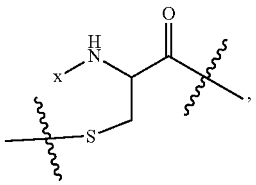

which is the remaining residue of

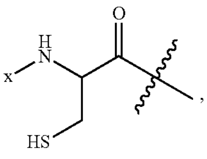

after the reaction of the thiol group with Lm2; the structure of the compound of formula (I'-2) is as shown in the following formula (I'-2-1):

(I'-2-1)

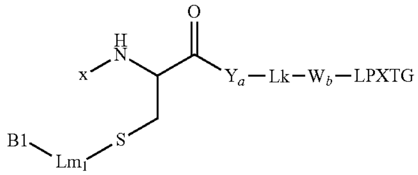

wherein x is selected from hydrogen, an amino acid fragment comprising 1-10 amino acids, a nucleotide fragment comprising 1-10 nucleotides, Lm1 is

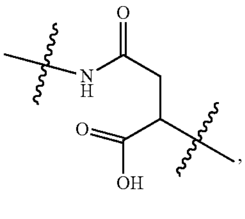

,

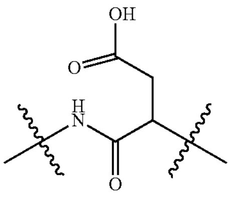

or a mixture thereof;

Y, Lk and W are as defined in formula (I'), respectively.

In one embodiment, x is hydrogen.

2. Formula (I') Compounds Wherein A and Lm are Absent

The linking unit of formula (I'-1), wherein p is 0, D1 is $G_n$, G is glycine; and the structure of the compound of formula (I'-1) is as shown in the following formula (I'-1-2):

(I'-1-2)

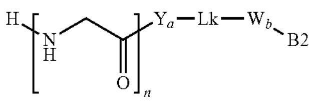

wherein n is an integer of 3 to 10;

Y, Lk, W, a and b are as defined in formula (I'), respectively.

In one embodiment, in formula (I'-1-2), a is 0, b is 0, n=3, B2 is -(Lys-$NH_2$), and the structure of the linking unit is as follows (linking unit LN201):

(LN201)

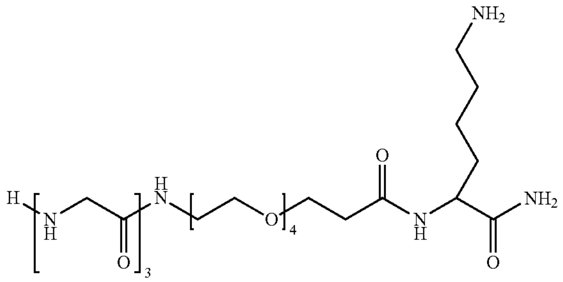

wherein n is an integer of 3 to 10.

In one embodiment, the compound of formula (I') is one of the compounds as shown in FIG. 1.

Compound of Formula (I') as Linking Unit

In one embodiment, the reactive group comprised by B1 or B2 can be used to covalently conjugate with a payload containing another reactive group, such that the compound of formula (I') bears a payload.

In another embodiment, the ligase recognition sequence comprised by D1 or D2 can be used in the conjugation by a ligase with the corresponding ligase recognition sequence. As the result, a compound of formula (I') can be linked to a molecule comprising a ligase recognition sequence, wherein the ligase recognition sequence comprised by the said molecule is a ligase donor/acceptor substrate recognition sequence corresponding to the ligase recognition sequence comprised by D1 or D2.

In one embodiment, the molecule comprises a recognition sequence of the ligase donor substrate, and correspondingly, D1 or D2 is independently a recognition sequence of the ligase acceptor substrate. In another embodiment, the molecule comprises a recognition sequence of the ligase acceptor substrate, and correspondingly, D1 or D2 is independently a recognition sequence of the ligase donor substrate.

Thus, a compound of formula (I') can be used as a linking unit that can be linked to a targeting molecule (such as an antibody or antigen-binding fragment thereof) and/or a payload. The linking unit may contain a ligase recognition sequence for conjugation of the linking unit with the targeting molecule. The linking unit may also contain a reactive group for covalent conjugation with the payload.

Depending on the type of terminal modification of the targeting molecule to be conjugated, the ligase recognition sequence comprised by the linking unit is a recognition sequence of the ligase acceptor substrate or a recognition sequence of the ligase donor substrate. The recognition sequences correspond to the ligase employed.

Depending on the type of reactive group of the payload to be conjugated, the reactive group comprised by the linking unit belongs to the type that can undergo condensation reaction therewith.

The linking unit may influence the properties of the drug conjugate formed thereby. For example, the linking unit can optionally be used to provide suitable hydrophilicity, and can optionally contain cleavage site(s) to achieve a suitable release profile of the payload.

In an alternative embodiment, the linking unit further comprises one or more non-enzymatic cleavage sites, each independently located at any suitable position. In one embodiment, the non-enzymatic cleavage site may be a hydrazone that is sensitive to pH. In another embodiment, the non-enzymatic cleavage site is a disulfide bond that is sensitive to reducing agents. In another alternative embodiment, the linking unit further comprises one or more enzymatic cleavage sites, each independently located at any suitable position beyond Y and W. In one embodiment, the enzymatic cleavage site is selected from an oligomeric peptide that is sensitive to protease, a cathepsin cleavage site, a glutaminase cleavage site, and the combination thereof.

In yet another alternative embodiment, to increase the DAR of the targeting molecule-drug conjugate, the linking unit may further comprise a branched structural fragment. The backbone of this branched structure is formed by multifunctional molecules according to a particular linking pattern, and the number and structure of the branches can be made to accommodate the desired number of payloads. Each of the branches may comprise the structure of the linear linking unit described above.

One skilled in the art can synthesize the linking units by conventional solid phase or liquid phase methods.

Payload-Bearing Formula (I') Compound

The reactive group comprised by B1 or B2 is covalently conjugated with a payload containing another reactive group to give a payload-bearing formula (I') compound.

In yet another aspect, provided is a compound having the structure of formula (II') (formula (II'-1) or formula (II'-2))

(Compound of formula (I'))-$PL_t$ (II'-1)

$PL_t$-(Compound of formula (I')) (II'-2)

wherein

PL is a Payload which is linked to the B1 or B2 moiety of the compound of formula (I');

t is an integer of 1 to 20.

t represents the number of PL(s) linked to the compound of formula (I').

In one embodiment, t is an integer of 1 to 10; e.g., 1, 2, 3, 4, 5, 6, 7, 8, 9, or 10.

In one embodiment, t is 1 and the compound of formula (II'-1) and (II'-2) respectively has the structure of the following formula (II'-1-1) or formula (II'-2-1):

D1-$Y_a$-Lk-$W_b$-$A2_p$-$Lm2_p$-B2-PL (II'-1-1)

PL-B1-$Lm1_p$-$A1_p$-$W_b$-Lk-$Y_a$-D2 (II'-2-1)

wherein, A1, A2, Lm1, Lm2, B1, B2, D1, D2, Y, Lk, W, a, b and p are as defined above, respectively.

In another embodiment, t is 2-20, the structure of the compound of formula (II') is as shown in any one of the following formula (II'-3) to formula (II'-6):

D1-$Y_a$-Lk-$W_b$-$A2_p$-$Lm2_p$-$(B2\text{-}PL)_t$ (II'-1-2)

D1-$Y_a$-Lk-$W_b$-$(A2_p\text{-}Lm2_p\text{-}B2\text{-}PL)_t$ (II'-1-3)

D1-$(Y_a\text{-}Lk\text{-}W_b\text{-}A2_p\text{-}Lm2_p\text{-}B2\text{-}PL)_t$ (II'-1-4)

$(PL\text{-}B1)_t$-$Lm1_p$-$A1_p$-$W_b$-Lk-$Y_a$-D2 (II'-2-2)

$(PL\text{-}B1\text{-}Lm1_p\text{-}A1_p)_t$-$W_b$-Lk-$Y_a$-D2 (II'-2-3)

$(PL\text{-}B1\text{-}Lm1_p\text{-}A1_p\text{-}W_b\text{-}Lk\text{-}Y_a)_t$-D2 (II'-2-4)

wherein, A1, A2, Lm1, Lm2, B1, B2, D1, D2, Y, Lk, W, a, b and p are as defined in formula (II'-1) or formula (II'-2), respectively.

Payload

In the present disclosure, the payload may be selected from small molecule compounds, nucleic acids and analogues, tracer molecules (including fluorescent molecules, etc.), short peptides, polypeptides, peptidomimetics, and proteins. In one embodiment, the payload is selected from small molecule compounds, nucleic acid molecules, and tracer molecules. In a preferred embodiment, the payload is selected from small molecule compounds. In a more preferred embodiment, the payload is selected from cytotoxin and fragments thereof. In a more preferred embodiment, the payload is selected from immune agonist and fragments thereof.

In one embodiment, the immune agonist is selected from TLR agonists and STING agonists, preferably TLR agonists such as TLR agonists (e.g., TLR 7 agonists, TLR 8 agonists, TLR 7/8 agonists) and STING agonists. In one embodiment, the immune agonist is selected from TLR agonists.

In one embodiment, the immune agonist is selected from imidazoquinolines. In one embodiment, the immune agonist has the structure of formula i:

Formula i

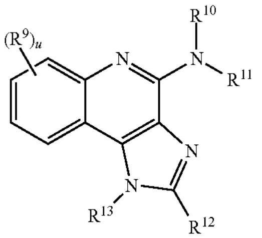

wherein each $R^9$ is independently selected from hydrogen, halogen, $C_{1-7}$ alkyl-OC(O)—$C_{1-7}$ alkyl, $C_{1-7}$ alkyl-OC(O)—$C_{2-7}$ alkenyl and 5-7 membered heterocycle;

$R^{10}$ and $R^{11}$ are each independently selected from hydrogen and $C_{1-7}$ alkyl;

$R^{12}$ is selected from $C_{1-7}$ alkyl and $C_{1-7}$ alkoxy-$C_{1-7}$ alkyl;

$R^{13}$ is selected from $C_{1-7}$ alkyl, which is optionally substituted by a substituent selected from —OH and —$NH_2$;

u is 1, 2, 3 or 4.

In one embodiment, the immune agonist is selected from compound i-1 to i-5:

i-1

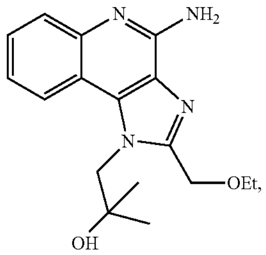

(Resiquimod)

i-2

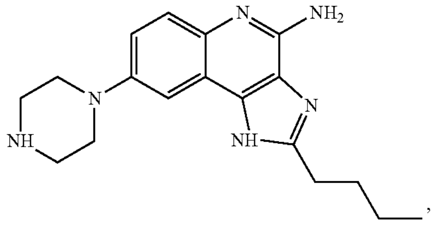

i-3

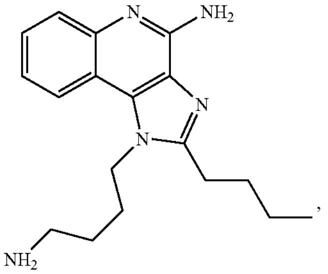

i-4

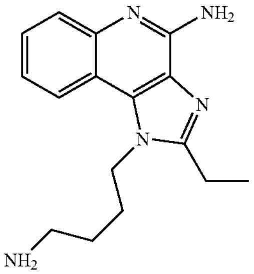

and i-5

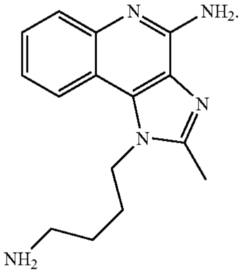

In one embodiment, the immune agonist is selected from 9H-purines. In one embodiment, the immune agonist has the structure of formula ii:

Formula ii

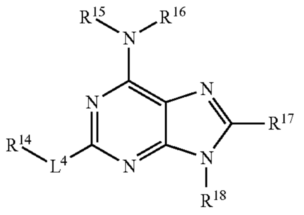

wherein $L^4$ is selected from —$CH_2$—, —NH—, —O—, —C(O)—;

$R^{14}$ is selected from $C_{1-7}$ alkyl, $C_{1-7}$ alkoxy and $C_{1-7}$ alkyl-OC(O)—$C_{1-7}$ alkyl;

$R^{15}$ and $R^{16}$ are each independently selected from hydrogen and $C_{1-7}$ alkyl;

$R^{17}$ is selected from —$NH_2$, —OH, $C_{1-7}$ alkyl, $C_{1-7}$ alkoxy and —NH—$C_{1-7}$ alkyl;

$R^{18}$ is selected from —$CH_2$-aryl, and —$CH_2$-heteroaryl, wherein the aryl and the heteroaryl are each independently optionally substituted by a substituent selected from —C(O)OH or

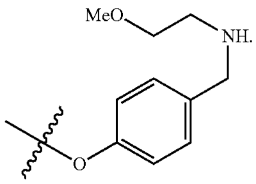 [SMILES: *Oc1ccc(CNCCOC)cc1]

In one embodiment, the immune agonist is selected from compound ii-1 and ii-2:

ii-1

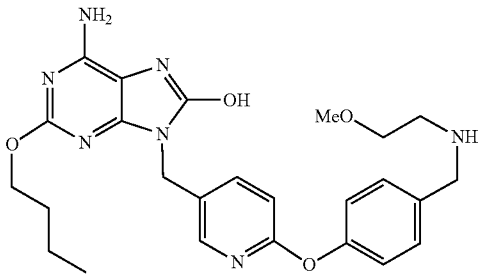

and ii-2

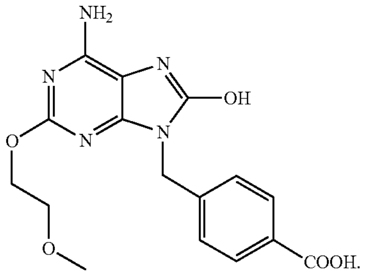

In one embodiment, the immune agonist is selected from 5H-pyrrolo[3,2-d]pyrimidines. In one embodiment, the immune agonist has the structure of formula iii:

Formula iii

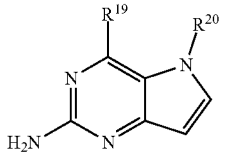

wherein $R^{19}$ is selected from —OH, —$NH_2$, $C_{1-7}$ alkyl, $C_{1-7}$ alkoxy and —NH—$C_{1-7}$ alkyl;

$R^{20}$ is selected from —$CH_2$-aryl, wherein the aryl is optionally substituted by two substituents selected from —OH, $C_{1-7}$ alkoxy and —$C_{1-7}$ alkyl-piperidinyl.

In one embodiment, the immune agonist is compound iii-1:

iii-1

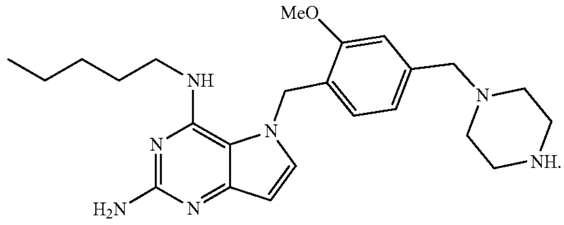

In one embodiment, the immune agonist is selected from 3H-benzo[b]azepines. In one embodiment, the immune agonist has the structure of formula iv:

Formula iv

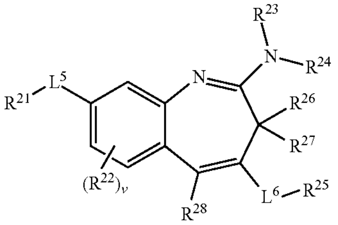

wherein $L^5$ is selected from —$CH_2$—, —NH—, —C(O)—, —NHC(O)— and —C(O)NH—;

$R^{21}$ is selected from

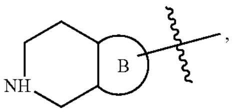

wherein B is a heteroaryl ring;

$R^{22}$ is selected from hydrogen and $C_{1-7}$ alkyl;

$R^{23}$ and $R^{24}$ are each independently selected from hydrogen and $C_{1-7}$ alkyl;

$L_6$ is selected from —$CH_2$— and —C(O)—;

$R^{25}$ is selected from —N($C_{1-7}$ alkyl)($C_{1-7}$ alkyl);

$R^{26}$, $R^{27}$ and $R^{28}$ are each independently selected from hydrogen and $C_{1-7}$ alkyl;

v is 1, 2 or 3.

In one embodiment, the immune agonist is compound iv-1:

iv-1

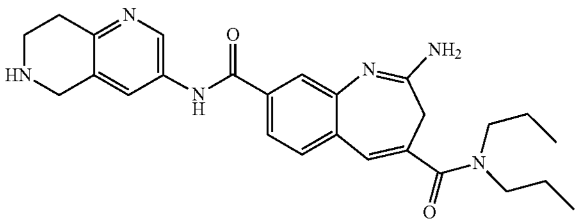

Preparation of the Payload-Bearing Formula (I') Compound

In one embodiment, the linking unit and the Payload are connected via reactive groups as defined above, using any reaction known in the art, including but not limit to condensation reaction, nucleophilic addition, electrophilic addition, etc.

Figure 2A:
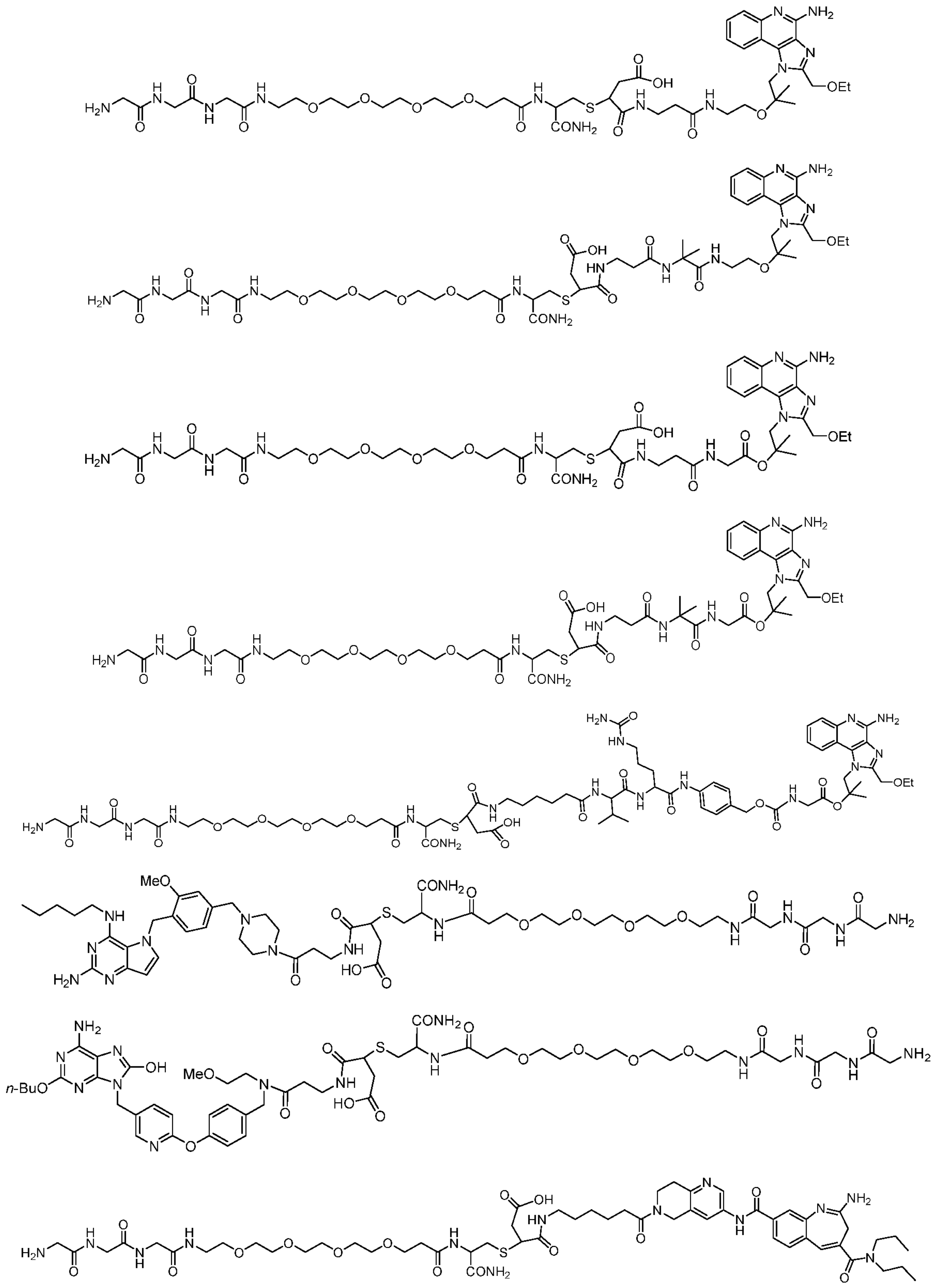
FIG. 2*a* and FIG. 2*b*: Illustrative examples of the compound of formula (II').
Figure 2B:
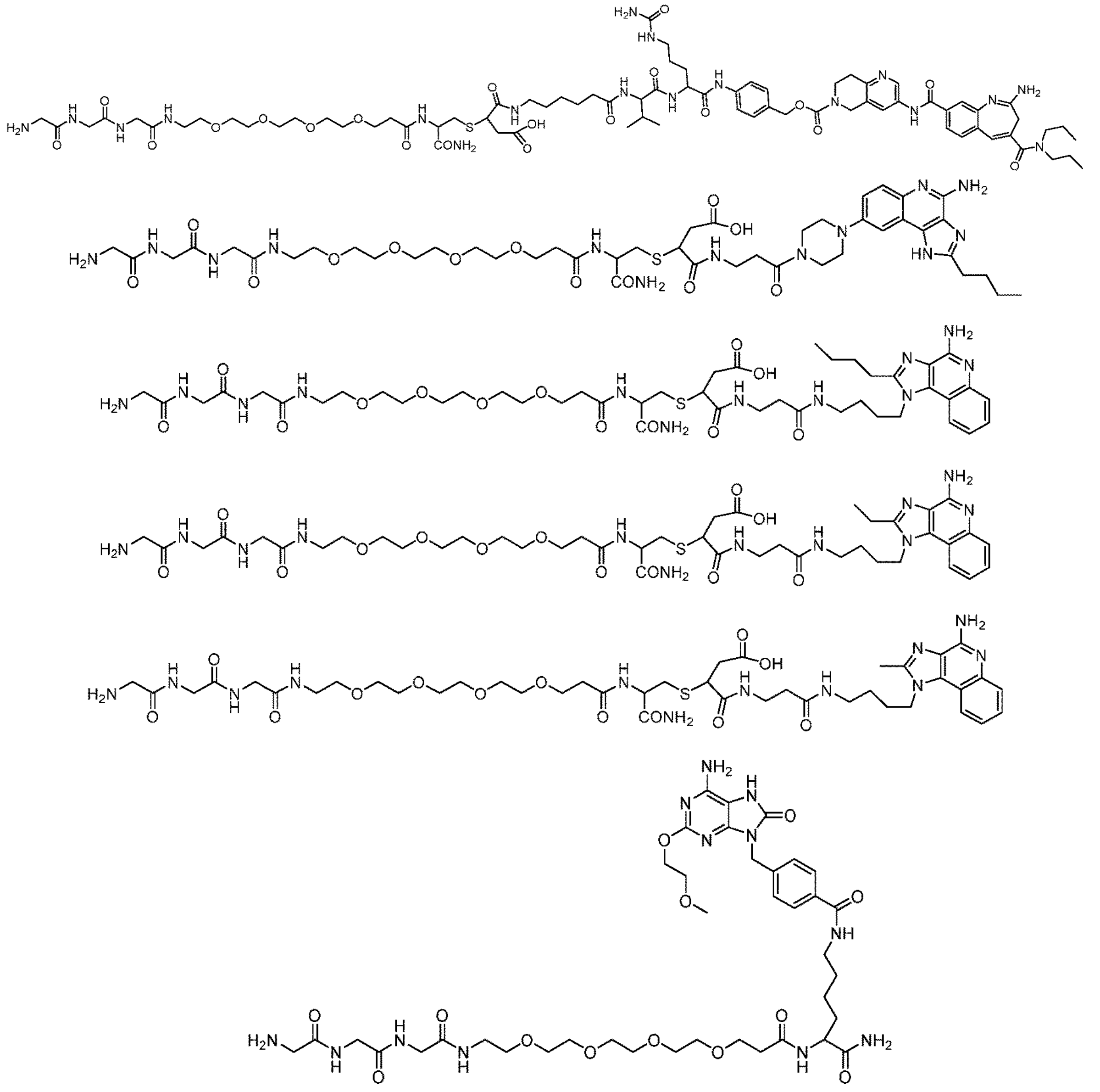

In one embodiment, the payload is an immune agonist, the antibody-immune agonist conjugate (numbered as LPx) is one of the compounds as shown in the following table and FIG. 2*a* and FIG. 2*b*.

| Compound of formula (II') | Linking unit | PL (immune agonist) |
|---|---|---|
| LP102-1-1 | LN102-1 | iii-1 |
| LP102-1-2 | LN102-1 | ii-1 |
| LP102-1-3 | LN102-1 | i-2 |
| LP102-1-4 | LN102-1 | i-3 |
| LP102-1-5 | LN102-1 | i-4 |
| LP102-1-6 | LN102-1 | i-5 |
| LP102-2-1 | LN102-2 | iv-1 |
| LP102-3-1 | LN102-3 | iv-1 |
| LP102-4-1 | LN102-4 | i-1 |
| LP102-6-1 | LN102-6 | i-1 |
| LP102-7-1 | LN102-7 | i-1 |
| LP102-8-1 | LN102-8 | i-1 |
| LP102-11-1 | LN102-11 | i-1 |
| LP201-1-1 | LN201 | ii-1 |

Compound of Formula (III')

In one aspect, provide is a compound of formula (III') (formula (III'-1) or formula (III'-2)):

(III'-1)

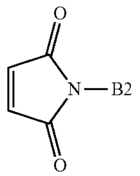

(III'-2)

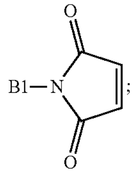

;

wherein B1 and B2 are as defined in formula (I').

In one embodiment, the compound of formula (III') could be used to prepare the payload-bearing formula (I') compound through the following route:

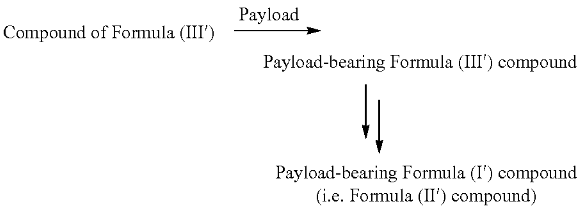

The transformation of Payload-bearing Formula (III') compound to Payload-bearing Formula (I') compound could be conducted using any known method in the art or as described herein. For example, single step or multi step synthesis could be conducted to introduce the structure fragment "D1-$Y_a$-Lk-$W_b$-$A2_p$" or "$A1_p$-$W_b$-Lk-$Y_a$-D2" to maleimide ring in the Payload-bearing Formula (III') compound, and then the resulting molecule which contains a succinimide moiety could undergo ring-opening reaction to open the succinimide ring and obtain the Payload-bearing Formula (I') compound (i.e. Formula (II') compound). In one embodiment, "D1-$Y_a$-Lk-$W_b$-$A2_p$" or "$A1_p$-$W_b$-Lk-$Y_a$-D2" is introduced to the Payload-bearing Formula (III') compound through the reaction of maleimide group contained in Formula (III') compound with a thiol group or amino group, and the thiol group or amino group is a part of the building block of "D1-$Y_a$-Lk-$W_b$-$A2_p$" or "$A1_p$-$W_b$-Lk-$Y_a$-D2". In one embodiment, the thiol group is contained by an optionally derivatized cystine. In one embodiment, the amino group is contained by an optionally derivatized lysine.

Figure 3:
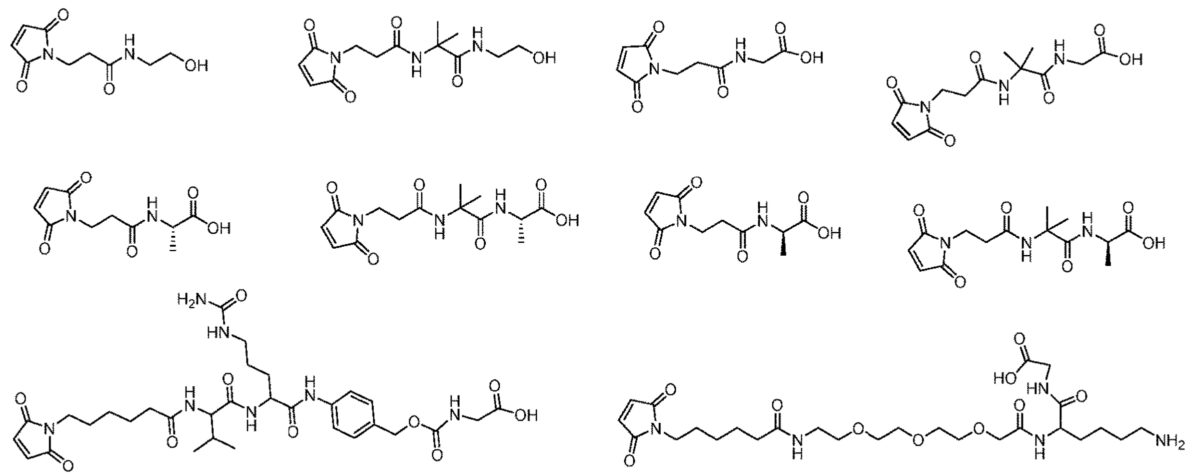
FIG. 3: Illustrative examples of the compound of formula (III').

In one embodiment, the compound of formula (III') is one of the compounds as shown in FIG. 3.

Conjugates and Preparation Thereof

Furthermore, the payload-bearing formula (I') compound which has the moiety comprising ligase recognition sequence can be conjugated with other molecules comprising a ligase recognition sequence, and can be thereby used in for example, the preparation of a targeting molecule-drug conjugate, such as an antibody-drug conjugate. Accordingly, in yet another aspect, provided is a conjugate which comprises a compound of formula (I'), a targeting molecule, and a payload.

Specific Constitution of the Conjugate

In yet another aspect, provided is a conjugate having the structure of formula (IV') (formula (IV'-1) or formula (IV'-2))

$$A\text{-}((\text{compound of formula (I')})\text{-}PL_t)_z \quad \text{(IV'-1)}$$

$$((\text{compound of formula (I')})\text{-}PL_t)_z\text{-}A \quad \text{(IV'-2)}$$

wherein

PL is a payload which is linked to the A1 or A2 moiety of the compound of formula (I');

A is a targeting molecule which is linked to the D1 or D2 moiety of the compound of formula (I');

z is an integer of 1 to 20;

t is an integer of 1 to 20.

t represents the number of PL(s) linked to the compound of formula (I').

In one embodiment, the payload is an immune agonist, which is as defined above. In one embodiment, the conjugate is an antibody-immune agonist conjugate.

In one embodiment, the ligase recognition sequence represented by D1 or D2 in the compound of formula (I') corresponds to the ligase recognition sequence in the targeting molecule which is to be conjugated therewith, and site-specific conjugation of the targeting molecule with the compound of formula (I') is thus realized. When the terminal modification of the targeting molecule to be conjugated is a terminal modification based on a recognition sequence of the ligase donor substrate, D1 or D2 is independently a recognition sequence of the ligase acceptor substrate. Alternatively, when the terminal modification of the targeting molecule to be conjugated is a terminal modification based on a recognition sequence of the ligase acceptor substrate, D1 or D2 is independently a recognition sequence of the ligase donor substrate.

In one embodiment, z is an integer of 1 to 10; e.g., 1, 2, 3, 4, 5, 6, 7, 8, 9, or 10.

In one embodiment, t is an integer of 1 to 10; e.g., 1, 2, 3, 4, 5, 6, 7, 8, 9, or 10.

In one embodiment, t is 1, conjugate of formula (IV') has the structure of the following formula (IV'-1-1) or formula (IV'-2-1):

$$A\text{-}(D1\text{-}Y_a\text{-}Lk\text{-}W_b\text{-}A2_p\text{-}Lm2_p\text{-}B2\text{-}PL)_z \quad (IV'\text{-}1\text{-}1)$$

$$(PL\text{-}B1\text{-}Lm1_p\text{-}A1_p\text{-}W_b\text{-}Lk\text{-}Y_a\text{-}D2)_z\text{-}A \quad (IV'\text{-}2\text{-}1)$$

wherein, PL, A1, A2, D1, D2, Y, W, Lk, a, b and p are as defined above, respectively.

In another embodiment, t is 2-20, conjugate of formula (IV') has the structure of any of the following formulae (IV'-1-2), (IV'-1-3), (IV'-1-4), (IV'-2-2), (IV'-2-3) and (IV'-2-4):

$$A\text{-}(D1\text{-}Y_a\text{-}Lk\text{-}W_b\text{-}A2_p\text{-}Lm2_p\text{-}(B2\text{-}PL)_t)_z \quad (IV'\text{-}1\text{-}2)$$

$$A\text{-}(D1\text{-}Y_a\text{-}Lk\text{-}W_b\text{-}(A2_p\text{-}Lm2_p\text{-}B2\text{-}PL)_t)_z \quad (IV'\text{-}1\text{-}3)$$

$$A\text{-}(D1\text{-}(Y_a\text{-}Lk\text{-}W_b\text{-}A2_p\text{-}Lm2_p\text{-}B2\text{-}PL)_t)_z \quad (IV'\text{-}1\text{-}4)$$

$$((PL\text{-}B1)_t\text{-}Lm1_p\text{-}A1_p\text{-}W_b\text{-}Lk\text{-}Y_a\text{-}D2)_z\text{-}A \quad (IV'\text{-}2\text{-}2)$$

$$((PL\text{-}B1\text{-}Lm1_p\text{-}A1_p)_t\text{-}W_b\text{-}Lk\text{-}Y_a\text{-}D2)_z\text{-}A \quad (IV'\text{-}2\text{-}3)$$

$$((PL\text{-}B1\text{-}Lm1_p\text{-}A1_p\text{-}W_b\text{-}Lk\text{-}Y_a)_t\text{-}D2)_z\text{-}A \quad (IV'\text{-}2\text{-}4)$$

wherein, PL, A1, A2, D1, D2, Y, W, Lk, a, b, p and z are as defined in formula (IV'-1-1) or formula (IV'-2-1), respectively.

Targeting Molecule

In one embodiment, the targeting molecule is an antibody or an antigen binding fragment thereof.

In some embodiments of the present disclosure, targets recognized by the targeting molecules (such as antibodies or antigen-binding fragments thereof) include but are not limited to CD19, CD22, CD25, CD30/TNFRSF8, CD33, CD37, CD44v6, CD56, CD70, CD71, CD74, CD79b, CD117/KIT, CD123, CD138, CD142, CD174, CD227/MUC1, CD352, CLDN18.2, DLL3, ErbB2/HER2, CN33, GPNMB, ENPP3, Nectin-4, EGFRvIII, SLC44A4/AGS-5, mesothelin, CEACAM5, PSMA, TIM1, LY6E, LIV1, Nectin4, SLITRK6, HGFR/cMet, SLAMF7/CS1, EGFR, BCMA, AXL, NaPi2B, GCC, STEAP1, MUC16, Mesothelin, ETBR, EphA2, 5T4, FOLR1, LAMP1, Cadherin 6, FGFR2, FGFR3, CA6, CanAg, Integrin αV, TDGF1, Ephrin A4, Trop2, PTK7, NOTCH3, C4.4A, FLT3, ROR1, ROR2, ROR1/2.

In one embodiment, the targeting molecule is an anti-human HER2 antibody or antigen binding fragment thereof. Examples of anti-human HER2 antibodies include but are not limited to Pertuzumab and Trastuzumab. Pertuzumab binds to the second extracellular domain (ECD2) of HER2 and is approved for the treatment of HER2-positive breast cancer. Trastuzumab binds to the fourth extracellular domain (ECD4) of HER2 and is approved for the treatment of Her2-positive breast cancer and gastric cancer.

In a preferred embodiment, the anti-human HER2 antibody is one or more selected from engineered anti-HER2 antibodies based on Trastuzumab.

In one embodiment, the targeting molecule is one or more selected from anti-human TROP2 antibodies or antigen-binding fragment thereof. In a particular embodiment, the anti-human TROP2 antibody is one or more selected from optionally engineered anti-TROP2 antibodies based on Ab0064.

In one embodiment, the targeting molecule is one or more selected from anti-human CLDN18.2 antibodies or antigen-binding fragment thereof. In a particular embodiment, the anti-human CLDN18.2 antibody is one or more selected from optionally engineered anti-CLDN18.2 antibodies based on Ab0098.

In a preferred embodiment, the anti-human HER2, TROP2 or CLDN18.2 antibody is a recombinant antibody selected from monoclonal antibody, chimeric antibody, humanized antibody, antibody fragment, and antibody mimic. In one embodiment, the antibody mimic is selected from scFv, minibody, diabody, nanobody. For the conjugation with the compound of formula (I'), the targeting molecule of the present disclosure may comprise a modified moiety to connect with D1 or D2 in the compound of formula (I'). The introduction position of such modified moiety is not limited, for example, when the targeting molecule is an antibody, its introduction position can be, but not limited to, located at the C-terminal or the N-terminal of the heavy chain or light chain of the antibody.

In an alternative embodiment, a modified moiety for the conjugation with D1 or D2 in the compound of formula (I') can be introduced at a non-terminal position of the heavy chain or light chain of the antibody using, for example, chemical modification methods.

In one embodiment, the targeting molecule of the present disclosure is an antibody or antigen-binding fragment thereof, which may comprise terminal modification. A terminal modification refers to a modification at the C-terminal or N-terminal of the heavy chain or light chain of the antibody, which for example comprises a ligase recognition sequence. In another embodiment, the terminal modification may further comprise spacer Sp3 comprising 2-100 amino acids, wherein the antibody, Sp3 and the ligase recognition sequence are sequentially linked. In a preferred embodiment, Sp3 is a spacer sequence containing 2-20 amino acids. In a particular embodiment, Sp3 is a spacer sequence selected from GA, GGGGS (SEQ ID NO: 25), GGGGSGGGGS (SEQ ID NO: 26) and GGGGSGGGGSGGGGS (SEQ ID NO: 27), especially GA.

In a preferred embodiment, the light chain of the antibody or antigen-binding fragment thereof includes 3 types: wild-type (LC); the C-terminus modified light chain (LCCT), which is modified by direct introduction of a ligase recognition sequence LPXTG and C-terminus modified light chain ($LCCT_L$), which is modified by introduction of short peptide spacers plus the ligase donor substrate recognition sequence LPXTG. The heavy chain of the antibody or antigen-binding fragment thereof includes 3 types: wild-type (HC); the C-terminus modified heavy chain (HCCT), which is modified by direct introduction of a ligase recognition sequence LPXTG; and C-terminus modified heavy chain ($HCCT_L$), which is modified by introduction of short peptide spacers plus the ligase donor substrate recognition sequence LPXTG. X can be any natural or non-natural single amino acid. When z in the compound of formula (IV') is 1 or 2, the combination of the above heavy and light chains can form 8 preferred antibody molecules, see the amino acid sequence table.

In a preferred embodiment, the light chain of the antibody or antigen-binding fragment thereof includes 3 types: wild-type (LC); the N-terminus modified light chain (LCNT), which is modified by direct introduction of a ligase recognition sequence GGG; and N-terminus modified light chain ($LCNT_L$), which is modified by introduction of short peptide spacers plus the ligase acceptor substrate recognition sequence GGG. The heavy chain of the antibody or antigen-binding fragment thereof includes 3 types: wild-type (HC); the N-terminus modified heavy chain (HCNT), which is modified by direct introduction of an ligase recognition sequence GGG; and N-terminus modified heavy chain ($HCNTL_t$), which is modified by introduction of short peptide spacers plus the ligase acceptor substrate recognition sequence GGG.

The conjugates of the present disclosure can further comprise a payload. The payload is as described above.

Specific Embodiments for the Conjugate

1. Formula (IV') Compounds Wherein a and Lm Present

The conjugate of formula (IV'-1-1), wherein p is 1, D1 is Gr G is glycine, A2 is

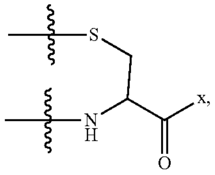

which is the remaining residue of

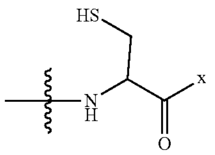

after the reaction of the thiol group with Lm2; and the structure of the compound of formula (IV'-1-1) is as shown in the following formula (denoted as formula IV'-1-1-1 or formula II):

(II)

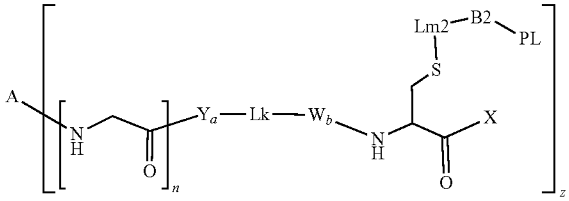

wherein n is an integer of 3 to 10, Lm2 is

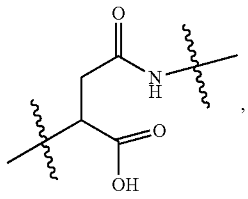

,

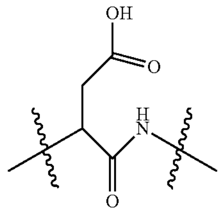

or a mixture thereof;

x is selected from hydrogen, OH, $NH_2$, an amino acid fragment comprising 1-10 amino acids, a nucleotide fragment comprising 1-10 nucleotides;

Y, Lk and W are as defined in formula (IV'), respectively.

In a preferred embodiment, in formula (II), x is selected from OH, $NH_2$ and Gly, especially $NH_2$.

In one embodiment, in formula (II), a is 0, b is 0, n=3, Lk is $L^1$-$L^2$-$L^3$, $L_1$ is —NH—, $L^3$ is —C(O)—, $L^2$ is —$(C_2H_4$—$O)_i$—$C_2H_4$—, i=4, and x is $NH_2$, and the structure of the compound of formula (II) is as shown in the following formula (II-1):

(II-1)

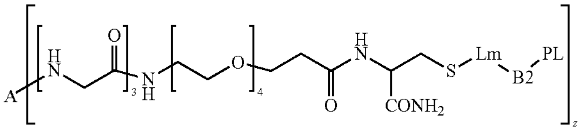

In one embodiment, in formula (II-1), B2 is selected from the table below:

| |
|---|
| —$(CH_2)_k$C(O)— |
| —$(CH_2)_k$C(O)-Val-Cit-PABC- |
| —$(CH_2)_k$C(O)-Val-Cit-PABC-(NH—$CR^1R^2$—C(O))$_d$— |
| —$(CH_2)_{k1}$C(O)—NH—$(C_2H_4$—O)$_i$—$(CH_2)$C(O)-Lys- |
| —$(CH_2)_k$C(O)—NH—$(C_2H_4$—O)$_i$— |
| —$(CH_2)_k$C(O)—(NH—$CR^1R^2$—C(O))$_d$—NH—$(C_2H_4$—O)$_i$— |
| —$(CH_2)_k$C(O)—(NH—$CR^1R^2$—C(O))$_d$— |

In one embodiment, in formula (II-1), B2 is selected from the table below:

| |
|---|
| —$(CH_2)_k$C(O)— |
| —$(CH_2)_k$C(O)-Val-Cit-PABC- |
| —$(CH_2)_k$C(O)-Val-Cit-PABC-(NH—$CR^1R^2$—C(O))$_d$— |
| —$(CH_2)_{k1}$C(O)—NH—$(C_2H_4$—O)$_i$—$(CH_2)_{k2}$C(O)-Lys- |
| —$(CH_2)_k$C(O)—NH—$(C_2H_4$—O)$_i$— |
| —$(CH_2)_k$C(O)—(NH—$CR^1R^2$—C(O))d— |

In one embodiment, in formula (II-1), Lm2 is
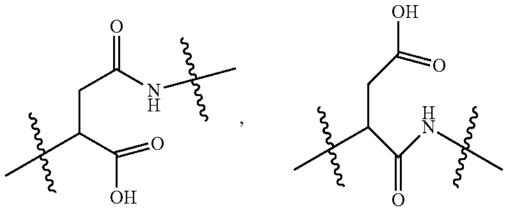 [SMILES: *NC(=O)CC(*)C(=O)O ; *NC(=O)C(*)CC(=O)O]
or a mixture thereof, B2 is $-(CH_2)_kC(O)-$, k is 2, and the structure of the conjugate is as follows (formula AC102-1):
(AC102-1)
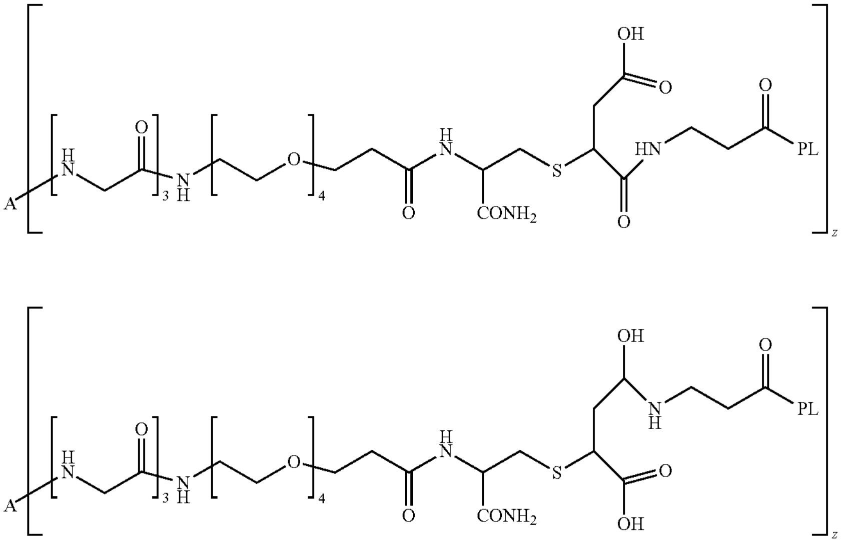
In one embodiment, in formula (II-1), Lm2 is
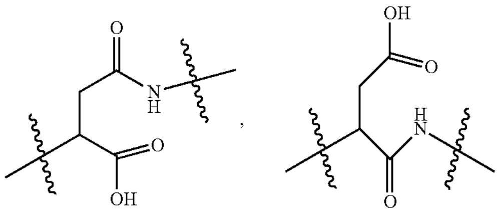 [SMILES: *NC(=O)CC(*)C(=O)O ; *NC(=O)C(*)CC(=O)O]
or a mixture thereof, B2 is $-(CH_2)_kC(O)-$, k is 5, and the structure of the conjugate is as follows (formula AC102-2):
(AC102-2)
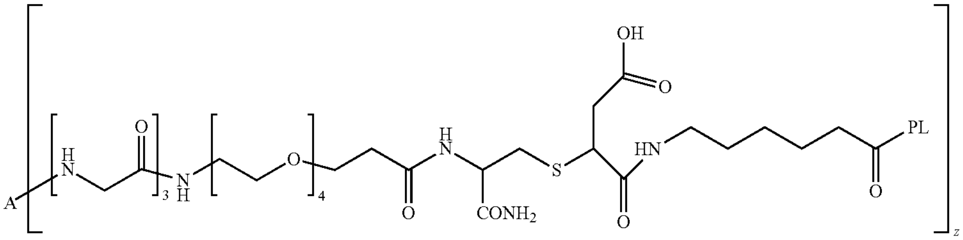

-continued
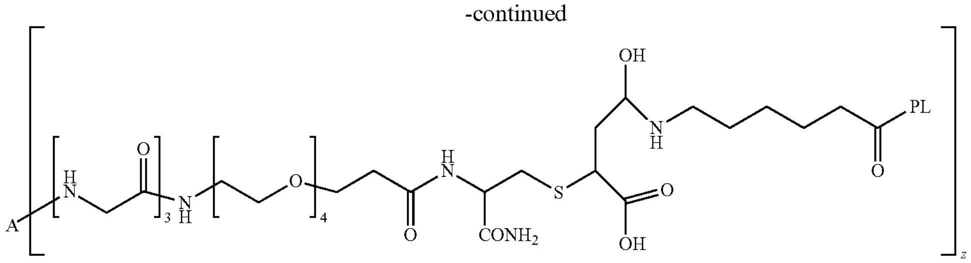
In one embodiment, in formula (II-1), Lm2 is
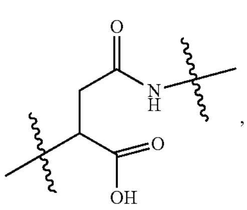
,
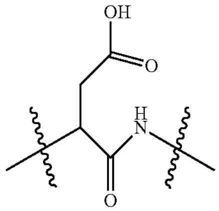
or a mixture thereof, B2 is —$(CH_2)_k$C(O)-Val-Cit-PABC—, k is 5, and the structure of the conjugate is as follows (formula AC102-3):
(AC102-3)
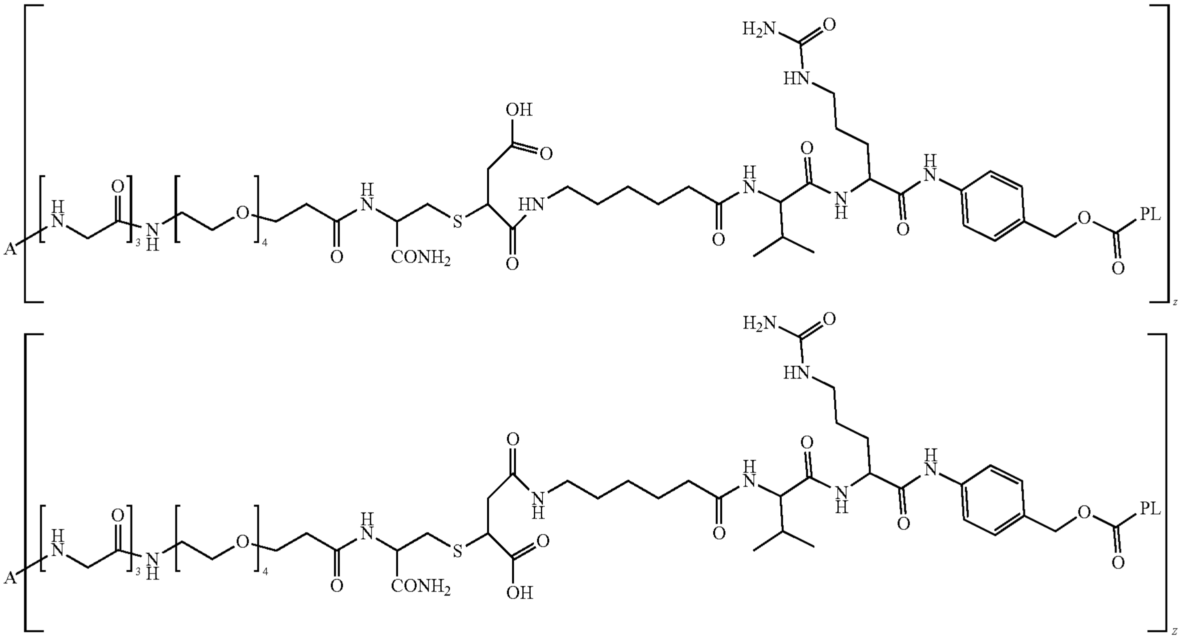
In one embodiment, in formula (II-1), Lm2 is
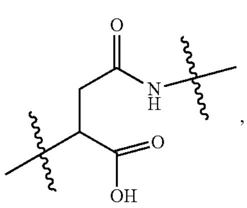
,
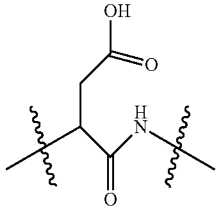

or a mixture thereof, B2 is $—(CH_2)_kC(O)$-Val-Cit-PABC—$(NH—CR^1R^2—C(O))_d—$, k is 5, d is 1, $R^1$ and $R^2$ are hydrogen, and the structure of the conjugate is as follows (formula AC102-4):
(AC102-4)
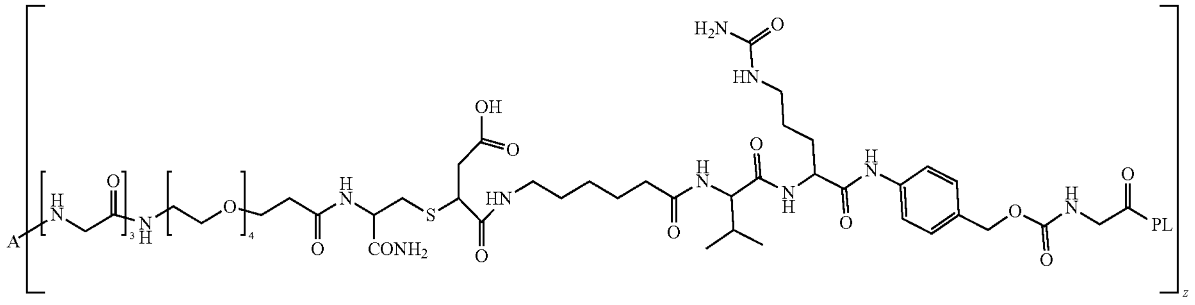
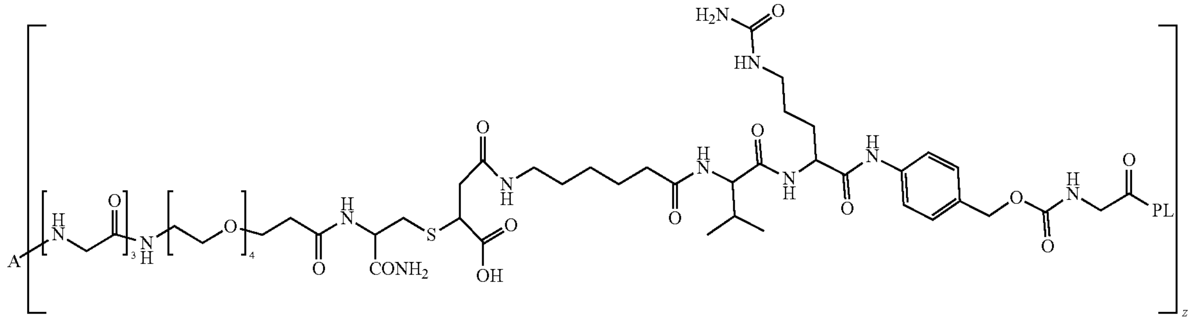
In one embodiment, in formula (II-1), Lm2 is
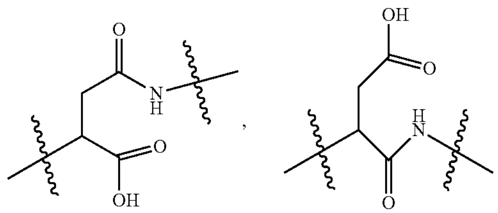 [SMILES: *NC(=O)CC(*)C(=O)O ; *NC(=O)C(*)CC(=O)O]
or a mixture thereof, B2 is $—(CH_2)_kC(O)—(NH—CR^1R^2—C(O))_d—NH—(C_2H_4—O)_j—$, k is 2, d is 1, j is 1, R' and $R^2$ are methyl, and the structure of the conjugate is as follows (formula AC102-7):
(AC102-7)
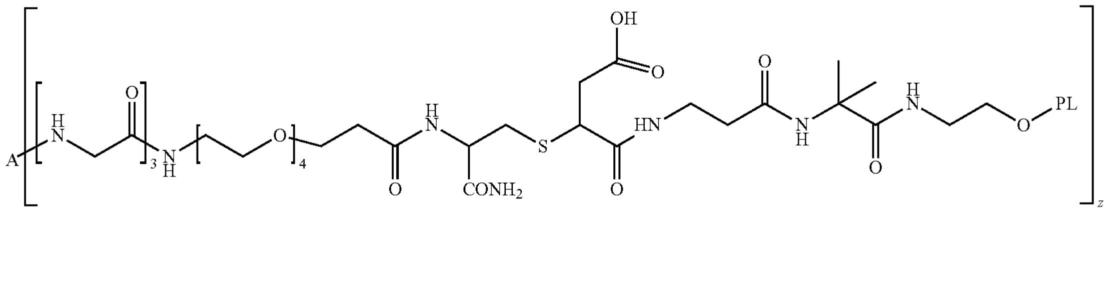

-continued

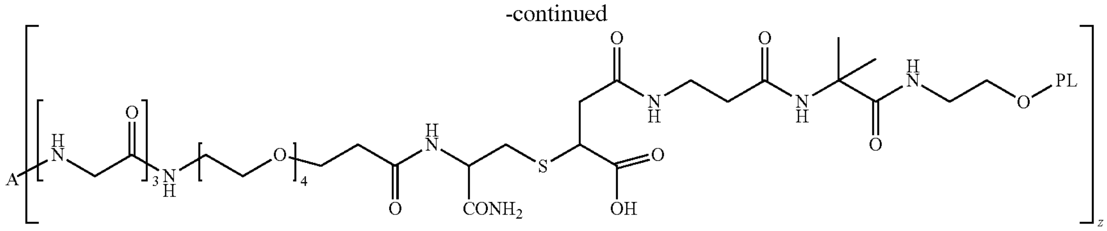

In one embodiment, in formula (II-1), Lm2 is

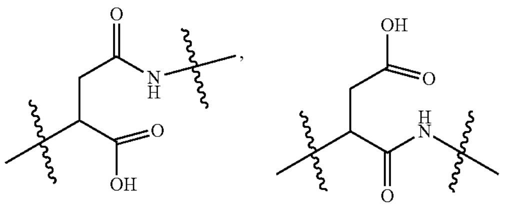 [SMILES: *NC(=O)CC(*)C(=O)O ; *NC(=O)C(*)CC(=O)O]

or a mixture thereof, B2 is $-(CH_2)_kC(O)-(NH-CR^1R^2-C(O))_d-$, k is 2, d is 1, $R^1$ and $R^2$ are hydrogen, and the structure of the conjugate is as follows (formula AC102-8):

(AC102-8)

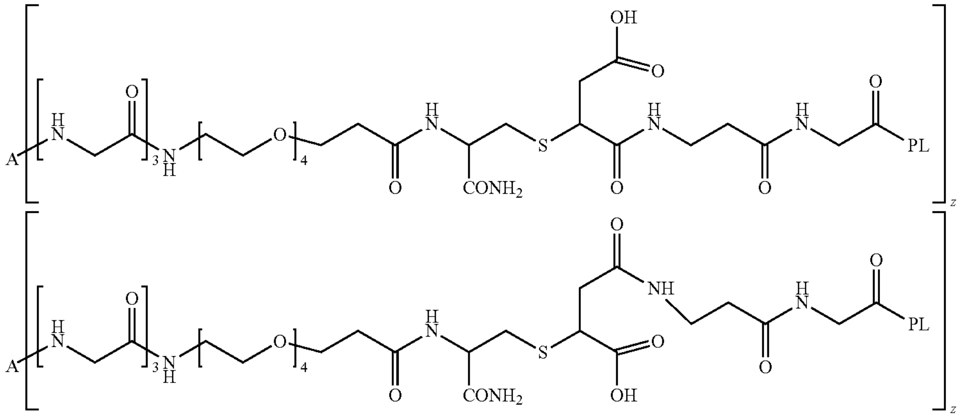

In one embodiment, in formula (II-1), Lm2 is

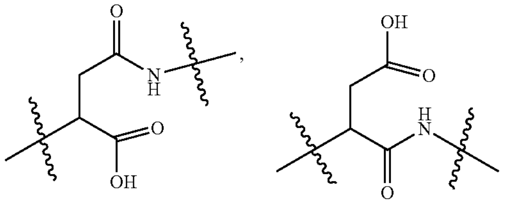 [SMILES: *NC(=O)CC(*)C(=O)O ; *NC(=O)C(*)CC(=O)O]

or a mixture thereof, B2 is $-(CH_2)_kC(O)-(NH-CR^1R^2-C(O))_d-$, k is 2, d is 2, $R^1$ and $R^2$ are methyl, $R^{1'}$ and $R^{2'}$ are hydrogen, and the structure of the conjugate is as follows (formula AC102-11):

(AC102-11)

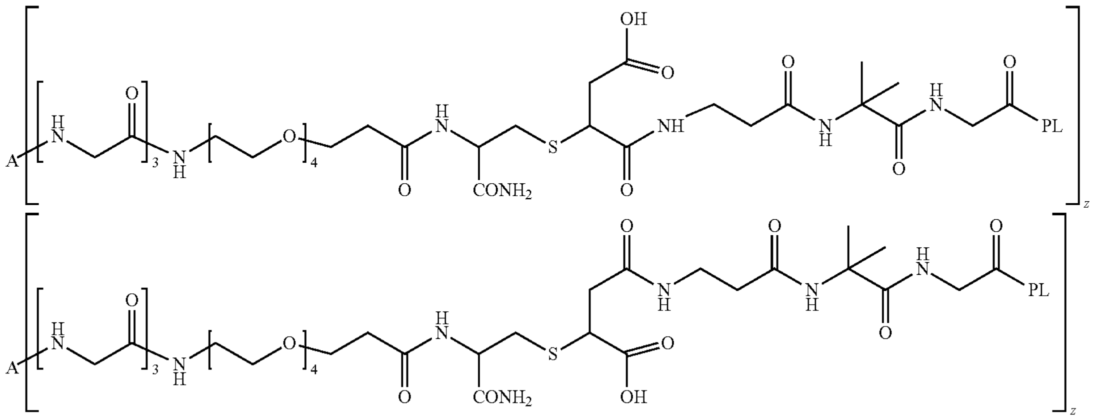

In a particular embodiment, in formula (II), a is 0, b is 0, n=3, B2 is —(Cys-$NH_2$)—, and the structure of the conjugate is as follows (formula AC105):

(AC105)

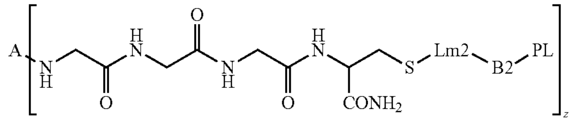

In a particular embodiment, in formula (II), a is 0, b is 0, n=3, Lk is $L^1$-$L^2$-$L^3$, $L^1$ is —NH—, $L^3$ is —C(O)—, $L_2$ is —$(C_2H_4—O)_i$—$C_2H_4$—, i=4, x is OH, and the structure of the conjugate is as follows (formula AC106):

(AC106)

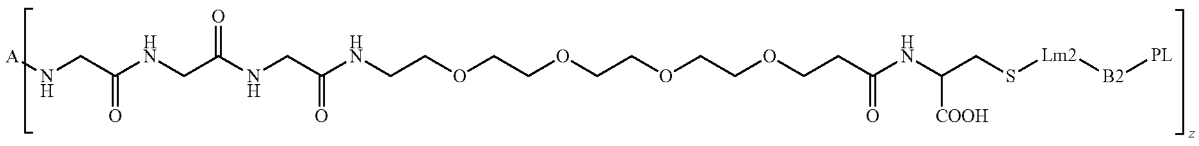

In a particular embodiment, in formula (II), a is 1, b is 0, Y is L, L is leucine (Leu), n=3, Lk is $L^1$-$L^2$-$L^3$, $L^1$ is —NH—, $L^3$ is —C(O)—, $L^2$ is —$(C_2H_4—O)_i$—$C_2H_4$—, i=4, x is $NH_2$, and the structure of the conjugate is as follows (formula AC107):

(AC107)

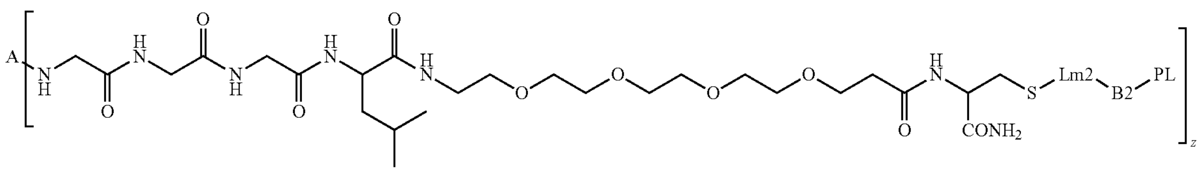

In yet a particular embodiment, in formula (II), a is 1, b is 0, Y is Q, Q is glutamine (Gln), n=3, Lk is $L^1$-$L^2$-$L^3$, $L^1$ is —NH—, $L^3$ is —C(O)—, $L^2$ is —$(C_2H_4$—$O)_i$—$C_2H_4$—, i=4, x is $NH_2$, and the structure of the conjugate is as follows (formula AC108):

(AC108)

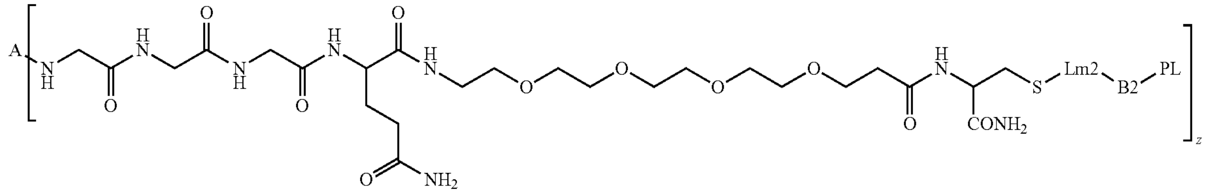

In a particular embodiment, in formula (II), a is 0, b is 0, n=3, Lk is $L^1$-$L^2$-$L^3$, $L^1$ is —NH—, $L^3$ is —C(O)—, $L^2$ is —$C_5H_{10}$—, and the structure of the conjugate is as follows (formula AC109):

(AC109)

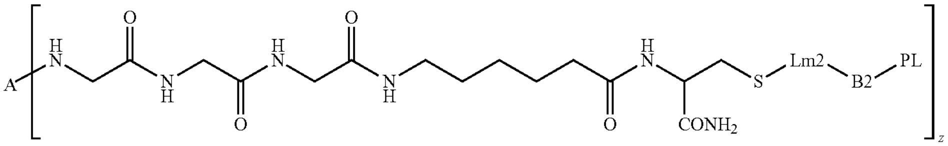

In yet a particular embodiment, in formula (II), a is 0, b is 0, n=3, Lk is $L^1$-$L^2$-$L^3$, $L^1$ is —NH—, $L^3$ is —C(O)—, $L^2$ is —$C_5H_{10}$— group substituted with one —$NR^1R^2$ group, $R^1$ is hydrogen, $R^2$ is —$C(O)CH_3$, x is $NH_2$, and the structure of the conjugate is as follows (formula AC110):

(AC110)

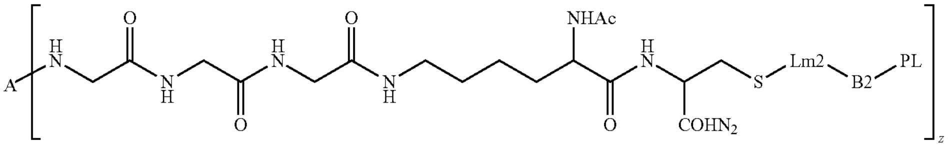

The conjugate of formula (IV'-2), when D2 is LPXTG and A1 is

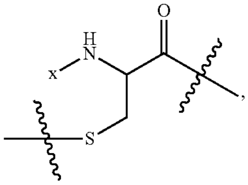

, which is the remaining residue of

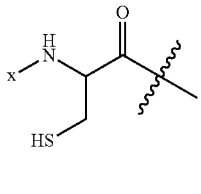

after the reaction of the thiol group with Lm2; the structure of the compound of formula (IV'-2-1) is as shown in the following formula (IV'-2-1-1):

(IV'-2-1-1)

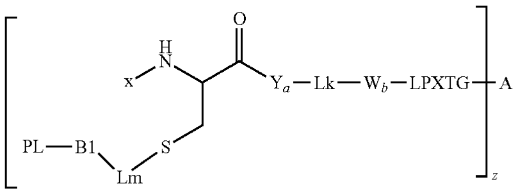

wherein x is selected from hydrogen, an amino acid fragment comprising 1-10 amino acids, a nucleotide fragment comprising 1-10 nucleotides, Lm1 is

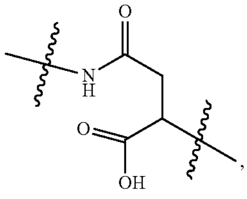
,
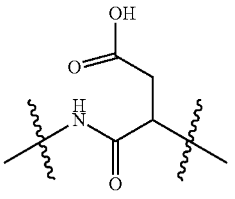

or a mixture thereof;

Y, Lk and W are as defined in formula (IV'), respectively.

In one embodiment, x is hydrogen.

2. Formula (IV') Compounds Wherein A and Lm are Absent

The linking unit of formula (IV'-1-1), wherein p is 0, D1 is $G_n$, G is glycine; and the structure of the compound of formula (IV'-1-1) is as shown in the following formula (IV'-1-1-2):

(IV'-1-1-2)

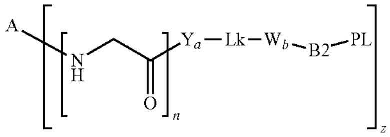

wherein n is an integer of 3 to 10;

Y, Lk, W, a and b are as defined in formula (IV'), respectively.

In one embodiment, in formula (IV'-1-1-2), a is 0, b is 0, n=3, Lk is $L^1$-$L^2$-$L^3$, $L^1$ is —NH—, $L^3$ is —C(O)—, $L^2$ is —$(C_2H_4$—$O)_i$—$C_2H_4$—, i=4, B2 is -(Lys-$NH_2$)—, and the structure of the conjugate is as follows (formula AC201):

(AC201)

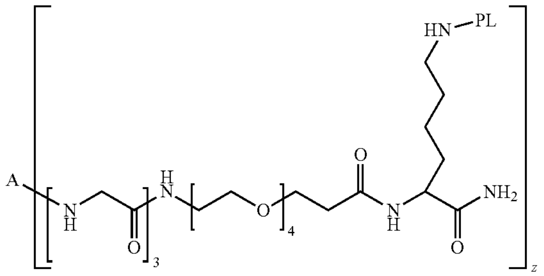

Preparation of the Conjugate

The conjugates of the present disclosure can be prepared by any method known in the art. In some embodiments, the conjugate is prepared by the ligase-catalyzed site-specific conjugation of a targeting molecule and a payload-bearing formula (I') compound, wherein the targeting molecule is modified by a ligase recognition sequence. The method comprises step A and step B.

Step A. Preparation of the Linking Unit-Payload Intermediate

In a preferred embodiment, B1 or B2 in the compound of formula (I') is each independently covalently linked via a reactive group to a payload containing a corresponding reactive group, wherein the reactive groups are respectively as defined above.

The linking unit-payload intermediate prepared using the compound of formula (I') of the present disclosure has defined structure, defined composition and high purity, so that when the conjugation reaction with an antibody is conducted, fewer impurities are introduced or no other impurities are introduced. When such an intermediate is used for the ligase-catalyzed site-specific conjugation with a modified antibody containing a ligase recognition sequence, a homogeneous ADC with highly controllable quality is obtained.

Step B. Linking the Targeting Molecule to the Payload-Bearing Formula (I') Compound The targeting molecule of the present disclosure can be conjugated with the payload-bearing formula (I') compound (i.e., the compound of formula (II')) by any method known in the art. For example, ligase-catalyzed site-specific conjugation technique is applied, and the targeting molecule and the payload-bearing formula (I') compound are linked to each other via the ligase-specific recognition sequences of the substrates. The recognition sequence depends on the particular ligase employed. In one embodiment, the targeting molecule is an antibody with recognition sequence-based terminal modifications introduced at the C-terminal of the light chain and/or the heavy chain, and the targeting molecule is conjugated with the compound of formula (II'), under the catalysis of the wild type or optimized engineered ligase or any combination thereof, and under suitable catalytic reaction conditions.

In a specific embodiment, the ligase is Sortase A and the conjugation reaction can be represented by the following scheme:

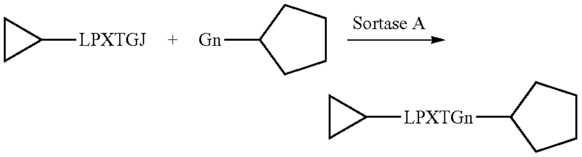

The triangle and pentagon respectively represent any of the following: a portion of an antibody or a portion of a compound of formula (II'), and the positions being interchangeable. n, X and J are respectively as defined above. When conjugated with Gr which is the corresponding recognition sequence of the acceptor substrate, the upstream peptide bond of the glycine in the LPXTGJ sequence is cleaved by Sortase A, and the resulting intermediate is linked to the free N-terminal of to generate a new peptide bond. The resulting amino acid sequence is LPXT$G_n$. The sequences and LPXTGJ are as defined above.

Table of Specific Conjugates

Figure 4A:
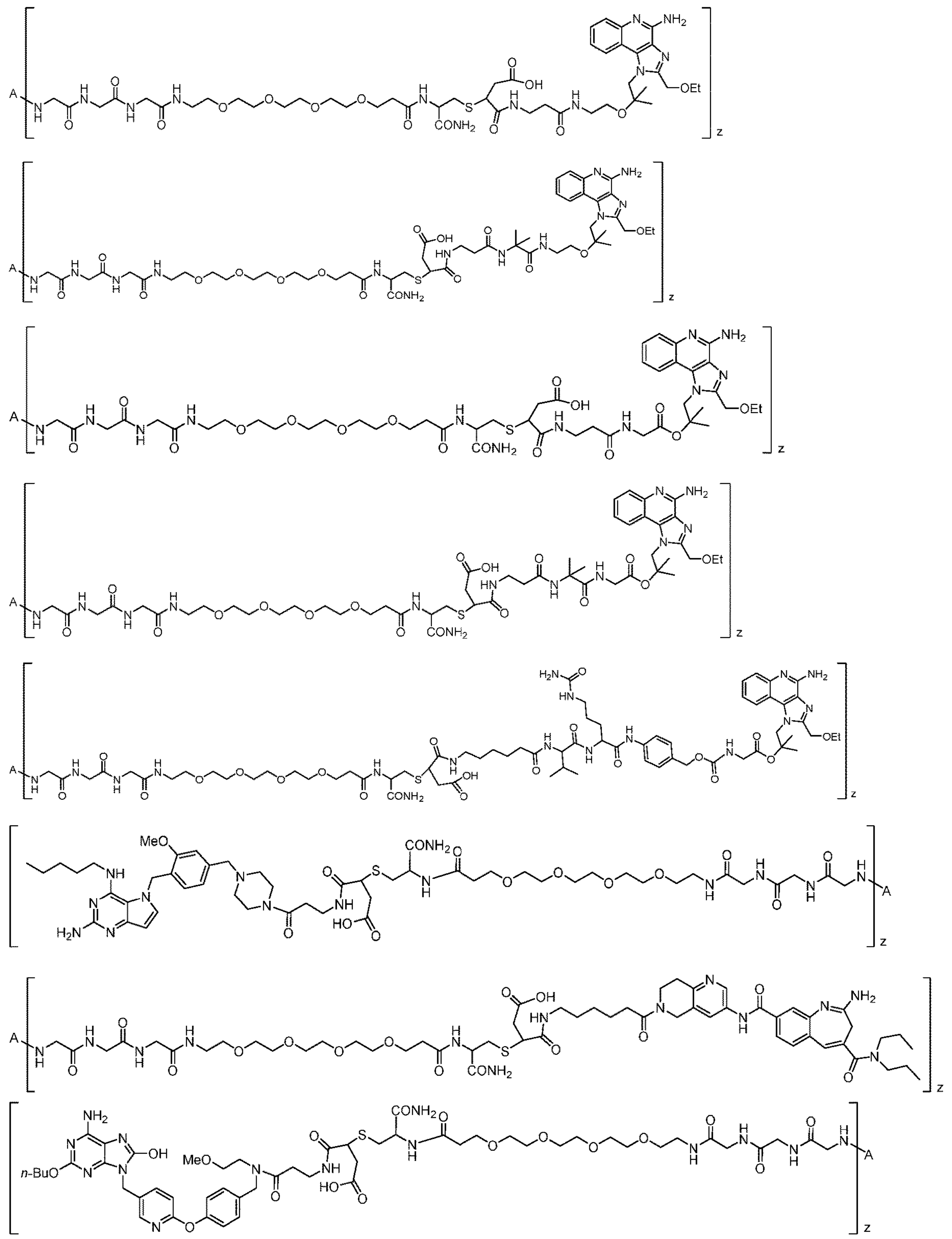
FIG. 4*a* and FIG. 4*b*: Illustrative examples of the compound of formula (IV').
Figure 4B:
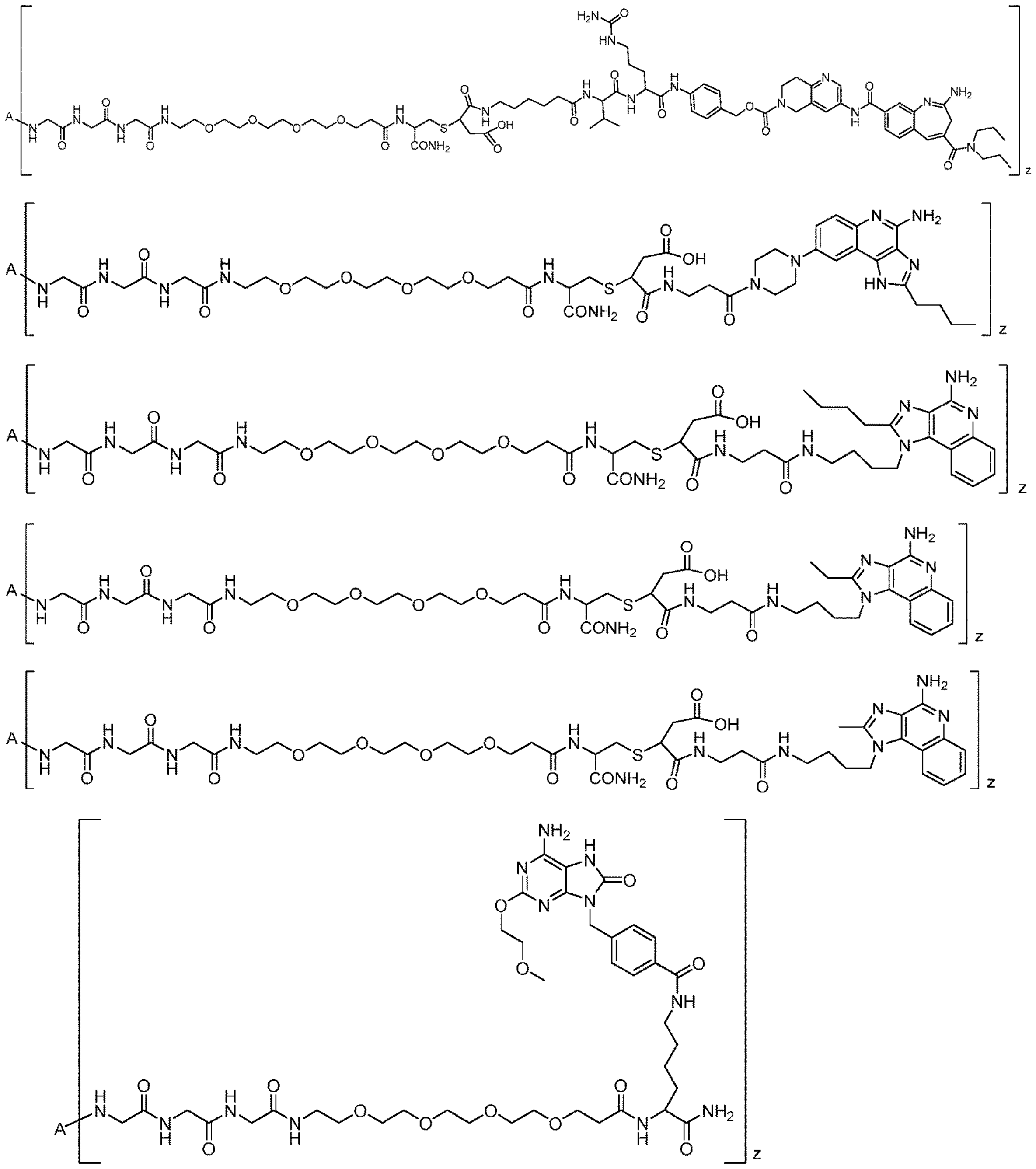

In one embodiment, the payload is an immune agonist. In one embodiment, the antibody is a modified Trastuzumab, preferably Ab0001-LCCT$_L$-HC (light chain SEQ ID NO: 1, heavy chain: SEQ ID NO: 2). The sequence of Ab0001-LCCT$_L$-HC is based on the amino acid sequence of Ab0001 (Trastuzumab), and GALPETGG was introduced at the C-terminal of the light chain, wherein LPETGG is the recognition sequence of the ligase donor substrate, and GA is a spacer sequence. In one embodiment, the antibody-immune agonist conjugate is as shown in the following table and FIG. 4 *a* and FIG. 4*b*.

| AIAC | Formula | PL (immune agonist) | A (targeting molecule) |
|---|---|---|---|
| AC102-1-1-1 | AC102-1 | iii-1 | Ab0001-LCCT$_L$-HC |
| AC102-1-1-2 | AC102-1 | ii-1 | Ab0001-LCCT$_L$-HC |
| AC102-1-1-3 | AC102-1 | i-2 | Ab0001-LCCT$_L$-HC |
| AC102-1-1-4 | AC102-1 | i-3 | Ab0001-LCCT$_L$-HC |
| AC102-1-1-5 | AC102-1 | i-4 | Ab0001-LCCT$_L$-HC |
| AC102-1-1-6 | AC102-1 | i-5 | Ab0001-LCCT$_L$-HC |
| AC102-2-1-1 | AC102-2 | iv-1 | Ab0001-LCCT$_L$-HC |
| AC102-3-1-1 | AC102-3 | iv-1 | Ab0001-LCCT$_L$-HC |
| AC102-4-1-1 | AC102-4 | i-1 | Ab0001-LCCT$_L$-HC |
| AC102-6-1-1 | AC102-6 | i-1 | Ab0001-LCCT$_L$-HC |
| AC102-7-1-1 | AC102-7 | i-1 | Ab0001-LCCT$_L$-HC |
| AC102-8-1-1 | AC102-8 | i-1 | Ab0001-LCCT$_L$-HC |
| AC102-11-1-1 | AC102-11 | i-1 | Ab0001-LCCT$_L$-HC |
| AC201-1-1-1 | AC201 | ii-1 | Ab0001-LCCT$_L$-HC |
| AC102-6-2-1 | AC102-6 | i-1 | Ab0064-LCCT$_L$-HC |
| AC102-8-2-1 | AC102-8 | i-1 | Ab0064-LCCT$_L$-HC |
| AC201-1-2-1 | AC201 | ii-1 | Ab0064-LCCT$_L$-HC |
| AC102-8-3-1 | AC102-8 | i-1 | Ab0098-LCCT$_L$-HC |
| AC201-1-3-1 | AC201 | ii-1 | Ab0098-LCCT$_L$-HC |

Pharmaceutical Composition and Pharmaceutical Preparation

Another object of the disclosure is to provide a pharmaceutical composition comprising a prophylactically or therapeutically effective amount of a conjugate of the present disclosure, and at least one pharmaceutically acceptable carrier.

The pharmaceutical composition of the present disclosure may be administered in any manner as long as it achieves the effect of preventing, alleviating, preventing or curing the symptoms of a human or animal. For example, various suitable dosage forms can be prepared according to the administration route, especially injections such as lyophilized powder for injection, injection, or sterile powder for injection.

The term "pharmaceutically acceptable" means that when contacted with tissues of the patient within the scope of normal medical judgment, no undue toxicity, irritation or allergic reaction, etc. shall arise, having reasonable advantage-disadvantage ratios and effective for the intended use.

The term pharmaceutically acceptable carrier refers to those carrier materials which are pharmaceutically acceptable and which do not interfere with the bioactivities and properties of the conjugate. Examples of aqueous carriers include but are not limited to buffered saline, and the like. The pharmaceutically acceptable carrier also includes carrier materials which brings the composition close to physiological conditions, such as pH adjusting agents, buffering agents, toxicity adjusting agents and the like, and sodium acetate, sodium chloride, potassium chloride, calcium chloride, sodium lactate, and the like.

In one embodiment, the pharmaceutical composition of the present disclosure has a drug to antibody ratio (DAR) of an integer or non-integer of 1 to 20, such as 1-10, 1-8, 1-6, 1-4, 1-3.5, 1-3, 1-2.5, preferably 1-2. In one embodiment, the pharmaceutical composition of the present disclosure has a DAR of about 1.5- about 2, preferably about 1.6- about 2, more preferably about 1.7- about 2.

Treatment Method and Use

The conjugates of the present disclosure are useful for the treatment of tumors and/or autoimmune diseases. Tumors susceptible to conjugate treatment include those characterized by specific tumor-associated antigens or cell surface receptors, and those will be recognized by the targeting molecule in the conjugate and can be affected by the immune cell activation activity of agonist in the conjugate.

Accordingly, in yet another aspect, also provided is use of a conjugate of the present disclosure or a pharmaceutical composition of the present disclosure in the manufacture of a medicament for treating a disease, disorder or condition selected from a tumor or an autoimmune disease.

In another aspect, provided is a conjugate of the present disclosure or a pharmaceutical composition of the present disclosure for use in the treatment of a tumor or an autoimmune disease.

In a further aspect, provided is a method of treating a tumor or an autoimmune disease, the method comprising administering to an individual in need thereof an effective amount of a conjugate of the present disclosure or a pharmaceutical composition of the present disclosure.

In a preferred embodiment, the conjugate of the present disclosure formed by conjugation of the anti-human HER2 antibody and the payload can specifically bind to HER2 on the surface of the tumor cell and selectively kill the HER2-expressing tumor cells. In another preferred embodiment, provided is use of a conjugate of the present disclosure or a pharmaceutical composition of the present disclosure in the manufacture of a medicament for treating a disease, disorder or condition selected from HER2-positive tumors. In a more preferred embodiment, the disease, disorder or condition is selected from breast cancer, gastric cancer, lung cancer, ovarian cancer, urothelial cancer, and the like.

In a preferred embodiment, the conjugate of the present disclosure formed by the conjugation of the anti-human TROP2 antibody and the payload can specifically bind to TROP2 on the surface of the tumor cell and selectively kill the TROP2-expressing tumor cells. In another preferred embodiment, provided is use of a conjugate of the present disclosure or a pharmaceutical composition of the present disclosure in the manufacture of a medicament for treating a disease, disorder or condition selected from a TROP2-positive tumors. In a more preferred embodiment, the disease, disorder or condition is selected from breast cancer, urothelial carcinoma, lung cancer, liver cancer, endometrial cancer, head and neck cancer, ovarian cancer, and the like.

In a preferred embodiment, the conjugate of the present disclosure formed by conjugation of the anti-human CLDN18.2 antibody and the payload can specifically bind to CLDN18.2 on the surface of the tumor cell and selectively kill the CLDN18.2-expressing tumor cells. In another preferred embodiment, provided is use of a conjugate of the present disclosure or a pharmaceutical composition of the present disclosure in the manufacture of a medicament for treating a disease, disorder or condition selected from CLDN18.2-positive tumors. In a more preferred embodiment, the disease, disorder or condition is selected from gastric cancer or pancreatic cancer, and the like.

The dosage of the conjugate administered to the subject can be adjusted to a considerable extent. The dosage can vary according to the particular route of administration and the needs of the subject, and can be subjected to the judgment of the health care professional.

Beneficial Effect

The present disclosure utilizes a linking unit with unique structure and uses a ligase to catalyze the conjugation of the targeting molecule and the agonist. The conjugate of the present disclosure has good homogeneity, high activity and high selectivity. In particular, the intracellular metabolites show significantly reduced cell proliferation toxicities to the cells with low expression or no expression of target antigens. Furthermore, the toxicity of the linking unit-agonist intermediate is much lower than that of the free agonist, and thus the manufacture process of the drug is less detrimental, which is advantageous for industrial production.

The conjugate of the present disclosure achieves at least one of the following technical effects:

(1) High inhibitory activity against target cells, or strong killing effect on target cells.
(2) Good physicochemical properties (e.g., solubility, physical and/or chemical stability).
(3) Good pharmacokinetic properties (e.g., good stability in plasma, appropriate half-life and duration of action).
(4) Good safety (low toxicity on non-target normal cells or tissues, and/or fewer side effects, wider treatment window), etc.

EXAMPLES

Preparation Example

In order to more clearly illustrate the objects and technical solutions, the present disclosure is further described below with reference to specific examples. It is to be understood that the examples are not intended to limit the scope of the disclosure. The specific experimental methods which were not mentioned in the following examples were carried out according to conventional experimental method.

Instruments, Materials and Reagents

Unless otherwise stated, the instruments and reagents used in the examples are commercially available. The reagents can be used directly without further purification.

MS: Thermo Fisher Q Exactive Plus, Water2795-Quattro micro triple quadrupole mass spectrometer HPLC: Waters 2695, Agilent 1100, Agilent 1200

Semi-preparative HPLC: Lisure HP plus 50D

Flow Cytometry: CytoFLEX S

HIC-HPLC: Butyl-HIC; mobile phase A: 25 mM PB, 2M $(NH_4)_2SO_4$, pH 7.0; mobile phase B: 25 mM PB, pH 7.0; flow rate: 0.8 ml/min; acquisition time: 25 min; injection amount: 20 μg; column temperature: 25° C.; detection wavelength: 280 nm; sample chamber temperature: 8° C.

SEC-HPLC: column: TSK-gel G3000 SWXL, TOSOH 7.8 mm ID×300 mm, 5 μm; mobile phase: 0.2 M $KH_2PO_4$, 0.25 M KCl, pH 6.2; flow rate: 0.5 ml/min; acquisition time: 30 min; injection volume: 50 μl; column temperature: 25° C.; detection wavelength; 280 nm; sample tray temperature: 8° C.

CHO was obtained from Thermo Fisher Scientific; pcDNA 3.3 was obtained from Life Technology; HEK293F was obtained from Prejin; PEIMAX transfection reagent was obtained from Polyscience; MabSelect Sure ProA was obtained from GE; Capto S ImpAct was obtained from GE; Rink-amide-MBNA-resin and dichloro resin were obtained from Nankai synthesis; HCC1954 was obtained from ATCC CAT #CRL-2338; SK-BR-3 was obtained from ATCC CAT #HTB-30; BT474 cells was obtained from ATCC CAT #HTB-20; JIMT1 cells was obtained from DSMZ CAT #ACC589; Colo205 cells was obtained from ATCC CAT #CRL-222; NCI-N87—Claudin 18.2 human gastric cancer cells was obtained from KYinno Biotechnology Co., Ltd; Claudin 18.2-negative NCI-N87 parental cells was obtained from ATCC CAT #CRL-5822; MC38hHER2 murine colorectal cancer cells was obtained from Biocytogen; NUGC4 human gastric cancer cells was obtained from JCRB CAT #JCRB0834; NCI-N87 cells (ATCC CAT #CRL-5822); MDA-MB-468 was obtained from ATCC CAT #HTB-132.

Example 1 Construction of Antibody Expression Vector, Antibody Expression, Purification and Identification 1.1 Production of the Modified Anti-Human HER2 Antibody Ab0001-LCCT$_L$-HC The expression plasmids for antibody Ab0001-LCCT$_L$-HC (light chain SEQ ID NO: 1, heavy chain: SEQ ID NO: 2) were constructed as follows. The sequence of the antibody Ab0001-LCCT$_L$-HC: based on the amino acid sequence of Trastuzumab, and GALPETGG was introduced at the C-terminal of the light chain, wherein LPETGG is the recognition sequence of the ligase donor substrate, and GA is a spacer sequence. The plasmids were transfected into CHO cells and the cell population was established and screened for a highly expressed cell population, which was cultured with reference to the culture process of Trastuzumab in a 5-10 L reactor, and the supernatant was collected.

1.2 The Purification of Antibody Ab0001-LCCT$_L$-HC

The purification of Ab0001-LCCT$_L$-HC was carried out in a standard process using the combination of MabSelect affinity chromatography and Sepharose S cation exchange chromatography, the purified products were dissolved in the original Trastuzumab drug buffer (5 mM histidine-HCl, 2% Trehalose, 0.009% Polysorbate 20, PH 6.0), and frozen in small aliquots.

1.3 The Quality Control of Antibody Ab0001-LCCT$_L$-HC

The purity of the above purified antibody Ab0001-LCCT$_L$-HC is 98.5% by SDS-PAGE; the content of high molecular weight polymer of the sample is less than 0.4% by SEC-HPLC; endotoxin content is less than 0.098 EU/mg.

1.4 Preparation of Other Modified Anti-Human Antibodies

According to a similar method, a terminal modification based on the ligase recognition sequence was introduced at the C-terminal of the light and/or heavy chain of the Trastuzumab, respectively, giving a modified antibody.

The modified anti-human HER2 antibodies based on Ab0001 (Trastuzumab) are listed in Table 1. LPETGG in the terminal modification sequence is a recognition sequence of the ligase donor substrate, and GA is a spacer sequence.

TABLE 1

| Modified anti-human HER2 antibodies | | |
|---|---|---|
| | Sequence | Sequence introduced at the terminal |
| Ab0001-LCCT$_L$-HC light chain | SEQ ID NO: 1 | GALPETGG (SEQ ID NO: 28) |
| Ab0001-LCCT$_L$-HC heavy chain | SEQ ID NO: 2 | —* |
| Ab0001-LC-HCCT light chain | SEQ ID NO: 3 | — |
| Ab0001-LC-HCCT heavy chain | SEQ ID NO: 4 | LPETGG (SEQ ID NO: 29) |
| Ab0001-LC-HCCT$_L$ light chain | SEQ ID NO: 5 | — |
| Ab0001-LC-HCCT$_L$ heavy chain | SEQ ID NO: 6 | GALPETGG (SEQ ID NO: 28) |
| Ab0001-LCCT-HC light chain | SEQ ID NO: 7 | LPETGG (SEQ ID NO: 29) |
| Ab0001-LCCT-HC heavy chain | SEQ ID NO: 8 | — |
| Ab0001-LCCT-HCCT light chain | SEQ ID NO: 9 | LPETGG (SEQ ID NO: 29) |
| Ab0001-LCCT-HCCT heavy chain | SEQ ID NO: 10 | LPETGG (SEQ ID NO: 29) |
| Ab0001-LCCT-HCCT$_L$ light chain | SEQ ID NO: 11 | LPETGG (SEQ ID NO: 29) |
| Ab0001-LCCT-HCCT$_L$ heavy chain | SEQ ID NO: 12 | GALPETGG (SEQ ID NO: 28) |
| Ab0001-LCCT-HCCT light chain | SEQ ID NO: 13 | GALPETGG (SEQ ID NO: 28) |
| Ab0001-LCCT-HCCT heavy chain | SEQ ID NO: 14 | LPETGG (SEQ ID NO: 29) |
| Ab0001-LCCTL-HCCT$_L$ light chain | SEQ ID NO: 15 | GALPETGG (SEQ ID NO: 28) |
| Ab0001-LCCTL-HCCT$_L$ heavy chain | SEQ ID NO: 16 | GALPETGG (SEQ ID NO: 28) |

*— indicates no terminal modification

The modified anti-human TROP2 antibody Ab0064-LCCT$_L$-HC is listed in Table 2. LPETGG in the terminal modification sequence is a recognition sequence of the ligase donor substrate, and GA is a spacer sequence.

TABLE 2

| Modified anti-human TROP2 antibodies | | |
|---|---|---|
| | Sequence | Sequence introduced at the terminal |
| Ab0064-LCCT$_L$-HC light chain | SEQ ID NO: 19 | GALPETGG (SEQ ID NO: 28) |
| Ab0064-LCCT$_L$-HC heavy chain | SEQ ID NO: 20 | —* |

*— indicates no terminal modification

The modified anti-human CLDN18.2 antibody is listed in Table 3. LPETGG in the terminal modification sequence is a recognition sequence of the ligase donor substrate, and GA is a spacer sequence.

TABLE 3

| Modified anti-human CLDN18.2 antibody | | |
|---|---|---|
| | Sequence | Sequence introduced at the terminal |
| Ab0098-LCCT$_L$-HC light chain | SEQ ID NO: 23 | GALPETGG (SEQ ID NO: 28) |

TABLE 3-continued

| Modified anti-human CLDN18.2 antibody | | |
|---|---|---|
| | Sequence | Sequence introduced at the terminal |
| Ab0098-LCCT$_L$-HC heavy chain | SEQ ID NO: 24 | -* |

*— indicates no terminal modification

Example 2 Preparation of Intermediates

2.1 Preparation of the Linking Unit

2.1.1 Linking Units Wherein A and Lm Present

Figure 5:
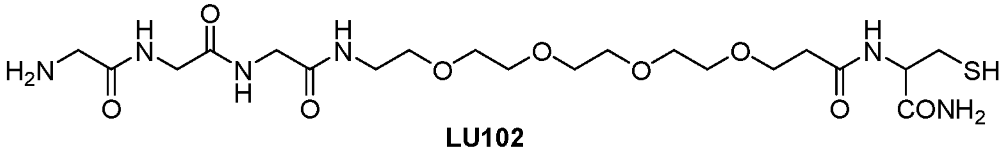
FIG. 5: Linking unit fragments LU102 to LU110.
Figure 5:
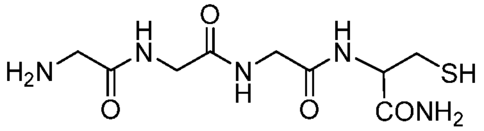
Figure 5:
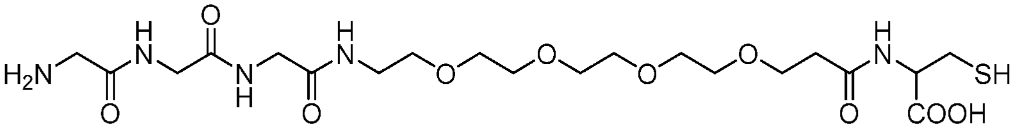
Figure 5:
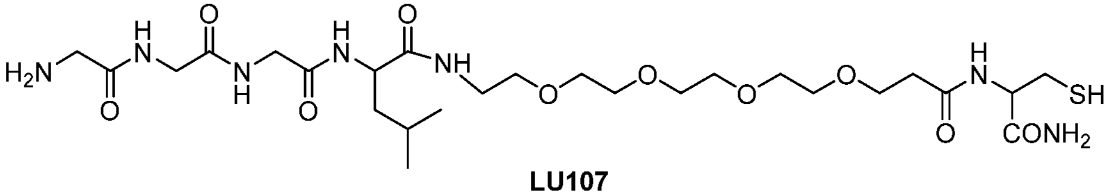
Figure 5:
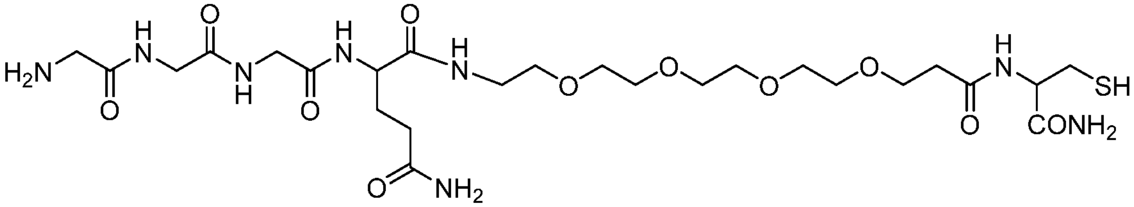
Figure 5:
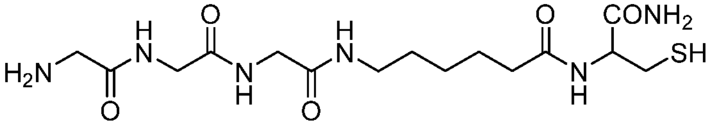
Figure 5:
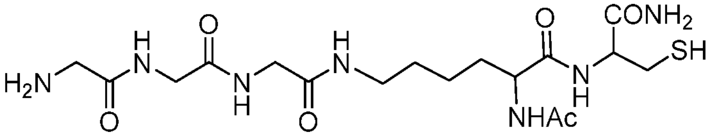

The linking unit fragment LU102 to LU110 which contains moiety A of formula (I') was synthesized by a conventional solid phase polypeptide synthesis using Rink-amide-MBNA-resin or dichloro-resin. Fmoc was used to protect the amino acid and the amino group of the Lk structure in the linking unit. The conjugation reagent was selected from HOBT, HOAt/DIC, DCC, EDCI or HATU. After synthesis, the resin was cleaved using trifluoroacetic acid. The product was purified by HPLC, lyophilized and stored for use. The linking unit fragments are listed in the following table and FIG. 5.

TABLE

| Fragment | Sequence | Mass spectrometry |
|---|---|---|
| LU102 | GGG-NH-$(C_2H_4\text{-}O)_4$-$C_2H_4$-CO-Cys-$NH_2$ | 539.2 $[M + H]^+$ (Theoretical molecular weight: 538.24) |
| LU105 | GGG-Cys-$NH_2$ (GGGC(SEQ ID NO: 30)) | 292.1 $[M + H]^+$ (Theoretical Molecular Weight:, 291.10) |
| LU106 | GGG-NH-$(C_2H_4\text{-}O)_4$-$C_2H_4$-CO-Cys-OH | 540.1 $[M + H]^+$ (Theoretical Molecular Weight:, 539.23) |
| LU107 | GGG-Leu-NH-$(C_2H_4\text{-}O)_4$-$C_2H_4$-CO-Cys-$NH_2$ (GGGL(SEQ ID NO: 31)) | 652.2 $[M + H]^+$ (Theoretical Molecular Weight:, 651.33) |
| LU108 | GGG-Gln-NH-$(C_2H_4\text{-}O)_4$-$C_2H_4$-CO-Cys-$NH_2$ (GGGQ (SEQ ID NO: 32)) | 667.3 $[M + H]^+$ (Theoretical Molecular Weight:, 666.30) |
| LU109 | GGG-NH-$(CH_2)_5$-CO-Cys-$NH_2$ | 405.2 $[M + H]^+$ (Theoretical Molecular Weight:, 404.18) |
| LU110 | GGG-(Ac)Lys-Cys-$NH_2$ | 462.3 $[M + H]^+$ (Theoretical Molecular Weight:, 461.21) |

The linking unit fragments in the above table were reacted with a linking unit fragment which contains a maleimide structure or derivative thereof, and then underwent ring-opening reaction using the method as described in WO2015165413A1 to obtain the linking units LN102-1-1, LN102-2-1, LN102-3-1, LN102-4-1, LN102-7-1, LN102-8-1, LN102-11-1. Their structures are as shown hereinabove. in the following table:

| Linking unit | Fragment containing moiety A | Fragment containing moiety Lm |
|---|---|---|
| LN102-1-1 | LU102 | Mal-OH |
| LN102-2-1 | LU102 | mc-OH |
| LN102-3-1 | LU102 | mc-Val-Cit-PABC |
| LN102-4-1 | LU102 | me-Val-Cit-PABC-(NH—$CR^1R^2$—C(O))—OH, $R^1 = R^2$ = hydrogen |
| LN102-7-1 | LU102 | Mal-(NH—$CR^1R^2$—C(O))—NH—$C_2H_4$—O—H, $R^1 = R^2$ = methyl |
| LN102-8-1 | LU102 | Mal-(NH—$CR^1R^2$—C(O))$_d$—$R^7$ $R^1 = R^2$ = hydrogen |
| LN102-11-1 | LU102 | Mal-(NH—$CR^1R^2$—C(O))$_d$—OH, $R^1 = R^2$ = methyl, $R^{1'}$ and $R^{2'}$ are hydrogen |

2.1.2 Linking Units Wherein A and Lm are Absent

Linking unit LN201 was synthesized by a conventional solid phase polypeptide synthesis using Rink-amide-MBNA-resin. Fmoc was used to protect the amino acid in the linking unit. The conjugation reagent was selected from HOBt, HOAt/DIC, DCC, EDCI or HATU. After synthesis, the resin was cleaved using trifluoroacetic acid. The product was purified by HPLC, lyophilized and stored for use. Theoretical molecular weight: 785.9, measured: $[M+H]^+$=786.8.

2.2 Preparation of Linking Unit-Agonist Intermediates 2.2.1 Preparation of Linking Unit-Agonist Intermediates LP102-1-4

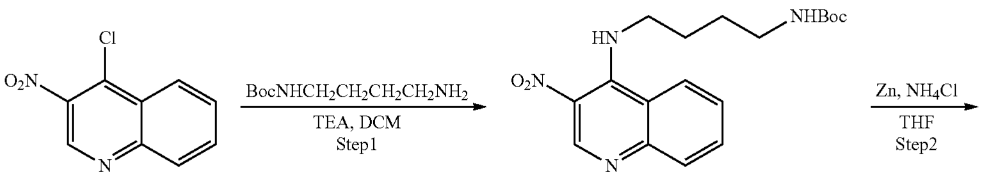

HX20099-a

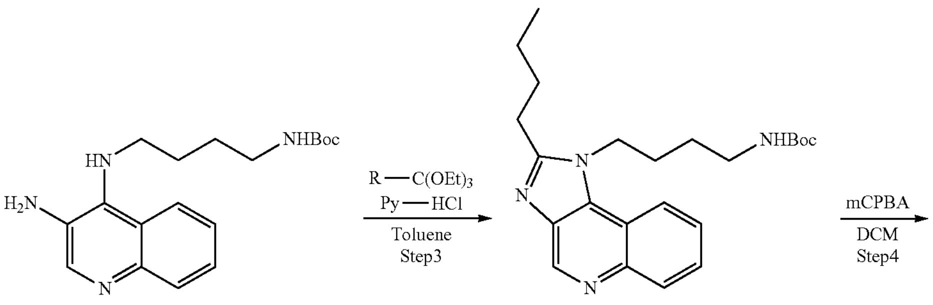

HX20099-b HX20099-c

-continued

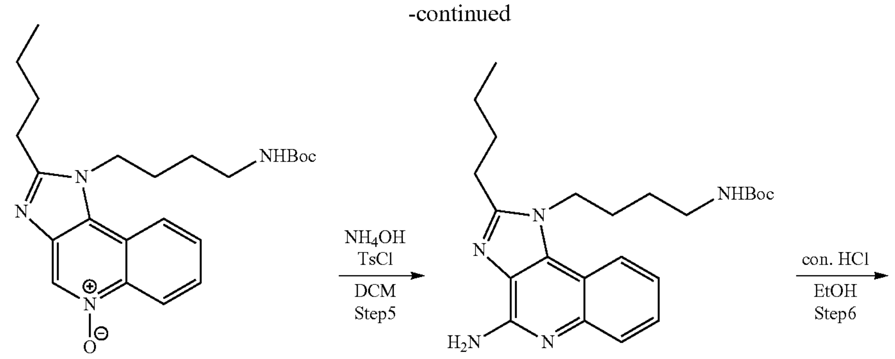

HX20099-d HX20099-e

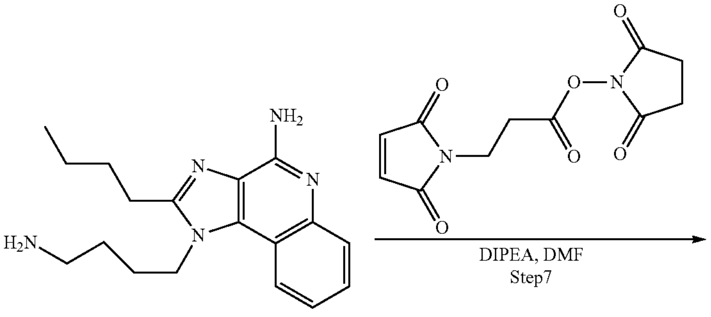

i-3

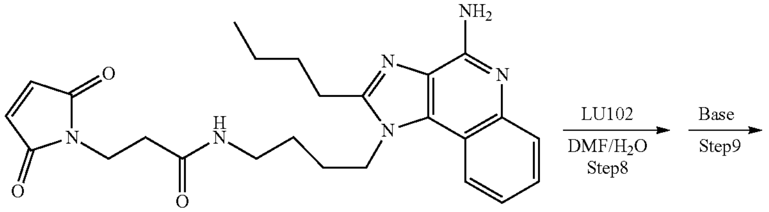

HX2010S

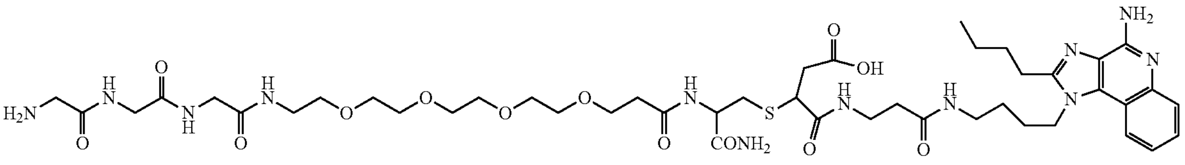

LP102-1-4

Step 1: 4-Chloro-3-nitroquinoline (6.25 g, 30.0 mmol) was dissolved in DCM (100 mL) and trated with BocNH$(CH_2)_4NH_2$ (5.76 g, 30.6 mmol) followed by TEA (8.0 mL, 61.8 mmol). The reaction was kept at room temperature for 24 h, then washed with $H_2O$ (80 mL), brine (50 mL), dried over $MgSO_4$ and concentrated in vacuo. Target compound HX20099-a was obtained as a yellow solid (10.0 g, 92.5%), MS m/z 361.5 $[M+H]^+$.

Step 2: The nitro compound (HX20099-a) (3.0 g, 8.33 mmol) was dissolved in THF (100 mL) and water (80 mL). Zinc (13.54 g, 208.3 mmol) was added in one portion followed by $NH_4Cl$ (13.4 g, 250.0 mmol). The suspension was stirred vigorously at room temperature for 1 h (TLC). After filtration, the cake was washed with THF (20 mL×2). To the filtrate was added NaCl until the aqueous phase was saturated. The liquid phase was collected and the THF layer separated. The aqueous layer was extracted with THF/EA (50 mL/50 mL). The organic layers were combined, dried over $MgSO_4$, and concentrated to obtain residue (HX20099-b) for the next step (3.1 g, >100%). MS m/z 331.5 $[M+H]^+$.

Step 3: Amine compound (HX20099-b) (660 mg, crude, <2.0 mmol) and triethylorthovalerate (816 mg, 4.0 mmol) were suspended in toluene (50 mL) and heated to 110° C. Then pyridine HCl (23.2 mg, 0.2 mmol) was added. The reaction was heated for 4 h. The mixture was kept at room temperature for 48 h (TLC). The liquid was decanted, and the remaining solid/residue was agitated with toluene (10 mL×2) merged with the liquid and concentrated. The residue was dissolved in DCM and purified by silica gel column chromatography (methanol in DCM, 0-10-20%, 30 g column) to obtain target compound HX20099-c (300 mg, 37.8% for two steps) MS m/z 397.5 $[M+H]^+$.

Step 4: Compound HX20099-c (200 mg, 0.51 mmol) was dissolved in DCM (8 mL) and treated with mCPBA (261.5 mg, 1.52 mmol). The reaction was kept at room temperature for 4 h. The mixture was washed with $NaHCO_3$ saturated solution (15 mL×3), dried and concentrated to obtain crude product HX20099-d for the next step. MS m/z 413.5 $[M+H]^+$.

Step 5: In a pressure tube, compound HX20099-d (200 mg, <0.48 mmol) was dissolved in dichloroethane (15 mL) and treated with concentrated ammonium hydroxide (28%, 0.24 mL) and the temperature brought to 0° C. To this mixture, tosyl chloride (104 mg, 0.54 mmol) was slowly added over 3 min after cooling. Concentrated ammonium hydroxide (0.12 mL) was added and the tube was sealed. The tube was heated at 80° C. for 4 h (TLC). After cooling down, the mixture was diluted with DCM (25 mL), washed with water (30 mL), dried and purified by silica gel column chromatography to obtain target compound (HX20099-e) (150 mg, 76%). MS m/z 412.5 $[M+H]^+$.

Step 6: Compound HX20099-e (150 mg, 0.36 mmol) was treated with TFA/DCM (2 mL/6 mL) at room temperature for 2 h (HPLC). Next the reaction was dried in vacuo, and the residue was purified by semi-preparative/preparative HPLC and lyophilized to obtain compound i-3 (74 mg, 66%). MS m/z 312.5 $[M+H]^+$.

Step 7: Compound i-3 (62 mg, 0.2 mmol) was dissolved in DMF (5 mL) and treated with DIPEA (66 μL, 0.4 mmol) and N-Succinimidyl 3-maleimidopropionate (63.9 mg, 0.24 mmol). The reaction was kept at room temperature for 3 h (HPLC), then the mixture was used for next step directly.

Step 8-9: The mixture from step 7 was treated with the solution of linking unit LU102 (161 mg, 0.3 mmol) and $H_2O$ (5 mL). The mixture was reacted at 0-40° C. for 0.5-20h. Then the reaction mixture was mixed with an appropriate amount of Tris Base solution or other solution that promotes the ring-opening reaction, and the reaction was performed at 0-40° C. for 0.2-20 h. After the reaction was completed, the product was purified by semi-preparative/preparative HPLC and lyophilized to obtain linking unit-agonist LP102-1-4 (60 mg, 30% for three steps). MS m/z 1019.5 $[M+H]^+$.

2.2.2 Preparation of Linking Unit-Agonist LP201-1-1

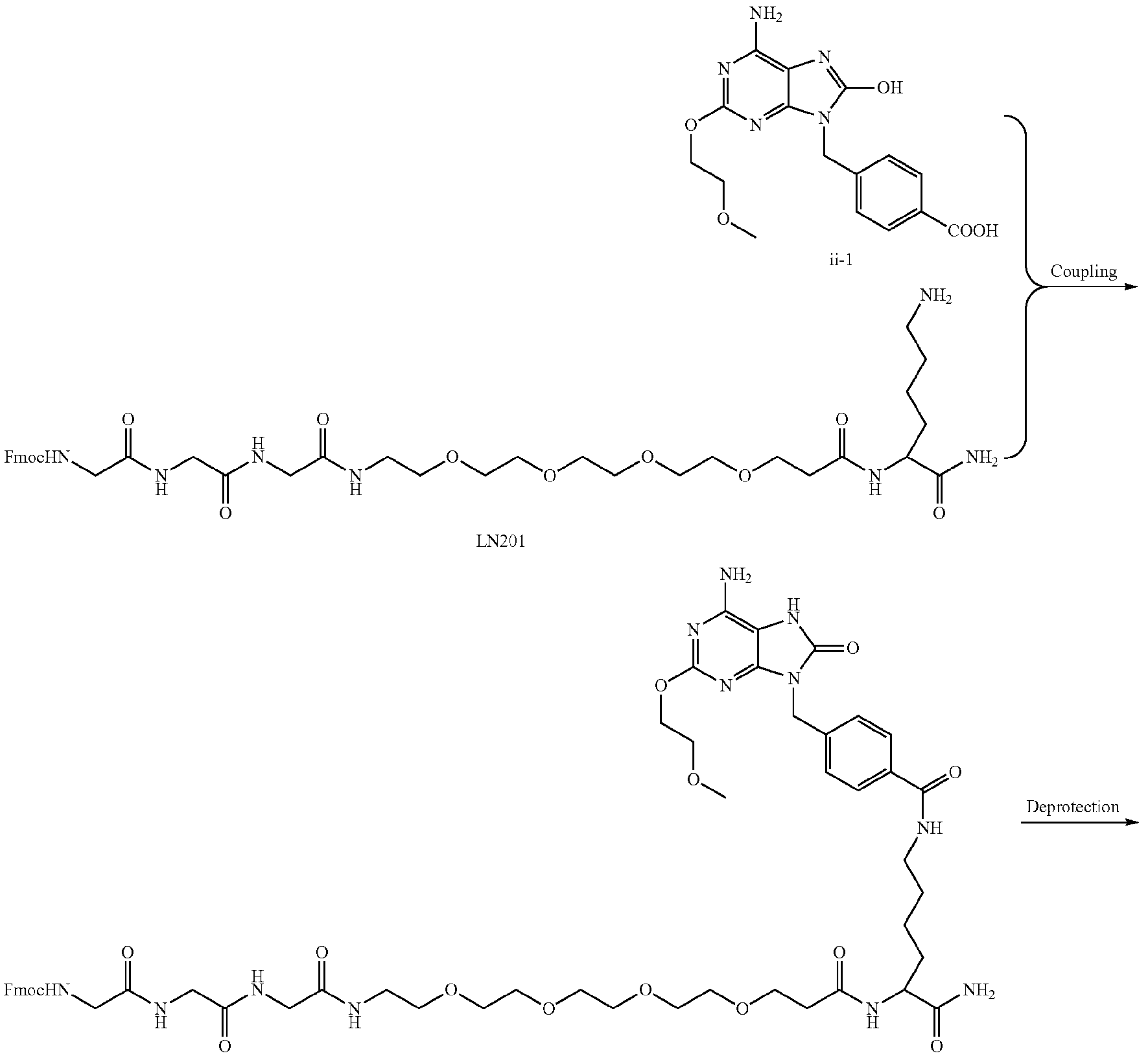

ii-1

LN201

Fmoc-LP201-1-1

-continued

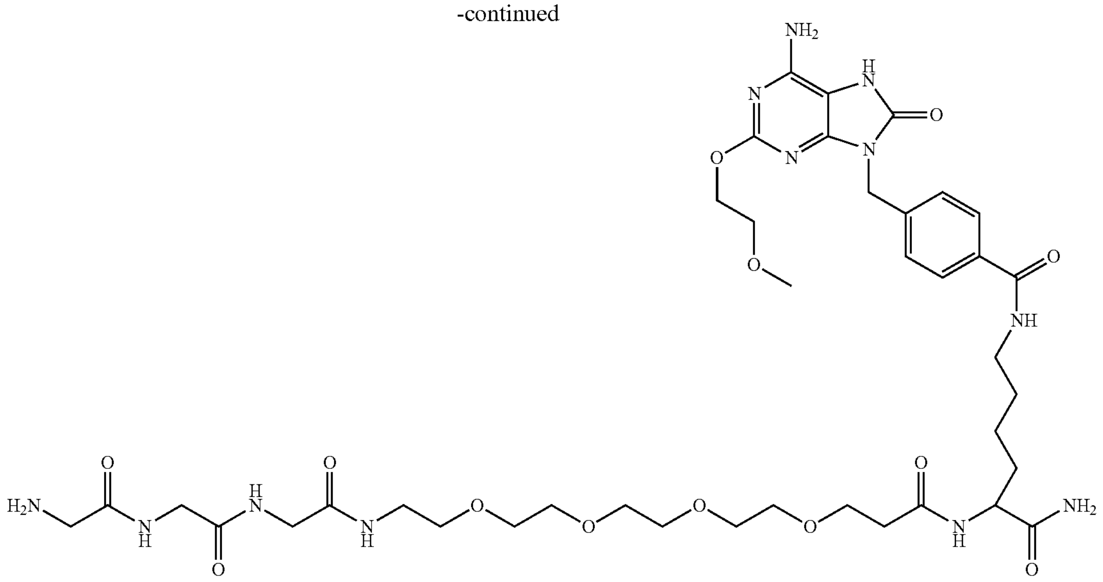

LP201-1-1

Step 1: Preparation of Fmoc-LP201-1-1

The purchased agonist ii-1 was weighed and dissolved in DMF. Then DIEA or $Et_3N$ and conjugation reagents, which were selected from HOBt, HOAt/DIC, DCC, EDCI or HATU, were added. The mixture was stirred for 10-120 min. Then solution of linking unit LN201 and DMF was added into the reaction mixture, which was reacted at 0-40° C. for 0.5-20h. After the reaction was completed, the product was purified by semi-preparative/preparative HPLC and lyophilized to obtain Fmoc-LP201-1-1. Theoretical molecular weight: 1127.2, measured: $[M+H]^+$=1127.7.

Step 2: Preparation of Linking Unit-Agonist LP201-1-1

Fmoc-LP201-1-1 was weighed and dissolved in piperidine/DMF (v/v=1:4). Then the mixture was reacted at 0-40° C. for 0.5-20h. After the reaction was completed, the product was purified by semi-preparative/preparative HPLC and lyophilized to obtain LP201-1-1. Theoretical molecular weight: 905.0, measured: $[M+H]^+$=905.6.

| Linking unit-Agonist intermediate | Linking unit | Agonist | Mass spectrometry |
|---|---|---|---|
| LP102-6-1 | LN102-6 | i-1 | $[M + H]^+$ = 1065.5 |
| LP102-7-1 | LN102-7 | i-1 | $[M + H]^+$ = 1150.7 |
| LP102-8-1 | LN102-8 | i-1 | $[M + H]^+$ = 1079.6 |
| LP102-11-1 | LN102-11 | i-1 | $[M + H]^+$ = 1164.7 |
| LP102-1-1 | LN102-1 | iii-1 | $[M + H]^+$ = 1146.7 |
| LP102-1-2 | LN102-1 | ii-1 | $[M + H]^+$ = 1202.1 |
| LP102-2-1 | LN102-2 | iv-1 | $[M + H]^+$ = 1212.8 |
| LP102-3-1 | LN102-3 | iv-1 | $[1/2M + H]^+$ = 809.0 |
| LP102-4-1 | LN102-4 | i-1 | $[1/2M + H]^+$ = 764.2 |
| LP102-1-3 | LN102-1 | i-2 | $[M + H]^+$ = 1032.7 |
| LP102-1-4 | LN102-1 | i-3 | $[M + H]^+$ = 1019.5 |
| LP102-1-5 | LN102-1 | i-4 | $[M + H]^+$ = 991.5 |

-continued

| Linking unit-Agonist intermediate | Linking unit | Agonist | Mass spectrometry |
|---|---|---|---|
| LP102-1-6 | LN102-1 | i-5 | $[M + H]^+$ = 977.5 |
| LP201-1-1 | LN201 | ii-1 | Theoretical molecular weight: 905.0, measured: $[M + H]^+$ = 905.6. |

Example 3 Preparation of Targeting Molecule-Pharmaceutical Conjugates

The linking unit-agonist intermediates were respectively conjugated to an antibody in a site-specific manner by a ligase to form an AIAC. The method for conjugation reaction can be found in WO2015165413A1. The resulting AIACs are as listed in the following table:

| AIAC | Linking unit-Agonist intermediate | A (targeting molecule) | DAR |
|---|---|---|---|
| AC102-1-1-1 | LP102-1-1 | Ab0001-$LCCT_L$-HC | 1.89 |
| AC102-1-1-2 | LP102-1-2 | Ab0001-$LCCT_L$-HC | 1.92 |
| AC102-1-1-3 | LP102-1-3 | Ab0001-$LCCT_L$-HC | 1.98 |
| AC102-1-1-4 | LP102-1-4 | Ab0001-$LCCT_L$-HC | 1.90 |
| AC102-1-1-5 | LP102-1-5 | Ab0001-$LCCT_L$-HC | 1.84 |
| AC102-1-1-6 | LP102-1-6 | Ab0001-$LCCT_L$-HC | 1.83 |
| AC102-2-1-1 | LP102-2-1 | Ab0001-$LCCT_L$-HC | 1.86 |
| AC102-3-1-1 | LP102-3-1 | Ab0001-$LCCT_L$-HC | 1.88 |
| AC102-4-1-1 | LP102-4-1 | Ab0001-$LCCT_L$-HC | 1.82 |
| AC102-6-1-1 | LP102-6-1 | Ab0001-$LCCT_L$-HC | 1.74 |
| AC102-7-1-1 | LP102-7-1 | Ab0001-$LCCT_L$-HC | 1.72 |
| AC102-8-1-1 | LP102-8-1 | Ab0001-$LCCT_L$-HC | 1.79 |
| AC102-11-1-1 | LP102-11-1 | Ab0001-$LCCT_L$-HC | 1.70 |
| AC201-1-1-1 | LP201-1-1 | Ab0001-$LCCT_L$-HC | 1.86 |
| AC102-6-2-1 | LP102-6-1 | Ab0064-$LCCT_L$-HC | 1.76 |
| AC102-8-2-1 | LP102-8-1 | Ab0064-$LCCT_L$-HC | 1.80 |
| AC201-1-2-1 | LP201-1-1 | Ab0064-$LCCT_L$-HC | 1.84 |
| AC102-8-3-1 | LP102-8-1 | Ab0098-$LCCT_L$-HC | 1.7 |
| AC201-1-3-1 | LP201-1-1 | Ab0098-$LCCT_L$-HC | 1.79 |

Effect Example 1 Assessment of Antibody Immune Agonist Conjugate In Vitro

Isolation of Human Peripheral Mononuclear Cells

Human peripheral mononuclear cells were isolated from healthy blood donors using SepMate 50 and Lymphoprep (Stem Cell Technologies). The live cells was counted and the cell concentration was adjusted to $1.25\times10^6$/ml in RPMI1640 medium with 10% FBS. Tumor cells were detached by trypsin, and collected. The live cells was counted and the cell concentration was adjusted to $2.5\times10^5$/ml in RPMI1640 medium with 10% FBS. $12.5\times10^4$ human PBMC and $2.5\times10^4$ tumor cells (PBMC: tumor cells=5:1) were added into wells of 96 well plate, then the antibody or conjugate was added at indicated concentrations. The cell mixture was incubated with drugs for 18 hours, then the cell-free supernatant was collected for human TNFα ELISA.

Figure 6:
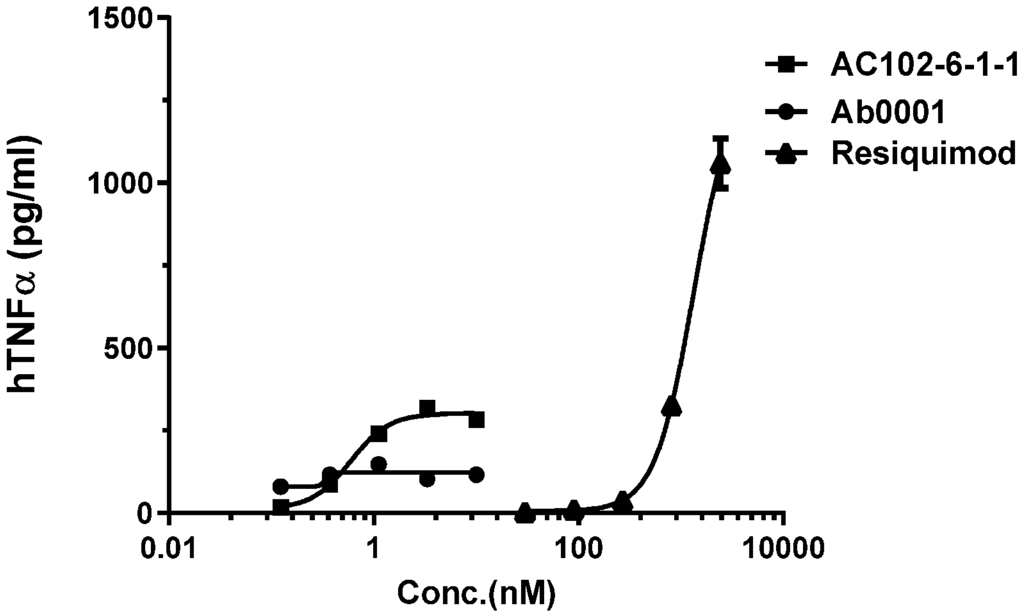
FIG. 6: TNFα induction activity in human PBMC-NCI N87 co-culture assay for conjugate AC102-6-1-1 and the corresponding naked unmodified antibody Ab0001 (Trastuzumab), and agonist Resiquimod.
Figure 7:
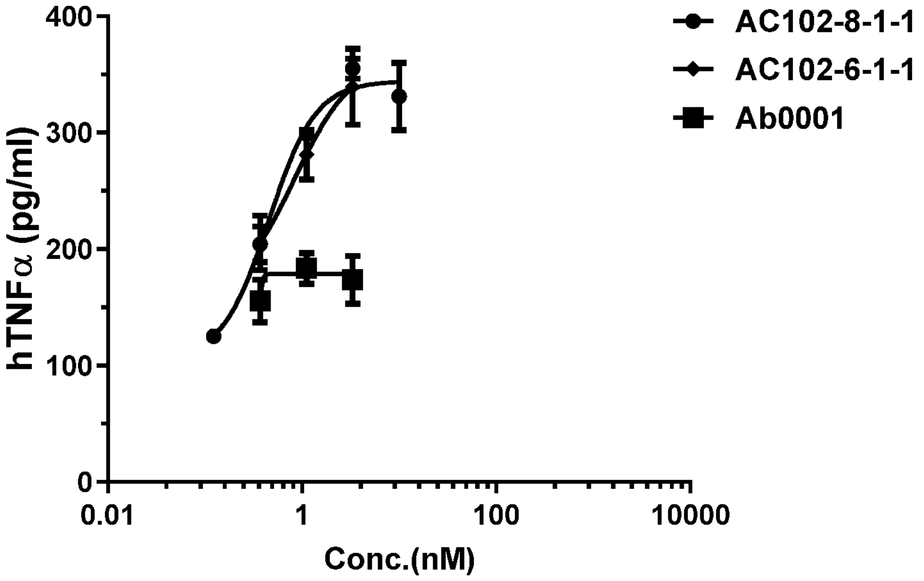
FIG. 7: TNFα induction activity in human PBMC-NCI N87 co-culture assay for conjugates AC102-6-1-1, AC102-8-1-1 and their corresponding naked unmodified antibody Ab0001.
Figure 8:
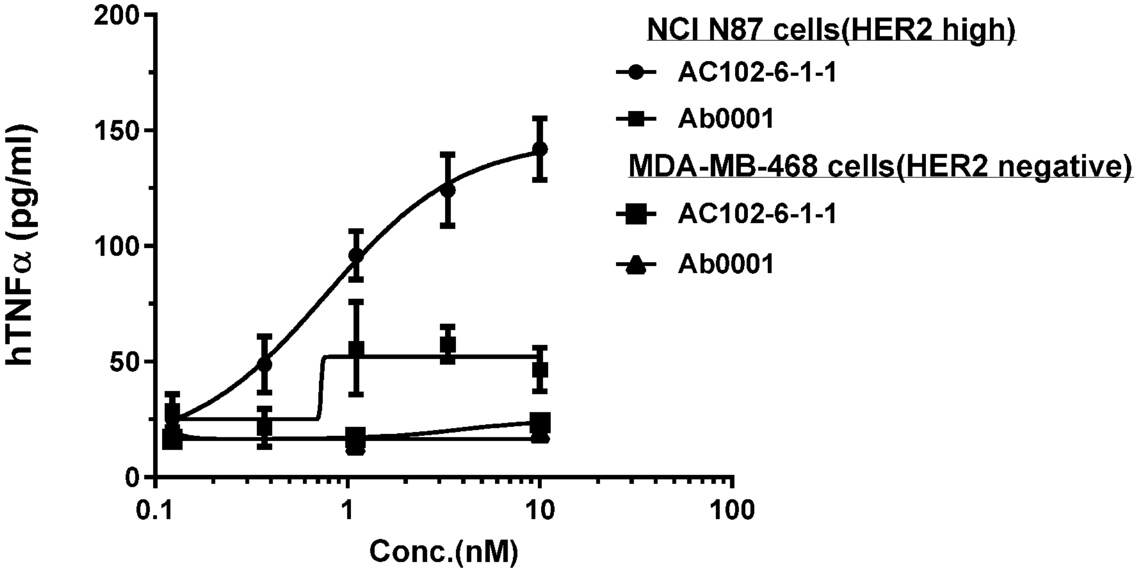
FIG. 8: TNFα induction activity of AC102-6-1-1 and antibody in co-culture of PBMC with either NCI N87 or MDA-MB-468 cells.
Figure 9:
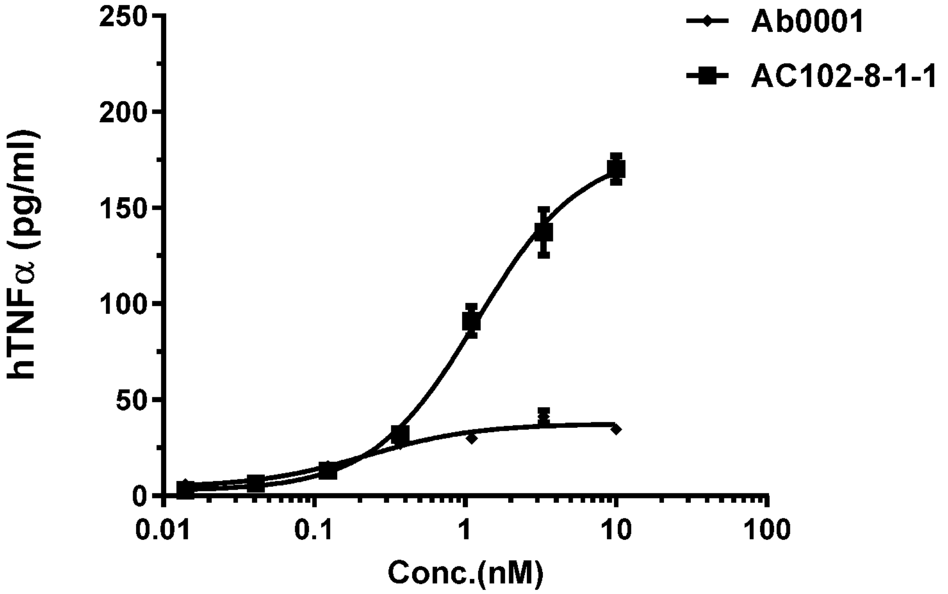
FIG. 9: TNFα induction activity of AC102-8-1-1 and antibody in co-culture of PBMC with HCC1954 cells.
Figure 10:
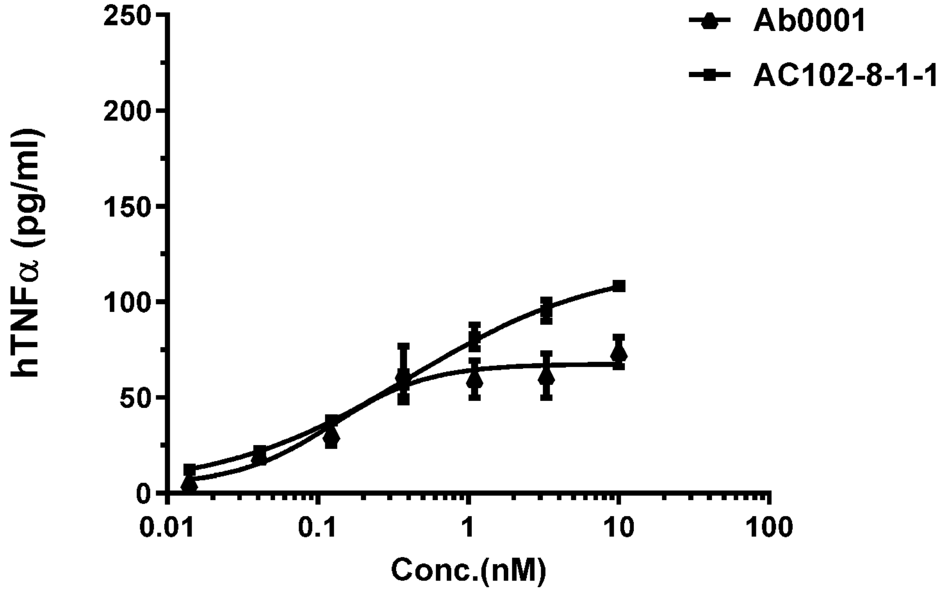
FIG. 10: TNFα induction activity of AC102-8-1-1 and antibody in co-culture of PBMC with SK-BR-3 cells.
Figure 11:
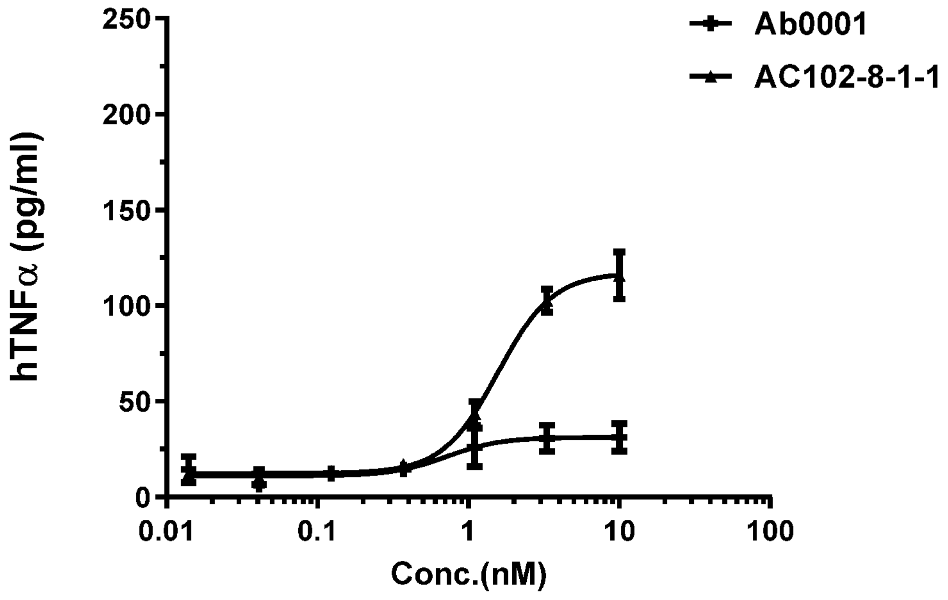
FIG. 11: TNFα induction activity of AC102-8-1-1 and antibody in co-culture of PBMC with BT474 cells.
Figure 12:
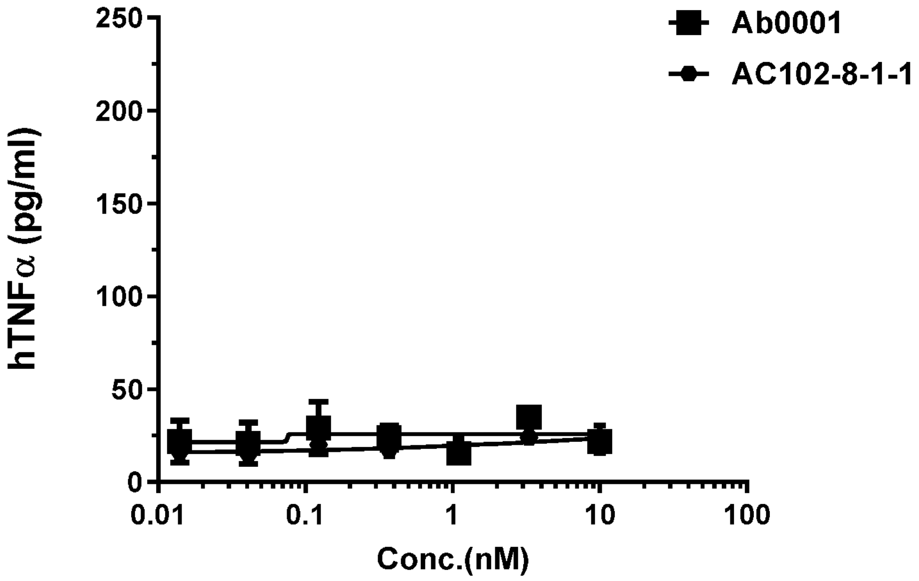
FIG. 12: TNFα induction activity of AC102-8-1-1 and antibody in co-culture of PBMC with JIMT1 cells.
Figure 13:
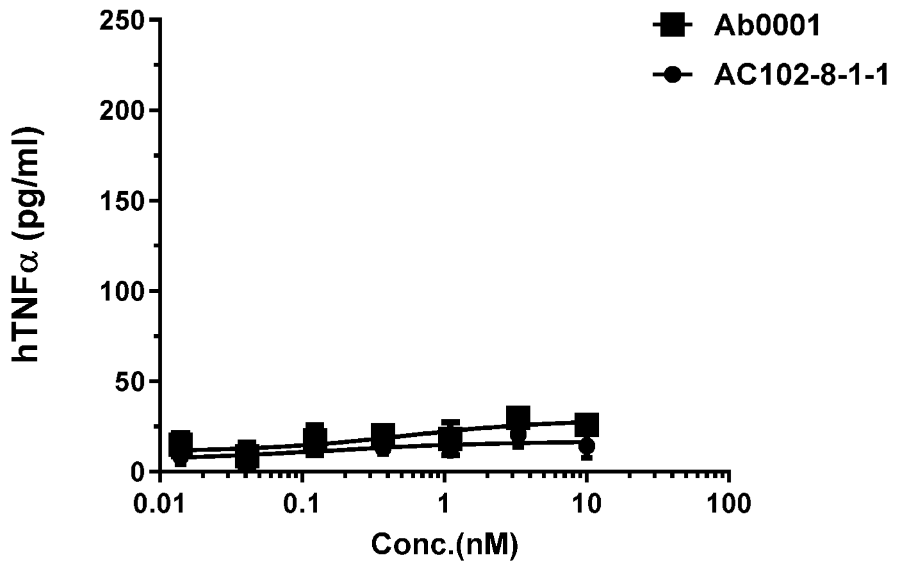
FIG. 13: TNFα induction activity of AC102-8-1-1 and antibody in co-culture of PBMC with Colo205 cells.
Figure 14:
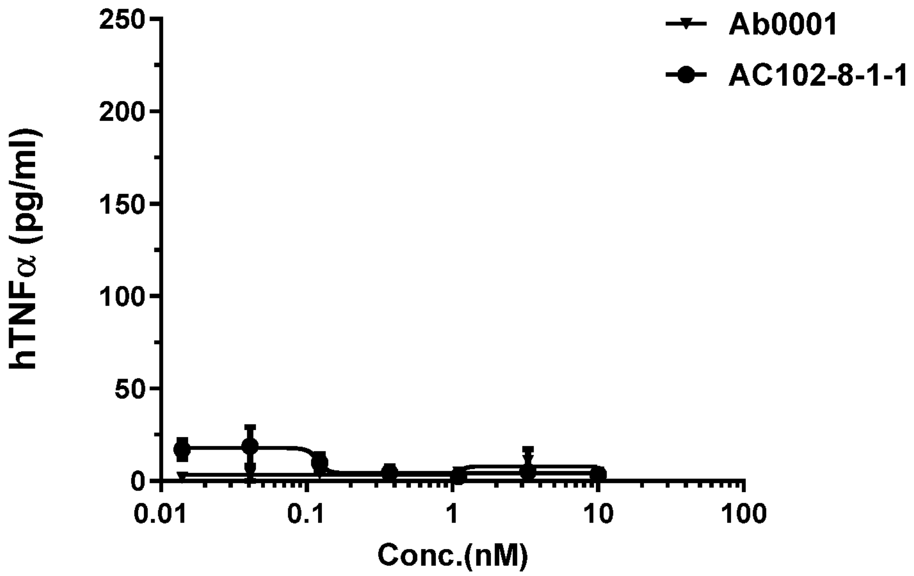
FIG. 14: TNFα induction activity of AC102-8-1-1 and antibody in co-culture of PBMC with MDA-MB-468 cells.

To evaluate the activity of HER2 targeted immunoconjugates, human PBMC and NCI N87 human gastric cancer cells were co-cultured at a ratio of 5:1, and the antibody or the test immunoconjugate (AC102-6-1-1 or AC102-8-1-1) at indicated concentrations were added. AC102-6-1-1 induced higher TNFα production than the antibody Ab0001, and the effective concentration of AC102-6-1-1 was much lower than the payload Resiquimod (FIG. 6). AC102-8-1-1 induced higher level of TNFα than Ab0001, which was similar to AC102-6-1-1 (FIG. 7). The activity of AC102-6-1-1 was not observed in co-culture of human PBMC and MDA-MB-468 HER2 negative cells, indicating the activity of AC102-6-1-1 was highly dependent on HER2 expression on target tumor cells (FIG. 8). In light of this data, the activity of immunoconjugate was tested in co-culture of human PBMC and other cancer cells with different HER2 expression level, including HCC1954 (FIG. 9), SK-BR-3 (FIG. 10), BT474 (FIG. 11), JIMT1 (FIG. 12), Colo205 (FIG. 13), MDA-MB-468 (FIG. 14). The data showed that AC102-8-1-1 was only capable to induce TNFα in co-culture of PBMC and HER2 high tumor cells.

Figure 15:
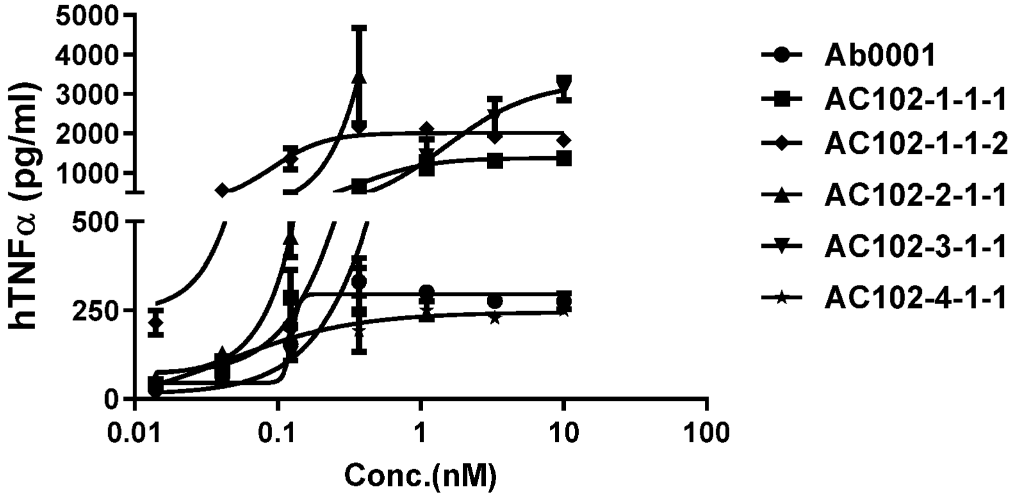
FIG. 15: TNFα induction activity of AC102-1-1-1, AC102-1-1-2, AC102-2-1-1, AC102-3-1-1, AC102-4-1-1, and antibody in co-culture of PBMC with NCI N87 cells.
Figure 16:
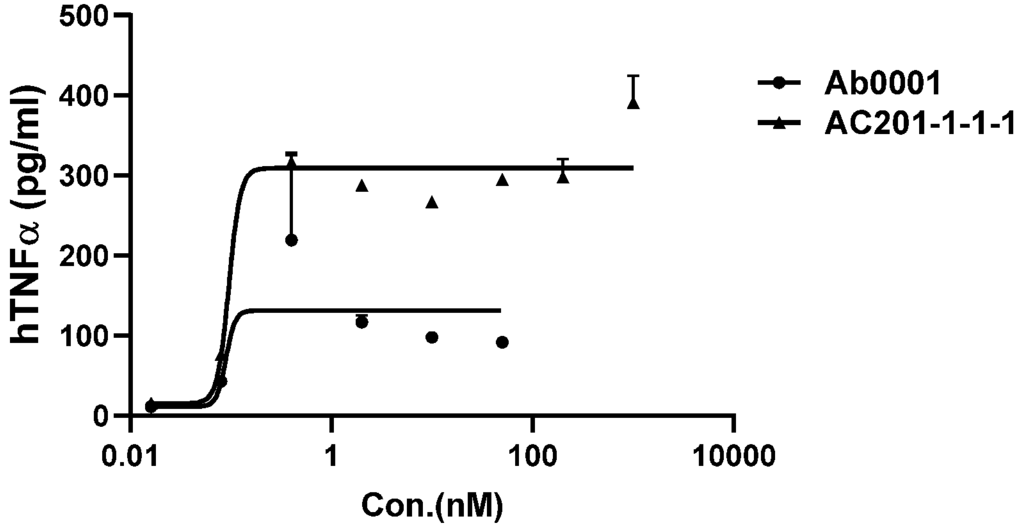
FIG. 16: TNFα induction activity of AC201-1-1-1 and antibody in co-culture of PBMC with NCI N87 cells.
Figure 17:
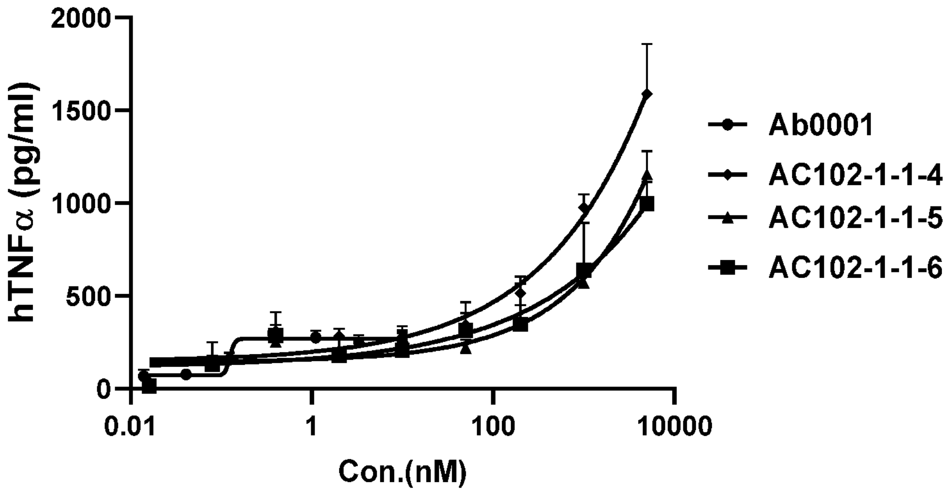
FIG. 17: TNFα induction activity of AC102-1-1-4, AC102-1-1-5, AC102-1-1-6 and antibody in co-culture of PBMC with NCI N87 cells.

In similar experimental setting, in vitro activity of several other conjugates was evaluated (FIG. 15-FIG. 17). AC102-2-1-1 and AC102-3-1-1 have same agonist payload, but different linking unit, and induced different level of TNFα production (FIG. 15).

Effect Example 2 Assessment of Antibody Immune Agonist Conjugate In Vitro

Figure 18:
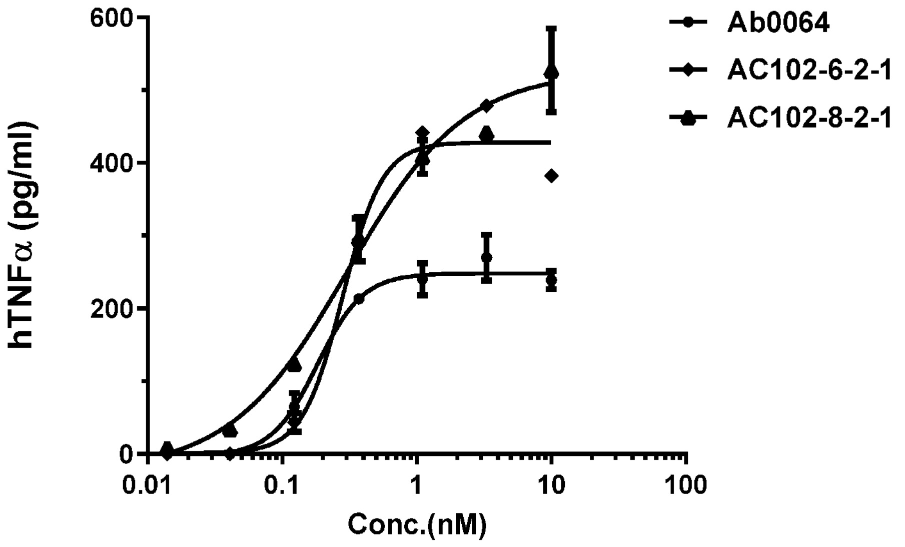
FIG. 18: TNFα induction activity of AC102-8-2-1 and AC102-6-2-1 and antibody in co-culture of PBMC with NCI N87 cells.

To evaluate the activity of TROP2-targeted immunoconjugates, human PBMC and NCI-N87 human gastric cancer cells were co-cultured at a ratio of 5:1, and the test immunoconjugate (AC102-8-2-1 or AC102-6-2-1) or naked unmodified anti-TROP2 antibody at indicated concentrations were added. The isolation of human PBMC and experimental setting were similar to Effect Example 1. AC102-8-2-1 and AC102-6-2-1 induced higher TNFα production than the antibody Ab0064 (light chain: SEQ ID No. 17, heavy chain: SEQ ID No. 18) (FIG. 18).

Effect Example 3 Assessment of Antibody Immune Agonist Conjugate In Vitro

Figure 19:
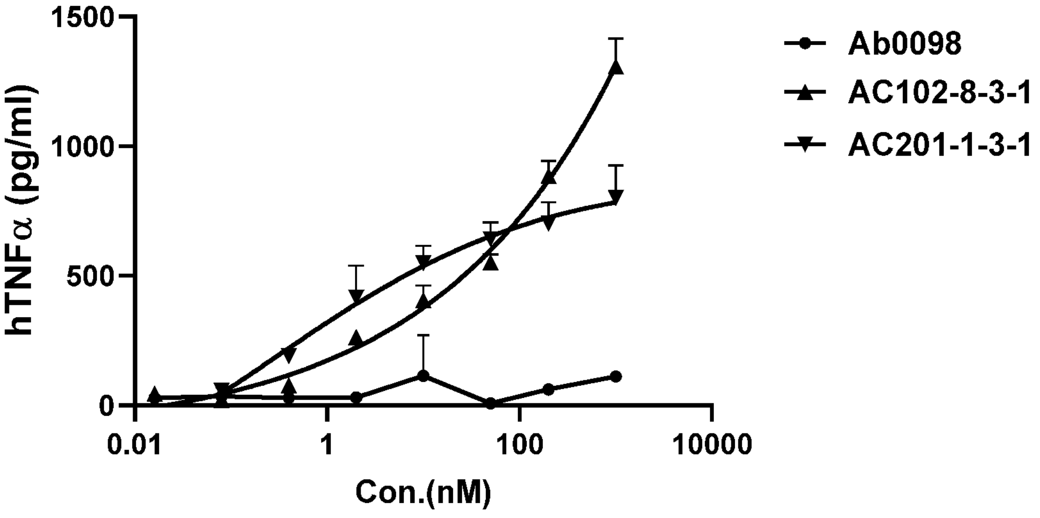
FIG. 19: TNFα induction activity of AC102-8-3-1, AC201-1-3-1, and antibody in co-culture of PBMC with human gastric cancer cell NCI-N87 that overexpressing human Claudin 18.2 (as referred to as NCI-N87-Claudin 18.2).
Figure 20:
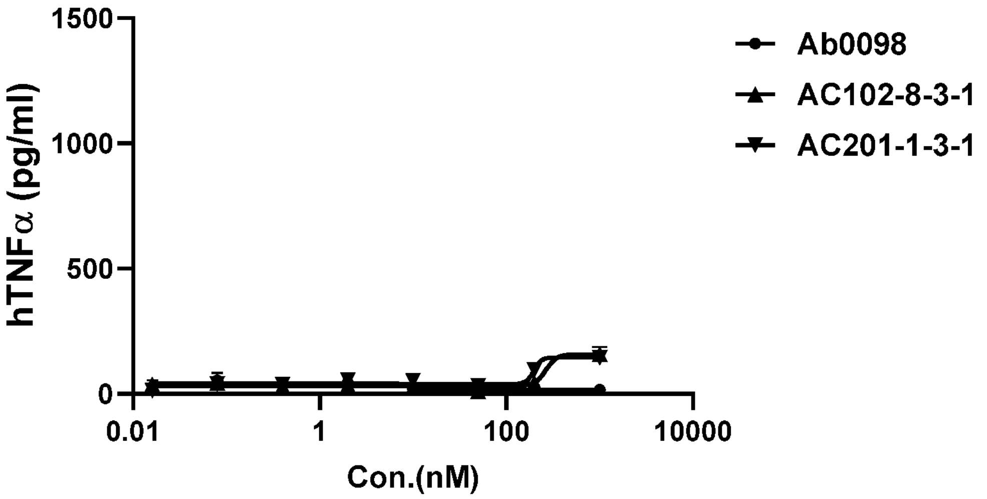
FIG. 20: TNFα induction activity of AC102-8-3-1, AC201-1-3-1, and antibody in Claudin 18.2-negative NCI-N87 parental cells.

Claudin 18.2 could also serve as an example of AIAC targets. To evaluate the activity of Claudin 18.2-targeted immunoconjugates, NCI-N87—Claudin 18.2 human gastric cancer cells overexpressing human Claudin 18.2 or parental NCI-N87 cells were co-cultured with human PBMC at a ratio of 1:5, and the test immunoconjugate (AC102-8-3-1 or AC201-1-3-1) or naked unmodified anti-Claudin 18.2 antibody at indicated concentrations were added, respectively. The isolation of human PBMC and experimental setting were similar to Effect Example 1. AC102-8-3-1 and AC201-1-3-1 conjugates induced higher TNFα production compared to antibody Ab0098 (FIG. 19), while those conjugates only showed negligible induction of TNFα production at very high doses in Claudin 18.2-negative NCI-N87 parental cells (FIG. 20). The conjugates prepared using linker-payload intermediate LP201-1-1 with Ab0098-LCCT$_L$-HC exhibited milder activities as compared to conjugates prepared using linker-payload intermediate LP102-8-1 with Ab0098-LCCT$_L$-HC, which is consistent with the potency of these two payloads.

Effect Example 4 Assessment of Antibody Immune Agonist Conjugate In Vitro

Figure 21:
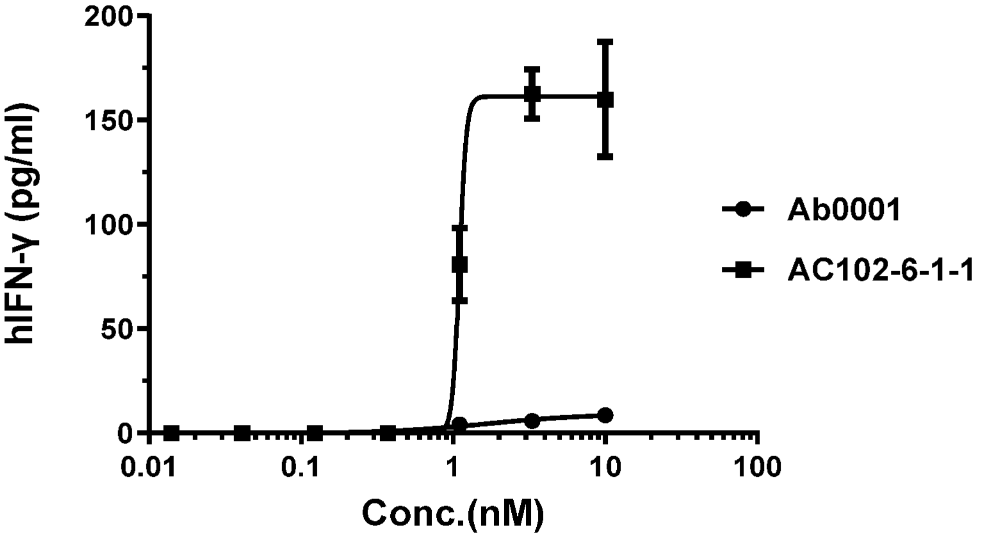
FIG. 21: INF-γ induction activity of AC102-6-1-1 and antibody in co-culture of PBMC with SK-BR-3 cells.
Figure 22:
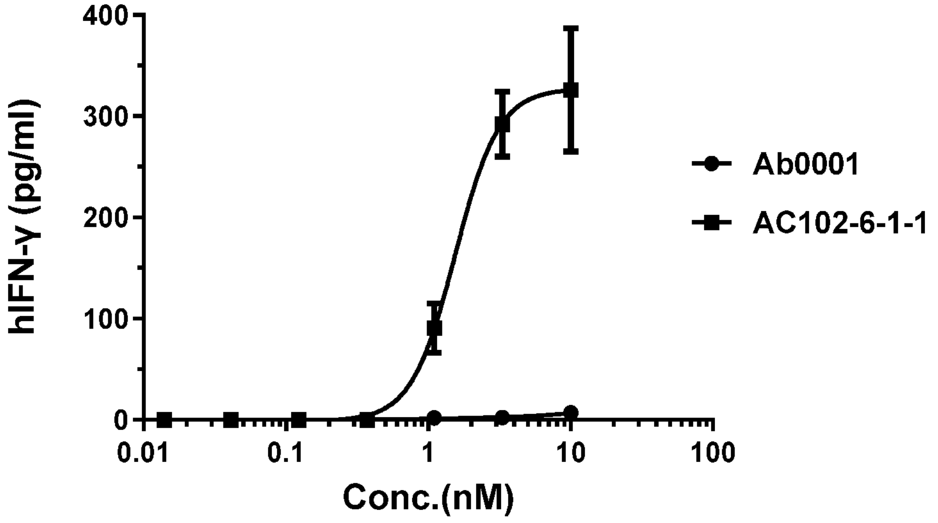
FIG. 22: INF-γ induction activity of AC102-6-1-1 and antibody in co-culture of PBMC with HCC1954 cells.

To evaluate the activity of HER2 targeting immunoconjugates, human PBMC and SK-BR-3 (FIG. 21) or HCC1954 (FIG. 22) human breast cancer cells were co-cultured at a ratio of 5:1, and immunoconjugate (AC102-6-1-1) and antibody (Ab0001) at indicated concentrations were added. Cells were incubated drugs for 18 hours, then cell-free supernatant were collected for human IFNγ detection by ELISA. The isolation of human PBMC and experimental setting were similar to Effect Example 1. AC102-6-1-1 induced higher IFNγ production than the antibody Ab0001, suggesting potential capability to activate T cell response.

Effect Example 5 Assessment of Antibody Immune Agonist Conjugate In Vivo

Figure 23:
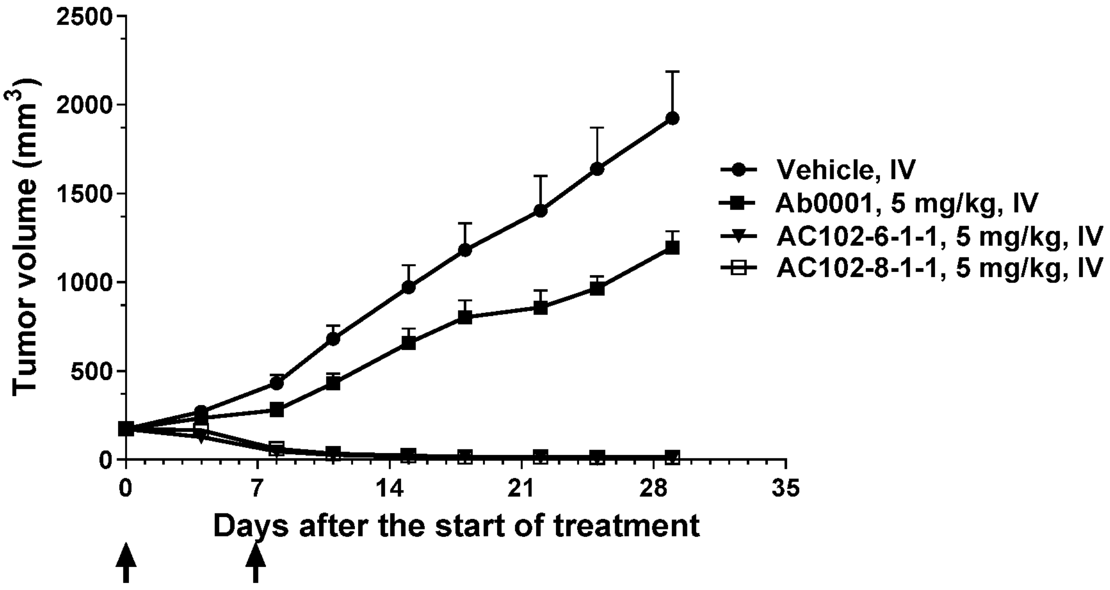
In FIGS. 23 to 30, the arrow(s) under the X-axis indicate(s) the time point of administration.
Figure 24:
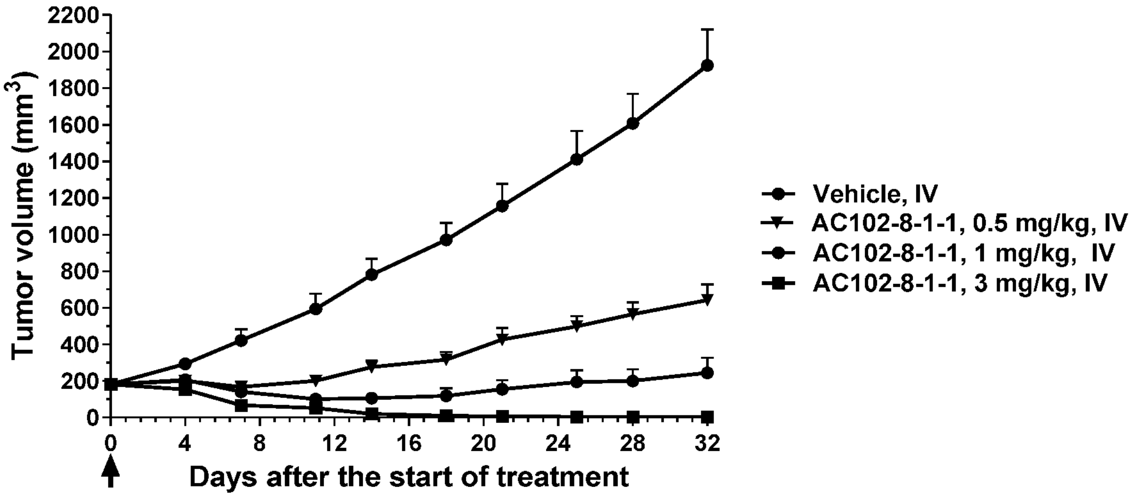

For in vivo anti-tumor efficacy study, $1\times10^7$ NCI-N87 human gastric cancer cells were inoculated subcutaneously in the right flank in SCID Beige mice. After 6 days, when tumor volume reached 173 $mm^3$ on average, the tumor bearing mice were assigned and administered intravenously of Ab0001 or the test immunoconjugate (AC102-6-1-1 or AC102-8-1-1) at 5 mg/kg. The tumor volume was measured twice weekly with calipers. The antibody itself, Ab0001, showed very limited anti-tumor activity. AC102-6-1-1 and AC102-8-1-1 almost cured the tumors at the end (FIG. 23). In a separate study, AC102-8-1-1 displayed dose-dependent activity at 0.5, 1, and 3 mg/kg (FIG. 24).

Figure 25:
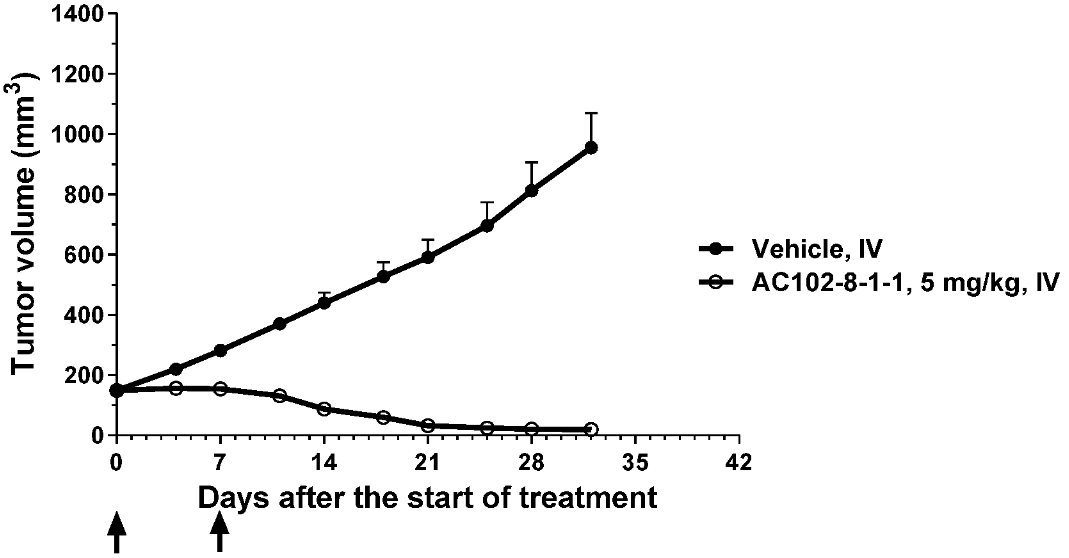

$5\times10^6$ JIMT1 human breast cancer cells were inoculated subcutaneously in the right flank in SCID Beige mice to generate xenograft model. After 9 days, when tumor volume reached 149 $mm^3$ on average, the tumor bearing mice were administered intravenously of AC102-8-1-1 at 5 mg/kg. The tumor growth was significantly inhibited (FIG. 25).

Figure 26:
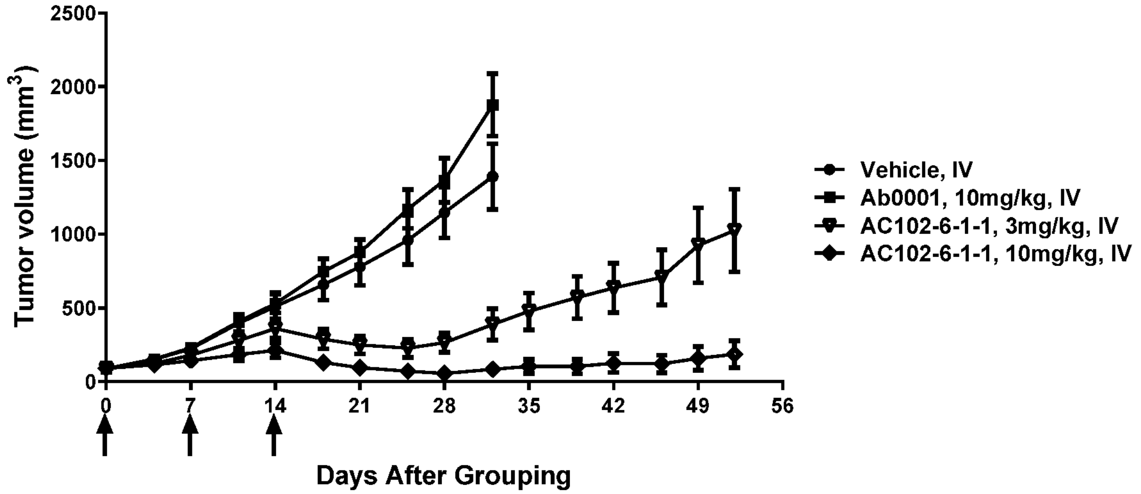
Figure 27:
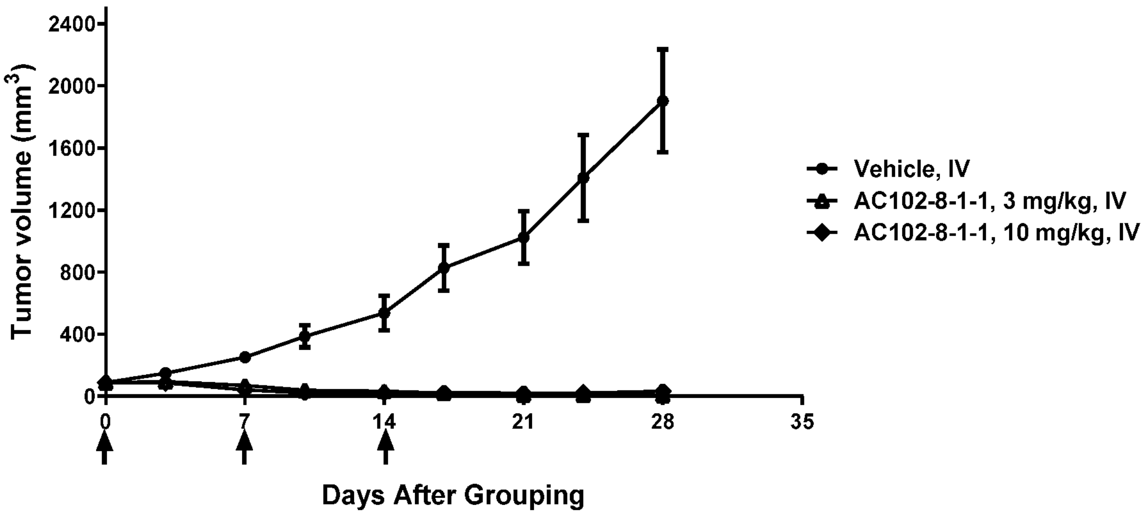

$5\times10^5$ MC38$^{hHER2}$ murine colorectal cancer cells overexpressing human HER2 were inoculated subcutaneously in the right flank in C57BL/6 mice. After 8 days, when tumor volume reached 90 $mm^3$ on average, the tumor bearing mice were assigned and administered intravenously of Ab0001 or AC102-6-1-1. 10 mg/kg Ab0001 showed no obvious anti-tumor activity. 3 mg/kg and 10 mg/kg AC102-6-1-1 dose-dependently inhibited tumor growth (FIG. 26). In a similar setting, AC102-8-1-1 at 3 mg/kg and 10 mg/kg both induced complete tumor regression in 100% of mice (FIG. 27).

Effect Example 6 Assessment of Antibody Immune Agonist Conjugate In Vivo

Figure 28:
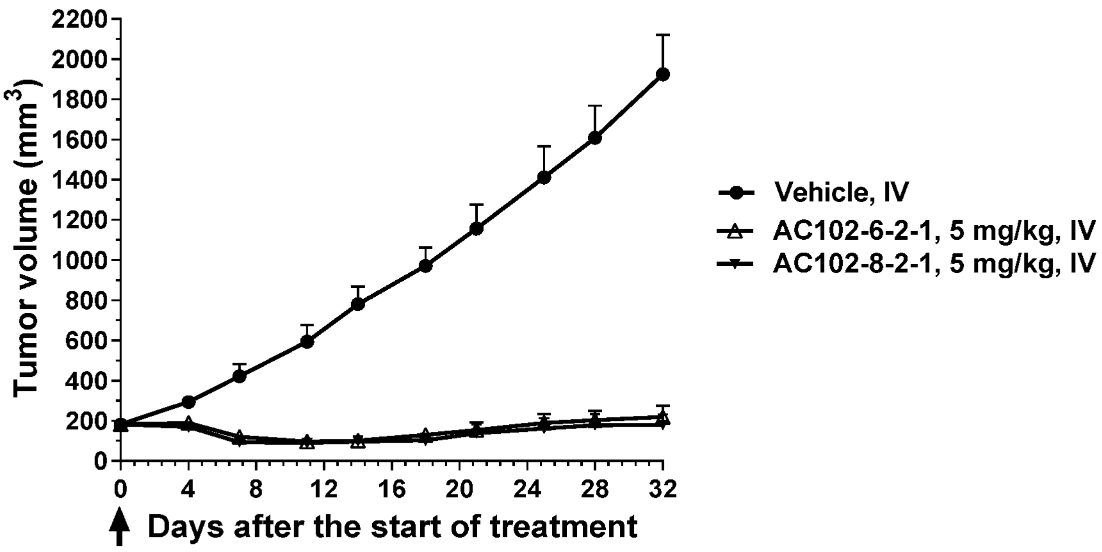

To test in vivo anti-tumor effect of anti-TROP2 AIAC, $1\times10^7$ NCI-N87 human gastric cancer cells were inoculated subcutaneously in the right flank in SCID Beige mice. When tumor volume reached 182 $mm^3$ on average, the tumor bearing mice were assigned and administered intravenously of vehicle or the test immunoconjugate (AC102-6-2-1, AC102-8-2-1 or AC201-1-2-1) at 5 mg/kg. The tumor volume was measured twice weekly with calipers. Comparing to vehicle control, AC102-6-2-1 and AC102-8-2-1 showed strong anti-tumor activity (FIG. 28).

Figure 29:
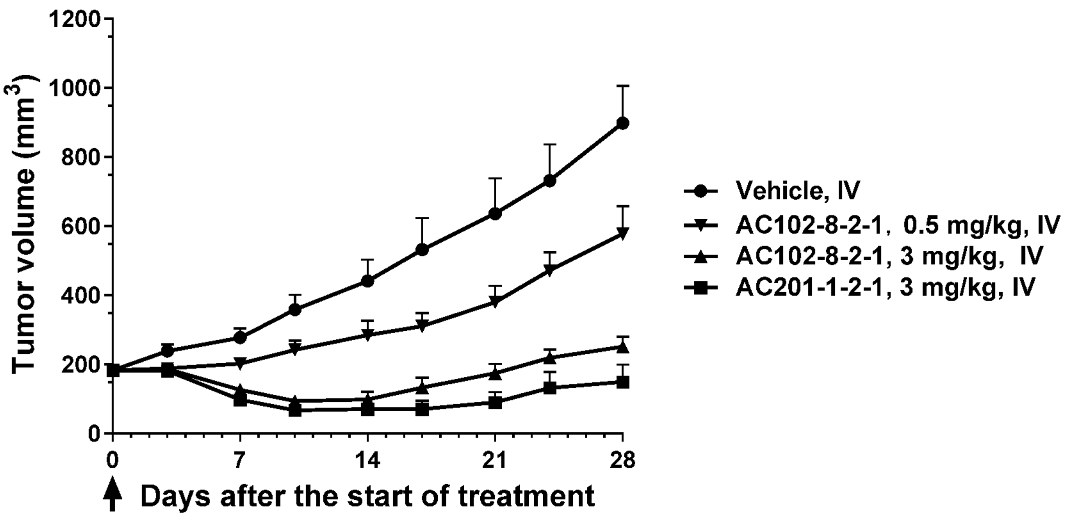

Ten million of MDA-MB-468 human breast cancer cells were inoculated subcutaneously in the right flank in SCID Beige mice to generate xenograft model. After tumor volume reaching 183 $mm^3$ on average, the tumor bearing mice were assigned and administered intravenously of vehicle or the test immunoconjugate (AC102-8-2-1 or AC201-1-2-1). AC102-8-2-1 and AC201-1-2-1 showed good and comparable anti-tumor activity at 3 mg/kg. AC102-8-2-1 at 3 mg/kg exhibited higher anti-tumor response than that at 0.5 mg/kg, indicating dose-dependent effect (FIG. 29).

Effect Example 7 Assessment of Antibody Immune Agonist Conjugate In Vivo

Figure 30:
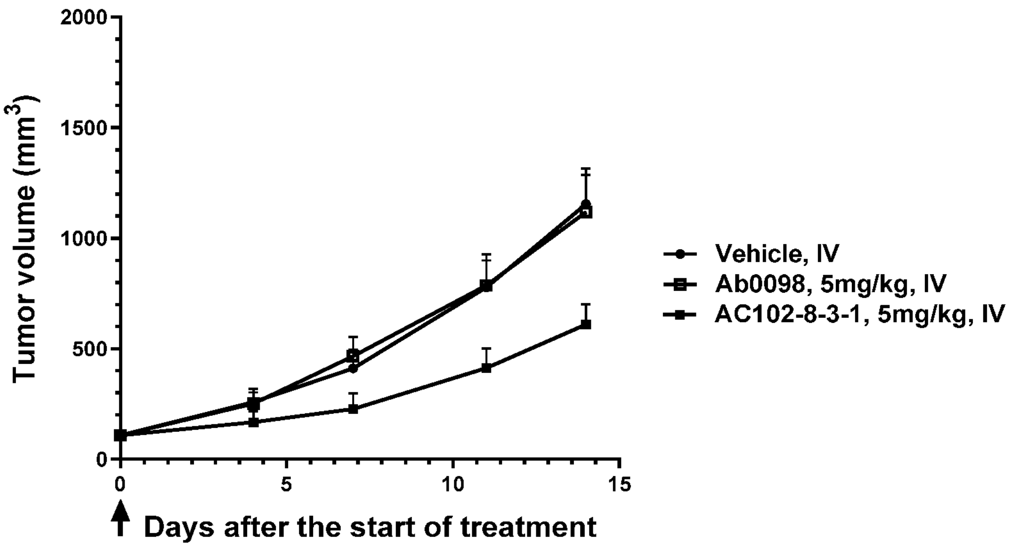

The in vivo anti-tumor efficacy of anti-Claudin 18.2-AIAC was evaluated using a NUGC4 model. One million of NUGC4 human gastric cancer cells were inoculated subcutaneously in the right flank in BALB/c nude mice to generate xenograft model. After tumor volume reaching 108 $mm^3$ on average, the tumor bearing mice were assigned and administered intravenously of the test anti-Claudin 18.2 conjugate (AC102-8-3-1) or the corresponding naked unmodified antibody at 5 mg/kg on day 0 and 14. The tumor volume was measured twice weekly with calipers. The antibody alone, Ab0098 (light chain: SEQ ID No. 21, heavy chain: SEQ ID No. 22), showed no anti-tumor activity, and AC102-8-3-1 showed anti-tumor activity (FIG. 30).

Sequencing List

SEQ ID No. 1: Ab0001-LCCT$_L$-HC Light chain:
DIQMTQSPSSLSASVGDRVTITCRASQDVNTAVAWYQQKPGKAPKLLIYSASFLYSGVPSRFSGSRSGTDFTLTISSLQ
PEDFATYYCQQHYTTPPTFGQGTKVEIKRTVAAPSVFIFPPSDEQLKSGTASWCLLNNFYPREAKVQWKVDNALQS
GNSQESVTEQDSKDSTYSLSSTLTLSKADYEKHKVYACEVTHQGLSSPVTKSFNRGECGALPETGG SEQ ID No. 2: Ab0001-LCCT$_L$-HC Heavy chain:
EVQLVESGGGLVQPGGSLRLSCAASGFNIKDTYIHWVRQAPGKGLEWVARIYPTNGYTRYADSVKGRFTISADTSKNT
AYLQMNSLRAEDTAVYYCSRWGGDGFYAMDYWGQGTLVTVSSASTKGPSVFPLAPSSKSTSGGTAALGCLVKDYFP
EPVTVSWNSGALTSGVHTFPAVLQSSGLYSLSSWTVPSSSLGTQTYICNVNHKPSNTKVDKKVEPKSCDKTHTCPPC
PAPELLGGPSVFLFPPKPKDTLMISRTPEVTCVVVDVSHEDPEVKFNWYVDGVEVHNAKTKPREEQYNSTYRVVSVLT
VLHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK SEQ ID No. 3: Ab0001-LC-HCCT Light chain:
DIQMTQSPSSLSASVGDRVTITCRASQDVNTAVAWYQQKPGKAPKLLIYSASFLYSGVPSRFSGSRSGTDFTLTISSLQ
PEDFATYYCQQHYTTPPTFGQGTKVEIKRTVAAPSVFIFPPSDEQLKSGTASWCLLNNFYPREAKVQWKVDNALQS
GNSQESVTEQDSKDSTYSLSSTLTLSKADYEKHKVYACEVTHQGLSSPVTKSFNRGEC SEQ ID No. 4: Ab0001-LC-HCCT Heavy chain:
EVQLVESGGGLVQPGGSLRLSCAASGFNIKDTYIHWVRQAPGKGLEWVARIYPTNGYTRYADSVKGRFTISADTSKNT
AYLQMNSLRAEDTAVYYCSRWGGDGFYAMDYWGQGTLVTVSSASTKGPSVFPLAPSSKSTSGGTAALGCLVKDYFP
EPVTVSWNSGALTSGVHTFPAVLQSSGLYSLSSWTVPSSSLGTQTYICNVNHKPSNTKVDKKVEPKSCDKTHTCPPC
PAPELLGGPSVFLFPPKPKDTLMISRTPEVTCVVVDVSHEDPEVKFNWYVDGVEVHNAKTKPREEQYNSTYRVVSVLT
VLHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGKLPETGG SEQ ID No. 5: Ab0001-LC-HCCT$_L$ Light chain:
DIQMTQSPSSLSASVGDRVTITCRASQDVNTAVAWYQQKPGKAPKLLIYSASFLYSGVPSRFSGSRSGTDFTLTISSLQ
PEDFATYYCQQHYTTPPTFGQGTKVEIKRTVAAPSVFIFPPSDEQLKSGTASWCLLNNFYPREAKVQWKVDNALQS
GNSQESVTEQDSKDSTYSLSSTLTLSKADYEKHKVYACEVTHQGLSSPVTKSFNRGEC SEQ ID No. 6: Ab0001-LC-HCCT$_L$ Heavy chain:
EVQLVESGGGLVQPGGSLRLSCAASGFNIKDTYIHWVRQAPGKGLEWVARIYPTNGYTRYADSVKGRFTISADTSKNT
AYLQMNSLRAEDTAVYYCSRWGGDGFYAMDYWGQGTLVTVSSASTKGPSVFPLAPSSKSTSGGTAALGCLVKDYFP
EPVTVSWNSGALTSGVHTFPAVLQSSGLYSLSSWTVPSSSLGTQTYICNVNHKPSNTKVDKKVEPKSCDKTHTCPPC
PAPELLGGPSVFLFPPKPKDTLMISRTPEVTCVVVDVSHEDPEVKFNWYVDGVEVHNAKTKPREEQYNSTYRVVSVLT
VLHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGKGALPETGG SEQ ID No. 7: Ab0001-LCCT-HC Light chain:
DIQMTQSPSSLSASVGDRVTITCRASQDVNTAVAWYQQKPGKAPKLLIYSASFLYSGVPSRFSGSRSGTDFTLTISSLQ
PEDFATYYCQQHYTTPPTFGQGTKVEIKRTVAAPSVFIFPPSDEQLKSGTASWCLLNNFYPREAKVQWKVDNALQS
GNSQESVTEQDSKDSTYSLSSTLTLSKADYEKHKVYACEVTHQGLSSPVTKSFNRGECLPETGG SEQ ID No. 8: Ab0001-LCCT-HC Heavy chain:
EVQLVESGGGLVQPGGSLRLSCAASGFNIKDTYIHWVRQAPGKGLEWVARIYPTNGYTRYADSVKGRFTISADTSKNT
AYLQMNSLRAEDTAVYYCSRWGGDGFYAMDYWGQGTLVTVSSASTKGPSVFPLAPSSKSTSGGTAALGCLVKDYFP
EPVTVSWNSGALTSGVHTFPAVLQSSGLYSLSSWTVPSSSLGTQTYICNVNHKPSNTKVDKKVEPKSCDKTHTCPPC
PAPELLGGPSVFLFPPKPKDTLMISRTPEVTCVVVDVSHEDPEVKFNWYVDGVEVHNAKTKPREEQYNSTYRVVSVLT
VLHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK -continued

| Sequencing List |
| --- |

SEQ ID No. 9: Ab0001-LCCT-HCCT Light chain:
DIQMTQSPSSLSASVGDRVTITCRASQDVNTAVAWYQQKPGKAPKLLIYSASFLYSGVPSRFSGSRSGTDFTLTISSLQ
PEDFATYYCQQHYTTPPTFGQGTKVEIKRTVAAPSVFIFPPSDEQLKSGTASWCLLNNFYPREAKVQWKVDNALQS
GNSQESVTEQDSKDSTYSLSSTLTLSKADYEKHKVYACEVTHQGLSSPVTKSFNRGECLPETGG SEQ ID No. 10: Ab0001-LCCT-HCCT Heavy chain:
EVQLVESGGGLVQPGGSLRLSCAASGFNIKDTYIHWVRQAPGKGLEWVARIYPTNGYTRYADSVKGRFTISADTSKNT
AYLQMNSLRAEDTAVYYCSRWGGDGFYAMDYWGQGTLVTVSSASTKGPSVFPLAPSSKSTSGGTAALGCLVKDYFP
EPVTVSWNSGALTSGVHTFPAVLQSSGLYSLSSWTVPSSSLGTQTYICNVNHKPSNTKVDKKVEPKSCDKTHTCPPC
PAPELLGGPSVFLFPPKPKDTLMISRTPEVTCVVVDVSHEDPEVKFNWYVDGVEVHNAKTKPREEQYNSTYRVVSVLT
VLHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGKLPETGG SEQ ID No. 11: Ab0001-LCCT-HCCT$_L$ Light chain:
DIQMTQSPSSLSASVGDRVTITCRASQDVNTAVAWYQQKPGKAPKLLIYSASFLYSGVPSRFSGSRSGTDFTLTISSLQ
PEDFATYYCQQHYTTPPTFGQGTKVEIKRTVAAPSVFIFPPSDEQLKSGTASWCLLNNFYPREAKVQWKVDNALQS
GNSQESVTEQDSKDSTYSLSSTLTLSKADYEKHKVYACEVTHQGLSSPVTKSFNRGECLPETGG SEQ ID No. 12: Ab0001-LCCT-HCCT$_L$ Heavy chain:
EVQLVESGGGLVQPGGSLRLSCAASGFNIKDTYIHWVRQAPGKGLEWVARIYPTNGYTRYADSVKGRFTISADTSKNT
AYLQMNSLRAEDTAVYYCSRWGGDGFYAMDYWGQGTLVTVSSASTKGPSVFPLAPSSKSTSGGTAALGCLVKDYFP
EPVTVSWNSGALTSGVHTFPAVLQSSGLYSLSSWTVPSSSLGTQTYICNVNHKPSNTKVDKKVEPKSCDKTHTCPPC
PAPELLGGPSVFLFPPKPKDTLMISRTPEVTCVVVDVSHEDPEVKFNWYVDGVEVHNAKTKPREEQYNSTYRVVSVLT
VLHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGKGALPETGG SEQ ID No. 13: Ab0001-LCCT$_L$-HCCT Light chain:
DIQMTQSPSSLSASVGDRVTITCRASQDVNTAVAWYQQKPGKAPKLLIYSASFLYSGVPSRFSGSRSGTDFTLTISSLQ
PEDFATYYCQQHYTTPPTFGQGTKVEIKRTVAAPSVFIFPPSDEQLKSGTASWCLLNNFYPREAKVQWKVDNALQS
GNSQESVTEQDSKDSTYSLSSTLTLSKADYEKHKVYACEVTHQGLSSPVTKSFNRGECGALPETGG SEQ ID No. 14: Ab0001-LCCT$_L$-HCCT Heavy chain:
EVQLVESGGGLVQPGGSLRLSCAASGFNIKDTYIHWVRQAPGKGLEWVARIYPTNGYTRYADSVKGRFTISADTSKNT
AYLQMNSLRAEDTAVYYCSRWGGDGFYAMDYWGQGTLVTVSSASTKGPSVFPLAPSSKSTSGGTAALGCLVKDYFP
EPVTVSWNSGALTSGVHTFPAVLQSSGLYSLSSVVTVPSSSLGTQTYICNVNHKPSNTKVDKKVEPKSCDKTHTCPPC
PAPELLGGPSVFLFPPKPKDTLMISRTPEVTCVVVDVSHEDPEVKFNWYVDGVEVHNAKTKPREEQYNSTYRVVSVLT
VLHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGKLPETGG SEQ ID No. 15: Ab0001-LCCT$_L$-HCCT$_L$ Light chain:
DIQMTQSPSSLSASVGDRVTITCRASQDVNTAVAWYQQKPGKAPKLLIYSASFLYSGVPSRFSGSRSGTDFTLTISSLQ
PEDFATYYCQQHYTTPPTFGQGTKVEIKRTVAAPSVFIFPPSDEQLKSGTASWCLLNNFYPREAKVQWKVDNALQS
GNSQESVTEQDSKDSTYSLSSTLTLSKADYEKHKVYACEVTHQGLSSPVTKSFNRGECGALPETGG SEQ ID No. 16: Ab0001-LCCT$_L$-HCCT$_L$ Heavy chain:
EVQLVESGGGLVQPGGSLRLSCAASGFNIKDTYIHWVRQAPGKGLEWVARIYPTNGYTRYADSVKGRFTISADTSKNT
AYLQMNSLRAEDTAVYYCSRWGGDGFYAMDYWGQGTLVTVSSASTKGPSVFPLAPSSKSTSGGTAALGCLVKDYFP
EPVTVSWNSGALTSGVHTFPAVLQSSGLYSLSSWTVPSSSLGTQTYICNVNHKPSNTKVDKKVEPKSCDKTHTCPPC
PAPELLGGPSVFLFPPKPKDTLMISRTPEVTCVVVDVSHEDPEVKFNWYVDGVEVHNAKTKPREEQYNSTYRVVSVLT
VLHQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGKGALPETGG SEQ ID No. 17: Ab0064 Light chain
DIQMTQSPSSLSASVGDRVTITCKASQGINNYLSWYQQKPGKAPKSLIYRANRLVSGVPSRFSGSGSGTDFTLTISSLQ
PEDFATYYCLQYDEFPLTFGGGTKVEIKRTVAAPSVFIFPPSDEQLKSGTASWVCLLNNFYPREAKVQWKVDNALQSG
NSQESVTEQDSKDSTYSLSSTLTLSKADYEKHKVYACEVTHQGLSSPVTKSFNRGEC SEQ ID No. 18: Ab0064 Heavy chain
QVQLVQSGAEVKKPGSSVKVSCKASGYRFTDYVINWVRQAPGQGLEWMGQIYPGSDTFHYNQKFQGRATLTADKS
TNTAYMELSSLRSEDTAVYYCARFFEGLAYWGQGTLVTVSSASTKGPSVFPLAPSSKSTSGGTAALGCLVKDYFPEPVT
VSWNSGALTSGVHTFPAVLQSSGLYSLSSVVTVPSSSLGTQTYICNVNHKPSNTKVDKKVEPKSCDKTHTCPPCPAPE
LLGGPSVFLFPPKPKDTLMISRTPEVTCVVVDVSHEDPEVKFNWYVDGVEVHNAKTKPREEQYNSTYRVVSVLTVLHQ
DWLNGKEYKCKVSNKALPAPIEKTISKAKGQPREPQVYTLPPSREEMTKNQVSLTCLVKGFYPSDIAVEWESNGQPEN
NYKTTPPVLDSDGSFFLYSKLTVDKSRWQQGNVFSCSVMHEALHNHYTQKSLSLSPGK SEQ ID No. 19: Ab0064-LCCT$_L$-HC Light chain
DIQMTQSPSSLSASVGDRVTITCKASQGINNYLSWYQQKPGKAPKSLIYRANRLVSGVPSRFSGSGSGTDFTLTISSLQ
PEDFATYYCLQYDEFPLTFGGGTKVEIKRTVAAPSVFIFPPSDEQLKSGTASWVCLLNNFYPREAKVQWKVDNALQSG
NSQESVTEQDSKDSTYSLSSTLTLSKADYEKHKVYACEVTHQGLSSPVTKSFNRGECGALPETGG SEQ ID No. 20: Ab0064-LCCT$_L$-HC Heavy chain
QVQLVQSGAEVKKPGSSVKVSCKASGYRFTDYVINWVRQAPGQGLEWMGQIYPGSDTFHYNQKFQGRATLTADKS
TNTAYMELSSLRSEDTAVYYCARFFEGLAYWGQGTLVTVSSASTKGPSVFPLAPSSKSTSGGTAALGCLVKDYFPEPVT
VSWNSGALTSGVHTFPAVLQSSGLYSLSSVVTVPSSSLGTQTYICNVNHKPSNTKVDKKVEPKSCDKTHTCPPCPAPE -continued

| Sequencing List |
| --- |
| LLGGPSVFLFPPKPKDTLMISRTPEVTCVVVDVSHEDPEVKFNWYVDGVEVHNAKTKPREEQYNSTYRVVSVLTVLHQ<br>DWLNGKEYKCKVSNKALPAPIEKTISKAKGQPREPQVYTLPPSREEMTKNQVSLTCLVKGFYPSDIAVEWESNGQPEN<br>NYKTTPPVLDSDGSFFLYSKLTVDKSRWQQGNVFSCSVMHEALHNHYTQKSLSLSPGK |
| SEQ ID No. 21: Ab0098 Light chain<br>DIVMTQSPSSLTVTAGEKVTMSCKSSQSLLNSGNQKNYLTWYQQKPGQPPKLLIYWASTRESGVPDRFTGSGSGTDF<br>TLTISSVQAEDLAVYYCQNDYSYPFTFGSGTKLEIKRTVAAPSVFIFPPSDEQLKSGTASWCLLNNFYPREAKVQWKV<br>DNALQSGNSQESVTEQDSKDSTYSLSSTLTLSKADYEKHKVYACEVTHQGLSSPVTKSFNRGEC |
| SEQ ID No. 22: Ab0098 Heavy chain<br>QVQLQQPGAELVRPGASVKLSCKASGYTFTSYWINWVKQRPGQGLEWIGNIYPSDSYTNYNQKFKDKATLTVDKSS<br>STAYMQLSSPTSEDSAVYYCTRSWRGNSFDYWGQGTTLTVSSASTKGPSVFPLAPSSKSTSGGTAALGCLVKDYFPEP<br>VTVSWNSGALTSGVHTFPAVLQSSGLYSLSSVVTVPSSSLGTQTYICNVNHKPSNTKVDKRVEPKSCDKTHTCPPCPA<br>PELLGGPSVFLFPPKPKDTLMISRTPEVTCVVVDVSHEDPEVKFNWYVDGVEVHNAKTKPREEQYNSTYRVVSVLTVL<br>HQDWLNGKEYKCKVSNKALPAPIEKTISKAKGQPREPQVYTLPPSREEMTKNQVSLTCLVKGFYPSDIAVEWESNGQ<br>PENNYKTTPPVLDSDGSFFLYSKLTVDKSRWQQGNVFSCSVMHEALHNHYTQKSLSLSPGK |
| SEQ ID No. 23: Ab0098-LCCT$_L$-HC Light chain<br>DIVMTQSPSSLTVTAGEKVTMSCKSSQSLLNSGNQKNYLTWYQQKPGQPPKLLIYWASTRESGVPDRFTGSGSGTDF<br>TLTISSVQAEDLAVYYCQNDYSYPFTFGSGTKLEIKRTVAAPSVFIFPPSDEQLKSGTASWCLLNNFYPREAKVQWKV<br>DNALQSGNSQESVTEQDSKDSTYSLSSTLTLSKADYEKHKVYACEVTHQGLSSPVTKSFNRGECGALPETGG |
| SEQ ID No. 24: Ab0098-LCCT$_L$-HC Heavy chain<br>QVQLQQPGAELVRPGASVKLSCKASGYTFTSYWINWVKQRPGQGLEWIGNIYPSDSYTNYNQKFKDKATLTVDKSS<br>STAYMQLSSPTSEDSAVYYCTRSWRGNSFDYWGQGTTLTVSSASTKGPSVFPLAPSSKSTSGGTAALGCLVKDYFPEP<br>VTVSWNSGALTSGVHTFPAVLQSSGLYSLSSVVTVPSSSLGTQTYICNVNHKPSNTKVDKRVEPKSCDKTHTCPPCPA<br>PELLGGPSVFLFPPKPKDTLMISRTPEVTCVVVDVSHEDPEVKFNWYVDGVEVHNAKTKPREEQYNSTYRVVSVLTVL<br>HQDWLNGKEYKCKVSNKALPAPIEKTISKAKGQPREPQVYTLPPSREEMTKNQVSLTCLVKGFYPSDIAVEWESNGQ<br>PENNYKTTPPVLDSDGSFFLYSKLTVDKSRWQQGNVFSCSVMHEALHNHYTQKSLSLSPGK |

SEQUENCE LISTING

```
Sequence total quantity: 32
SEQ ID NO: 1            moltype = AA  length = 222
FEATURE                 Location/Qualifiers
REGION                  1..222
                        note = Ab0001-LCCTL-HC Light chain
source                  1..222
                        mol_type = protein
                        organism = synthetic construct
SEQUENCE: 1
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ HYTTPPTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGECGALPET GG                     222

SEQ ID NO: 2            moltype = AA  length = 450
FEATURE                 Location/Qualifiers
REGION                  1..450
                        note = Ab0001-LCCTL-HC Heavy chain
source                  1..450
                        mol_type = protein
                        organism = synthetic construct
SEQUENCE: 2
EVQLVESGGG LVQPGGSLRL SCAASGFNIK DTYIHWVRQA PGKGLEWVAR IYPTNGYTRY  60
ADSVKGRFTI SADTSKNTAY LQMNSLRAED TAVYYCSRWG GDGFYAMDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSREE  360
MTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                   450

SEQ ID NO: 3            moltype = AA  length = 214
FEATURE                 Location/Qualifiers
REGION                  1..214
                        note = Ab0001-LC-HCCT Light chain
source                  1..214
                        mol_type = protein
                        organism = synthetic construct
SEQUENCE: 3
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ HYTTPPTFGQ GTKVEIKRTV AAPSVFIFPP  120
```

```
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 4           moltype = AA  length = 456
FEATURE                Location/Qualifiers
REGION                 1..456
                       note = Ab0001-LC-HCCT Heavy chain
source                 1..456
                       mol_type = protein
                       organism = synthetic construct
SEQUENCE: 4
EVQLVESGGG LVQPGGSLRL SCAASGFNIK DTYIHWVRQA PGKGLEWVAR IYPTNGYTRY  60
ADSVKGRFTI SADTSKNTAY LQMNSLRAED TAVYYCSRWG GDGFYAMDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSREE  360
MTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK LPETGG                            456

SEQ ID NO: 5           moltype = AA  length = 214
FEATURE                Location/Qualifiers
REGION                 1..214
                       note = Ab0001-LC-HCCTL Light chain
source                 1..214
                       mol_type = protein
                       organism = synthetic construct
SEQUENCE: 5
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ HYTTPPTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 6           moltype = AA  length = 458
FEATURE                Location/Qualifiers
REGION                 1..458
                       note = Ab0001-LC-HCCTL Heavy chain
source                 1..458
                       mol_type = protein
                       organism = synthetic construct
SEQUENCE: 6
EVQLVESGGG LVQPGGSLRL SCAASGFNIK DTYIHWVRQA PGKGLEWVAR IYPTNGYTRY  60
ADSVKGRFTI SADTSKNTAY LQMNSLRAED TAVYYCSRWG GDGFYAMDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSREE  360
MTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK GALPETGG                          458

SEQ ID NO: 7           moltype = AA  length = 220
FEATURE                Location/Qualifiers
REGION                 1..220
                       note = Ab0001-LCCT-HC Light chain
source                 1..220
                       mol_type = protein
                       organism = synthetic construct
SEQUENCE: 7
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ HYTTPPTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGECLPETGG                        220

SEQ ID NO: 8           moltype = AA  length = 450
FEATURE                Location/Qualifiers
REGION                 1..450
                       note = Ab0001-LCCT-HC Heavy chain
source                 1..450
                       mol_type = protein
                       organism = synthetic construct
SEQUENCE: 8
EVQLVESGGG LVQPGGSLRL SCAASGFNIK DTYIHWVRQA PGKGLEWVAR IYPTNGYTRY  60
ADSVKGRFTI SADTSKNTAY LQMNSLRAED TAVYYCSRWG GDGFYAMDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSREE  360
MTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                   450
```

```
SEQ ID NO: 9            moltype = AA  length = 220
FEATURE                 Location/Qualifiers
REGION                  1..220
                        note = Ab0001-LCCT-HCCT Light chain
source                  1..220
                        mol_type = protein
                        organism = synthetic construct
SEQUENCE: 9
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ HYTTPPTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGECLPETGG                       220

SEQ ID NO: 10           moltype = AA  length = 456
FEATURE                 Location/Qualifiers
REGION                  1..456
                        note = Ab0001-LCCT-HCCT Heavy chain
source                  1..456
                        mol_type = protein
                        organism = synthetic construct
SEQUENCE: 10
EVQLVESGGG LVQPGGSLRL SCAASGFNIK DTYIHWVRQA PGKGLEWVAR IYPTNGYTRY  60
ADSVKGRFTI SADTSKNTAY LQMNSLRAED TAVYYCSRWG GDGFYAMDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSREE  360
MTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK LPETGG                           456

SEQ ID NO: 11           moltype = AA  length = 220
FEATURE                 Location/Qualifiers
REGION                  1..220
                        note = Ab0001-LCCT-HCCTL Light chain
source                  1..220
                        mol_type = protein
                        organism = synthetic construct
SEQUENCE: 11
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ HYTTPPTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGECLPETGG                       220

SEQ ID NO: 12           moltype = AA  length = 458
FEATURE                 Location/Qualifiers
REGION                  1..458
                        note = Ab0001-LCCT-HCCTL Heavy chain
source                  1..458
                        mol_type = protein
                        organism = synthetic construct
SEQUENCE: 12
EVQLVESGGG LVQPGGSLRL SCAASGFNIK DTYIHWVRQA PGKGLEWVAR IYPTNGYTRY  60
ADSVKGRFTI SADTSKNTAY LQMNSLRAED TAVYYCSRWG GDGFYAMDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSREE  360
MTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK GALPETGG                         458

SEQ ID NO: 13           moltype = AA  length = 222
FEATURE                 Location/Qualifiers
REGION                  1..222
                        note = Ab0001-LCCTL-HCCT Light chain
source                  1..222
                        mol_type = protein
                        organism = synthetic construct
SEQUENCE: 13
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ HYTTPPTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGECGALPET GG                    222

SEQ ID NO: 14           moltype = AA  length = 456
FEATURE                 Location/Qualifiers
REGION                  1..456
                        note = Ab0001-LCCTL-HCCT Heavy chain
source                  1..456
```

```
                         mol_type = protein
                         organism = synthetic construct
SEQUENCE: 14
EVQLVESGGG LVQPGGSLRL SCAASGFNIK DTYIHWVRQA PGKGLEWVAR IYPTNGYTRY  60
ADSVKGRFTI SADTSKNTAY LQMNSLRAED TAVYYCSRWG GDGFYAMDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSREE  360
MTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK LPETGG                            456

SEQ ID NO: 15            moltype = AA  length = 222
FEATURE                  Location/Qualifiers
REGION                   1..222
                         note = Ab0001-LCCTL-HCCTL Light chain
source                   1..222
                         mol_type = protein
                         organism = synthetic construct
SEQUENCE: 15
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ HYTTPPTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGECGALPET GG                    222

SEQ ID NO: 16            moltype = AA  length = 458
FEATURE                  Location/Qualifiers
REGION                   1..458
                         note = Ab0001-LCCTL-HCCTL Heavy chain
source                   1..458
                         mol_type = protein
                         organism = synthetic construct
SEQUENCE: 16
EVQLVESGGG LVQPGGSLRL SCAASGFNIK DTYIHWVRQA PGKGLEWVAR IYPTNGYTRY  60
ADSVKGRFTI SADTSKNTAY LQMNSLRAED TAVYYCSRWG GDGFYAMDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSREE  360
MTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK GALPETGG                          458

SEQ ID NO: 17            moltype = AA  length = 214
FEATURE                  Location/Qualifiers
REGION                   1..214
                         note = Ab0064 Light chain
source                   1..214
                         mol_type = protein
                         organism = synthetic construct
SEQUENCE: 17
DIQMTQSPSS LSASVGDRVT ITCKASQGIN NYLSWYQQKP GKAPKSLIYR ANRLVSGVPS  60
RFSGSGSGTD FTLTISSLQP EDFATYYCLQ YDEFPLTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 18            moltype = AA  length = 446
FEATURE                  Location/Qualifiers
REGION                   1..446
                         note = Ab0064 Heavy chain
source                   1..446
                         mol_type = protein
                         organism = synthetic construct
SEQUENCE: 18
QVQLVQSGAE VKKPGSSVKV SCKASGYRFT DYVINWVRQA PGQGLEWMGQ IYPGSDTFHY  60
NQKFQGRATL TADKSTNTAY MELSSLRSED TAVYYCARFF EGLAYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKKVEPKSCD KTHTCPPCPA PELLGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPGK                                      446

SEQ ID NO: 19            moltype = AA  length = 222
FEATURE                  Location/Qualifiers
REGION                   1..222
                         note = Ab0064-LCCTL-HC Light chain
source                   1..222
                         mol_type = protein
                         organism = synthetic construct
```

-continued

```
SEQUENCE: 19
DIQMTQSPSS LSASVGDRVT ITCKASQGIN NYLSWYQQKP GKAPKSLIYR ANRLVSGVPS  60
RFSGSGSGTD FTLTISSLQP EDFATYYCLQ YDEFPLTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGECGALPET GG                    222

SEQ ID NO: 20          moltype = AA  length = 446
FEATURE                Location/Qualifiers
REGION                 1..446
                       note = Ab0064-LCCTL-HC Heavy chain
source                 1..446
                       mol_type = protein
                       organism = synthetic construct
SEQUENCE: 20
QVQLVQSGAE VKKPGSSVKV SCKASGYRFT DYVINWVRQA PGQGLEWMGQ IYPGSDTFHY  60
NQKFQGRATL TADKSTNTAY MELSSLRSED TAVYYCARFF EGLAYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKKVEPKSCD KTHTCPPCPA PELLGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPGK                                      446

SEQ ID NO: 21          moltype = AA  length = 220
FEATURE                Location/Qualifiers
REGION                 1..220
                       note = Ab0098 Light chain
source                 1..220
                       mol_type = protein
                       organism = synthetic construct
SEQUENCE: 21
DIVMTQSPSS LTVTAGEKVT MSCKSSQSLL NSGNQKNYLT WYQQKPGQPP KLLIYWASTR  60
ESGVPDRFTG SGSGTDFTLT ISSVQAEDLA VYYCQNDYSY PFTFGSGTKL EIKRTVAAPS  120
VFIFPPSDEQ LKSGTASVVC LLNNFYPREA KVQWKVDNAL QSGNSQESVT EQDSKDSTYS  180
LSSTLTLSKA DYEKHKVYAC EVTHQGLSSP VTKSFNRGEC                        220

SEQ ID NO: 22          moltype = AA  length = 448
FEATURE                Location/Qualifiers
REGION                 1..448
                       note = Ab0098 Heavy chain
source                 1..448
                       mol_type = protein
                       organism = synthetic construct
SEQUENCE: 22
QVQLQQPGAE LVRPGASVKL SCKASGYTFT SYWINWVKQR PGQGLEWIGN IYPSDSYTNY  60
NQKFKDKATL TVDKSSSTAY MQLSSPTSED SAVYYCTRSW RGNSFDYWGQ GTTLTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKRVEPKS CDKTHTCPPC PAPELLGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSREEMT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPGK                                    448

SEQ ID NO: 23          moltype = AA  length = 228
FEATURE                Location/Qualifiers
REGION                 1..228
                       note = Ab0098- LCCTL-HC Light chain
source                 1..228
                       mol_type = protein
                       organism = synthetic construct
SEQUENCE: 23
DIVMTQSPSS LTVTAGEKVT MSCKSSQSLL NSGNQKNYLT WYQQKPGQPP KLLIYWASTR  60
ESGVPDRFTG SGSGTDFTLT ISSVQAEDLA VYYCQNDYSY PFTFGSGTKL EIKRTVAAPS  120
VFIFPPSDEQ LKSGTASVVC LLNNFYPREA KVQWKVDNAL QSGNSQESVT EQDSKDSTYS  180
LSSTLTLSKA DYEKHKVYAC EVTHQGLSSP VTKSFNRGEC GALPETGG              228

SEQ ID NO: 24          moltype = AA  length = 448
FEATURE                Location/Qualifiers
REGION                 1..448
                       note = Ab0098- LCCTL-HC Heavy chain
source                 1..448
                       mol_type = protein
                       organism = synthetic construct
SEQUENCE: 24
QVQLQQPGAE LVRPGASVKL SCKASGYTFT SYWINWVKQR PGQGLEWIGN IYPSDSYTNY  60
NQKFKDKATL TVDKSSSTAY MQLSSPTSED SAVYYCTRSW RGNSFDYWGQ GTTLTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKRVEPKS CDKTHTCPPC PAPELLGGPS  240
VFLFPPKPKD TLMISRTPEV TCVVVDVSHE DPEVKFNWYV DGVEVHNAKT KPREEQYNST  300
```

-continued

```
YRVVSVLTVL HQDWLNGKEY KCKVSNKALP APIEKTISKA KGQPREPQVY TLPPSREEMT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPGK                                     448

SEQ ID NO: 25          moltype = AA  length = 5
FEATURE                Location/Qualifiers
REGION                 1..5
                       note = Spacer sequence
source                 1..5
                       mol_type = protein
                       organism = synthetic construct
SEQUENCE: 25
GGGGS                                                              5

SEQ ID NO: 26          moltype = AA  length = 10
FEATURE                Location/Qualifiers
REGION                 1..10
                       note = Spacer sequence
source                 1..10
                       mol_type = protein
                       organism = synthetic construct
SEQUENCE: 26
GGGGSGGGGS                                                         10

SEQ ID NO: 27          moltype = AA  length = 15
FEATURE                Location/Qualifiers
REGION                 1..15
                       note = Spacer sequence
source                 1..15
                       mol_type = protein
                       organism = synthetic construct
SEQUENCE: 27
GGGGSGGGGS GGGGS                                                   15

SEQ ID NO: 28          moltype = AA  length = 8
FEATURE                Location/Qualifiers
REGION                 1..8
                       note = Sequence introduced at the terminal
source                 1..8
                       mol_type = protein
                       organism = synthetic construct
SEQUENCE: 28
GALPETGG                                                           8

SEQ ID NO: 29          moltype = AA  length = 6
FEATURE                Location/Qualifiers
REGION                 1..6
                       note = Sequence introduced at the terminal
source                 1..6
                       mol_type = protein
                       organism = synthetic construct
SEQUENCE: 29
LPETGG                                                             6

SEQ ID NO: 30          moltype = AA  length = 4
FEATURE                Location/Qualifiers
REGION                 1..4
                       note = Sequence contained in linking unit fragment LU105
source                 1..4
                       mol_type = protein
                       organism = synthetic construct
SEQUENCE: 30
GGGC                                                               4

SEQ ID NO: 31          moltype = AA  length = 4
FEATURE                Location/Qualifiers
REGION                 1..4
                       note = Sequence contained in linking unit fragment LU107
source                 1..4
                       mol_type = protein
                       organism = synthetic construct
SEQUENCE: 31
GGGL                                                               4

SEQ ID NO: 32          moltype = AA  length = 4
FEATURE                Location/Qualifiers
REGION                 1..4
                       note = Sequence contained in linking unit fragment LU108
source                 1..4
```

-continued

```
                    mol_type = protein
                    organism = synthetic construct
SEQUENCE: 32
GGGQ                                                              4
```

The invention claimed is:

1. An antibody-drug conjugate of formula (II):

(II)

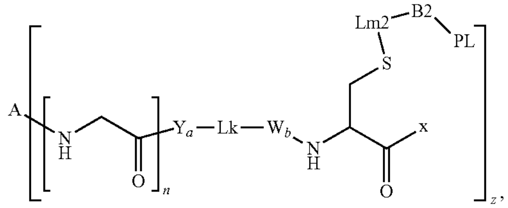

wherein:

n is an integer of 3 to 10;

Y and W are each independently absent or selected from PABC, a spacer comprising 1-10 amino acids, and a combination thereof;

a and b are each independently 0 or 1;

Lk is a combination of $L_1$-$L_2$-$L_3$;

$L_1$ and $L_3$ are each independently selected from: —$CH_2$—, —NH—, —C(O)—, —NHC(O)—, —C(O)NH—, and combination of a $C_{1-4}$ alkylene with one of the following groups: —$CH_2$—, —NH—, —C(O)—, —NHC(O)—, or —C(O)NH—;

$L_2$ is absent or is a $C_{7-34}$ alkylene, and wherein one or more (—$CH_2$—) structures in the alkylene is optionally replaced by —O—;

x is selected from hydrogen, OH, $NH_2$, an amino acid fragment comprising 1-10 amino acids, and a nucleotide fragment comprising 1-10 nucleotides;

Lm2 is

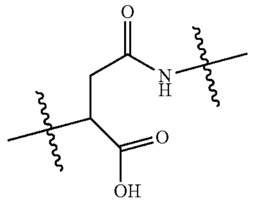,
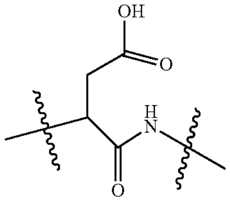, or a mixture thereof;

B2 is selected from the following group or their combination: —$(CH_2)_k$C(O)—, —$(CH_2)_k$C(O)-Val-Cit-PABC-, —$(CH_2)_k$C(O)-Val-Cit-PABC-(NH—$CR^1R^2$—C(O))$_d$—, —$(CH_2)_{k1}$C(O)—NH—($C_2H_4$—O)$_j$—$(CH_2)_{k2}$C(O)-Lys-, —$(CH_2)_k$C(O)—(NH—$CR^1R^2$—C(O))$_d$—NH—($C_2H_4$—O)$_j$—, and —$(CH_2)_k$C(O)—(NH—$CR^1R^2$—C(O))$_d$;

$R^1$ and $R^2$ are each independently selected from: hydrogen, —OH, —$NH_2$, —$C_{1-6}$ alkyl, —O—$C_{1-6}$ alkyl, —NH—$C_{1-6}$ alkyl, —$C_{1-6}$ alkyl-$NH_2$, —N($C_{1-6}$ alkyl)—$C_{1-6}$ alkyl, —$C_{1-6}$ alkyl-O—$C_{1-6}$ alkyl, —$C_{1-6}$ alkyl-NH—$C_{1-6}$ alkyl, —C(O)—$C_{1-6}$ alkyl, —NHC(O)—$C_{1-6}$ alkyl, —C(O)—$NH_2$, —C(O)NH—$C_{1-6}$ alkyl, —C(O)N($C_{1-6}$ alkyl)—$C_{1-6}$ alkyl, —S(=O)$_2$—$C_{1-6}$ alkyl, —NHS(=O)$_2$—$C_{1-6}$ alkyl, —S(=O)$_2$O—$C_{1-6}$ alkyl, —S(=O)$_2$NH—$C_{1-6}$ alkyl, and —S(=O)$_2$N ($C_{1-6}$ alkyl)—$C_{1-6}$ alkyl;

each k, k1, and k2 are independently an integer of 0 to 10;

d is an integer of 1 to 10;

j is an integer of 1 to 10;

PL is a payload which is an immune agonist, wherein the immune agonist has the structure of formula i:

Formula i

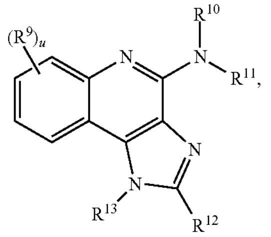

wherein:

each $R^9$ is independently selected from hydrogen, halogen, $C_{1-7}$ alkyl-OC(O)—$C_{1-7}$ alkyl, $C_{1-7}$ alkyl-OC(O)—$C_{2-7}$ alkenyl, and 5-7 membered heterocycle;

$R^{10}$ and $R^{11}$ are each independently selected from hydrogen and $C_{1-7}$ alkyl;

$R^{12}$ is selected from $C_{1-7}$ alkyl and $C_{1-7}$ alkoxy-$C_{1-7}$ alkyl;

$R^{13}$ is selected from $C_{1-7}$ alkyl, which is optionally substituted by a substituent selected from —OH and —$NH_2$; and u is 1, 2, 3 or 4;

or wherein the immune agonist has the structure of formula ii:

Formula ii

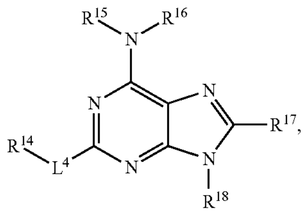

wherein:

$L^4$ is selected from —$CH_2$—, —NH—, —O—, and —C(O)—;

$R^{14}$ is selected from $C_{1-7}$ alkyl, $C_{1-7}$ alkoxy, and $C_{1-7}$ alkyl-OC(O)—$C_{1-7}$ alkyl;

$R^{15}$ and $R^{16}$ are each independently selected from hydrogen and $C_{1-7}$ alkyl;

$R^{17}$ is selected from —$NH_2$, —OH, $C_{1-7}$ alkyl, $C_{1-7}$ alkoxy, and —NH—$C_{1-7}$ alkyl; and $R^{18}$ is selected from —$CH_2$-aryl, and —$CH_2$-heteroaryl, wherein the aryl and the heteroaryl are each independently optionally substituted by a substituent selected from —C(O)OH and

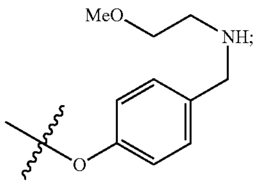 [SMILES: *Oc1ccc(CNCCOC)cc1]

or wherein the immune agonist has the structure of formula iii:

Formula iii

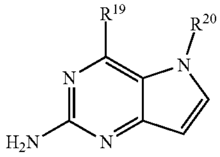

wherein:

$R^{19}$ is selected from —OH, —$NH_2$, $C_{1-7}$ alkyl, $C_{1-7}$ alkoxy, and —NH—$C_{1-7}$ alkyl; and $R^{20}$ is selected from —$CH_2$-aryl, wherein the aryl is optionally substituted by two substituents selected from —OH, $C_{1-7}$ alkoxy and —$C_{1-7}$ alkyl-piperidinyl;

or wherein the immune agonist has the structure of formula iv:

Formula iv

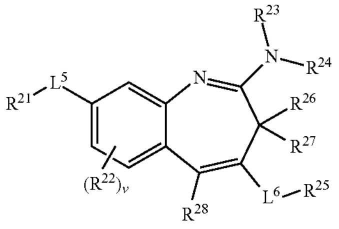

wherein:

$L_5$ is selected from —$CH_2$—, —NH—, —C(O)—, —NHC(O)—, and —C(O)NH—;

$R^{21}$ is selected from

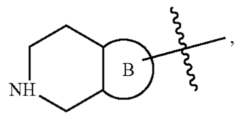

wherein B is a heteroaryl ring;

$R^{22}$ is selected from hydrogen and $C_{1-7}$ alkyl;

$R^{23}$ and $R^{24}$ are each independently selected from hydrogen and $C_{1-7}$ alkyl;

$L^6$ is selected from —$CH_2$— and —C(O)—;

$R^{25}$ is selected from —N($C_{1-7}$ alkyl)($C_{1-7}$ alkyl);

$R^{26}$, $R^{27}$, and $R^{28}$ are each independently selected from hydrogen and $C_{1-7}$ alkyl; and v is 1, 2 or 3;

z is an integer of 1 to 20; and

A is a targeting molecule which is an antibody or an antigen binding fragment.

2. The antibody-drug conjugate of claim 1, wherein Lk is $L^1$-$L^2$-$L^3$, $L^1$ is —NH—, $L^3$ is —C(O)—, $L^2$ is —($C_2H_4$—O)$_i$—$C_2H_4$—, and i is an integer of 2 to 10.

3. The antibody-drug conjugate of claim 2, wherein i is 4.

4. The antibody-drug conjugate of claim 1, wherein each k, k1, and k2 are independently 0, 1, or 2.

5. The antibody-drug conjugate of claim 1, wherein each k, k1, and k2 are independently 1 or 2.

6. The antibody-drug conjugate of claim 1, wherein Y and W are independently selected from leucine (Leu), glutamine (Gln), PABC, Phe-Lys-PABC, Val-Cit-PABC, and Val-Lys-PABC.

7. The antibody-drug conjugate of claim 1, wherein a and b are 0.

8. The antibody-drug conjugate of claim 1, wherein $R^1$ and $R^2$ are both methyl.

9. The antibody-drug conjugate of claim 1, wherein x is $NH_2$.

10. The antibody-drug conjugate of claim 1, wherein j is 1, 3, or 4.

11. The antibody-drug conjugate of claim 1, wherein the antibody-drug conjugate is selected from the following:

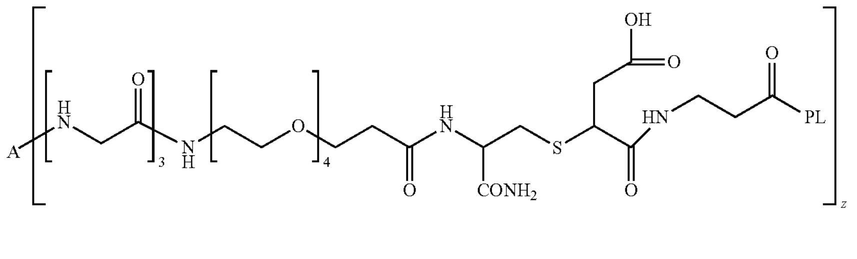

-continued
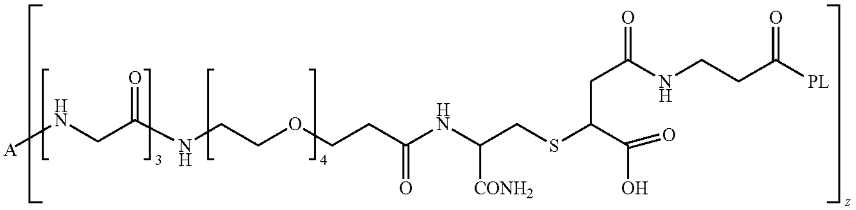
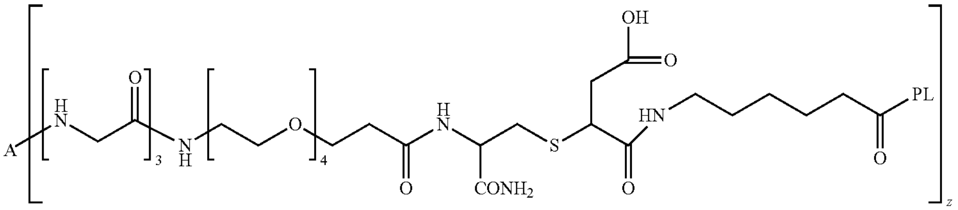
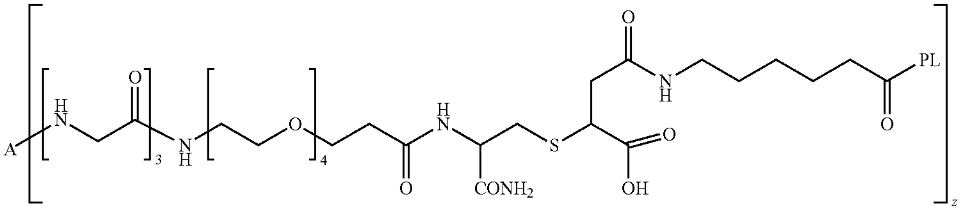
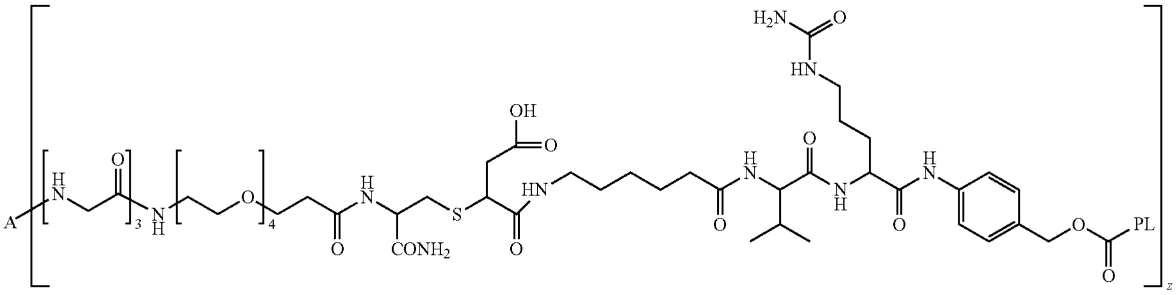
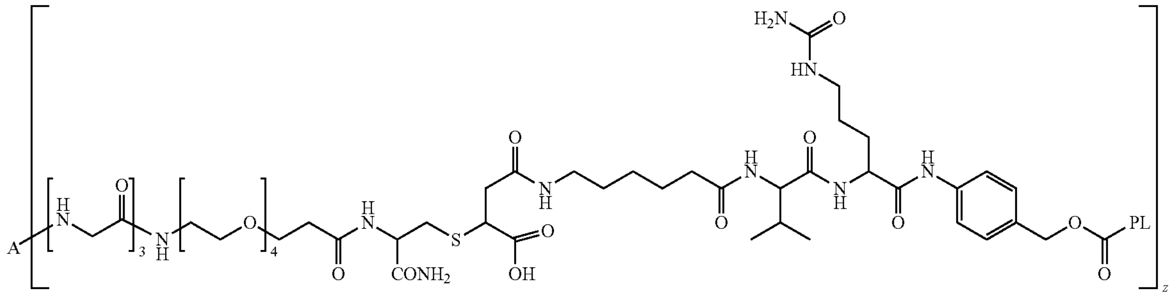
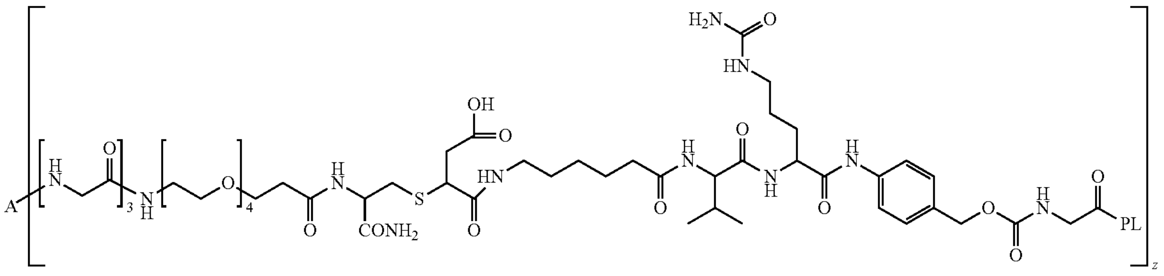

-continued
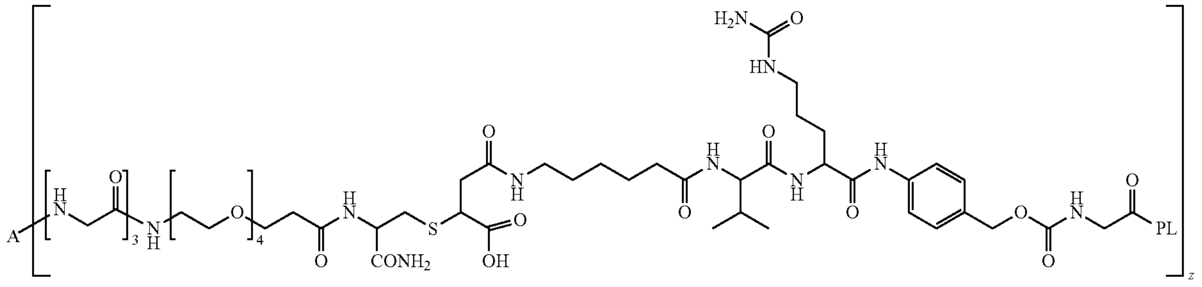
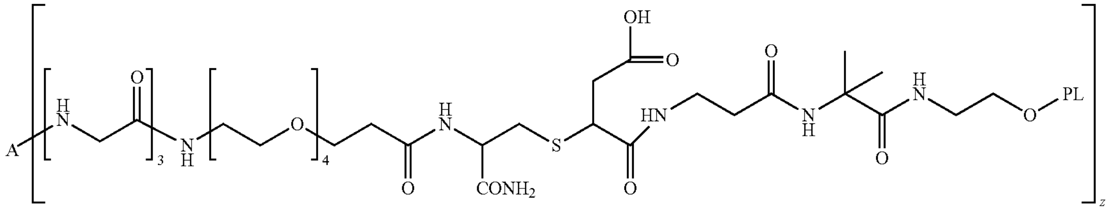
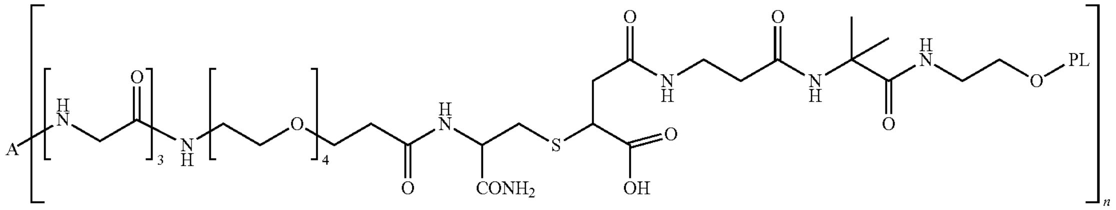
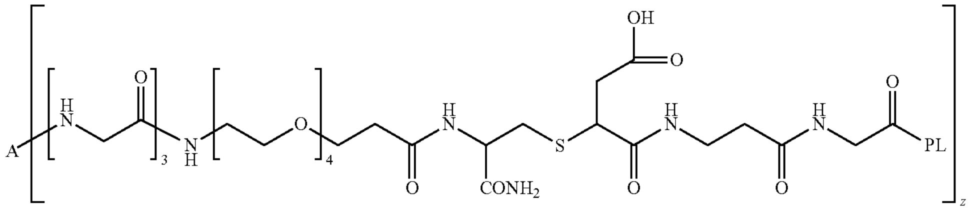
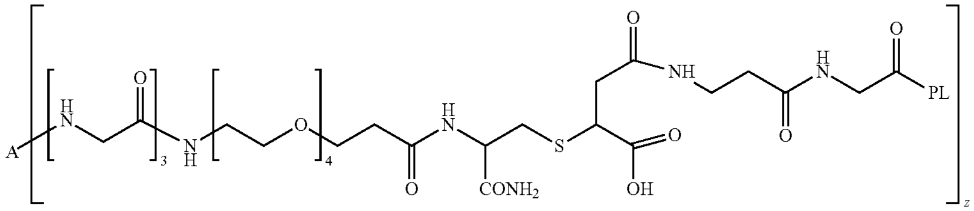
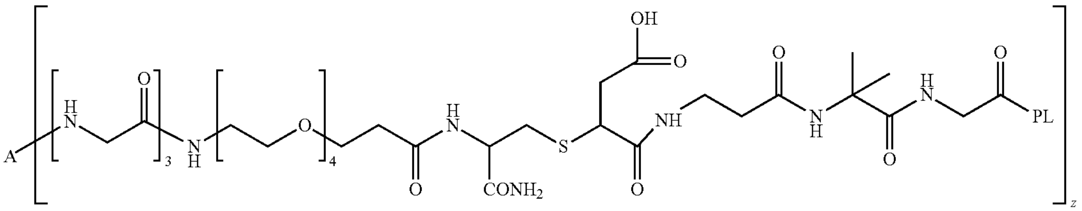
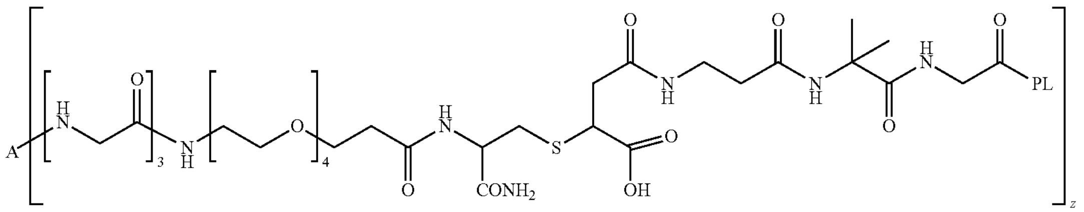
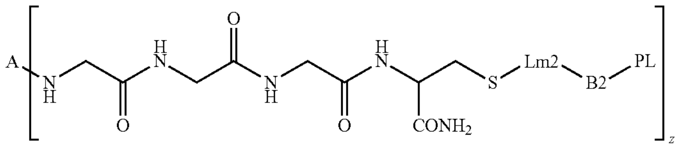

-continued
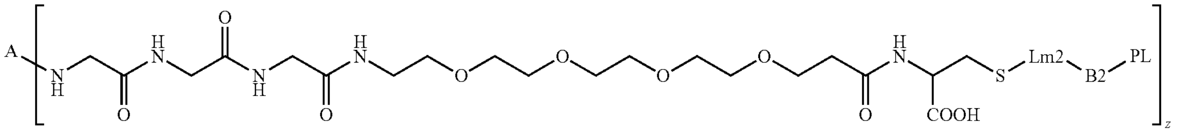
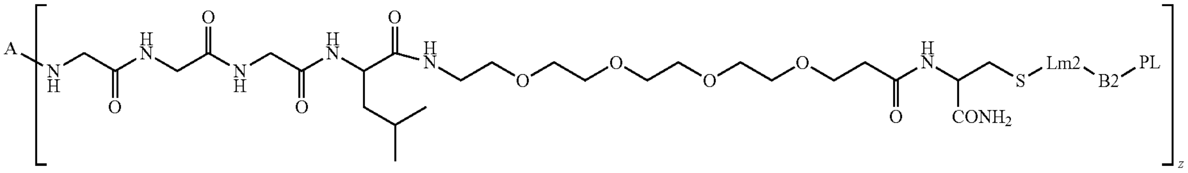
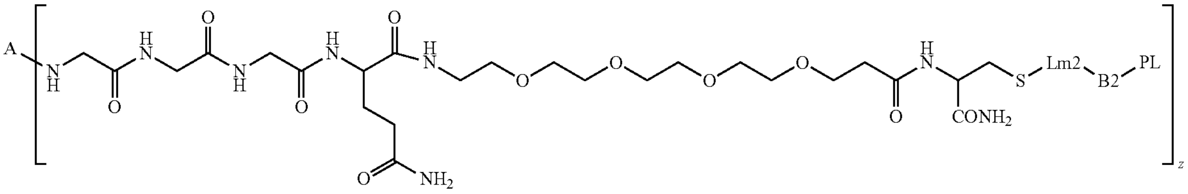
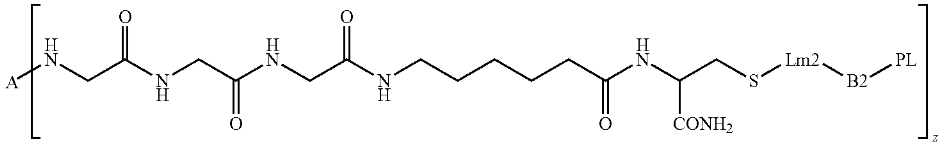
and
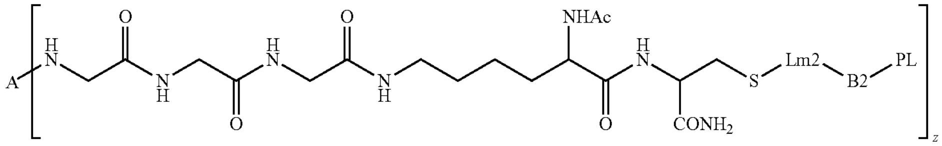
.
12. The antibody-drug conjugate of claim 1, wherein the antibody-drug conjugate is selected from the following:
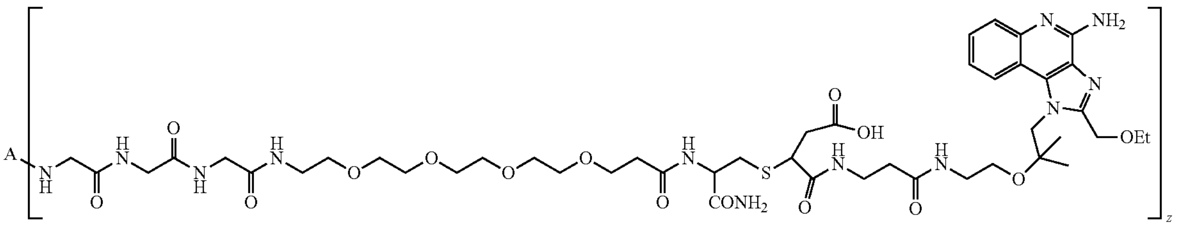
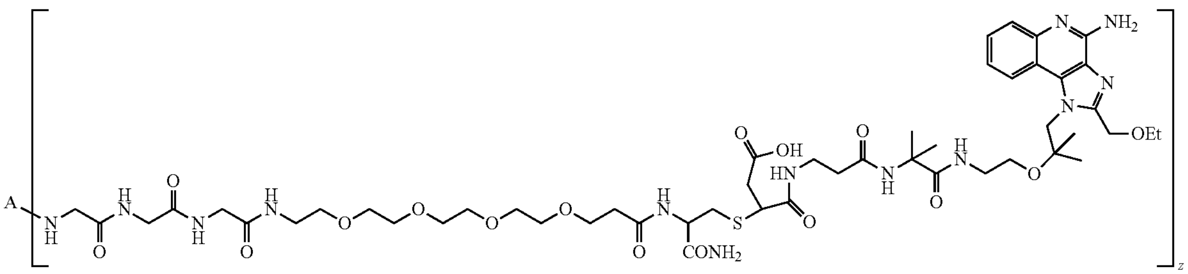
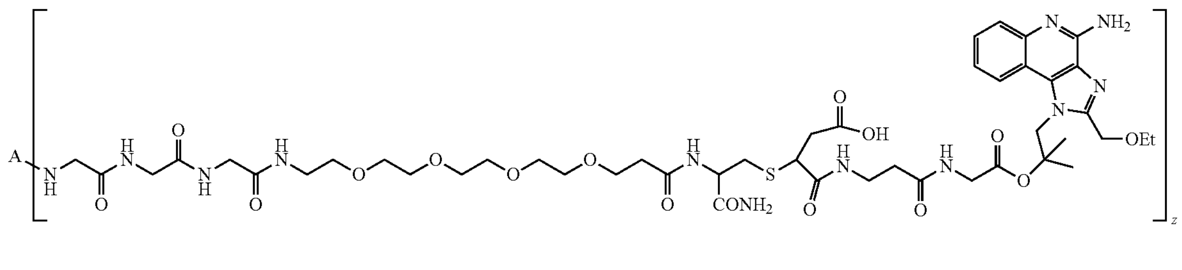

-continued
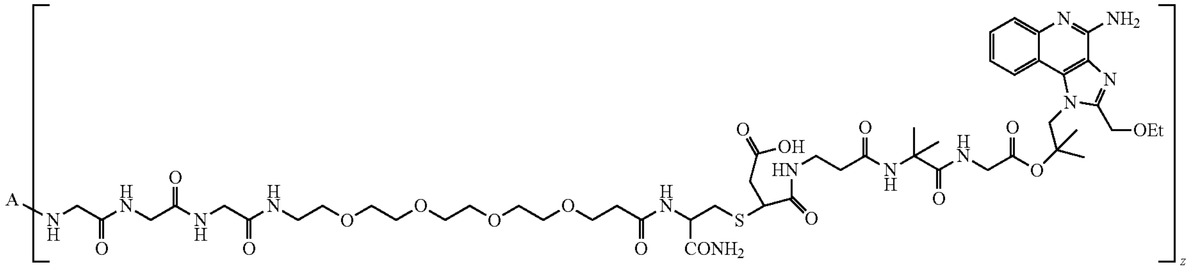
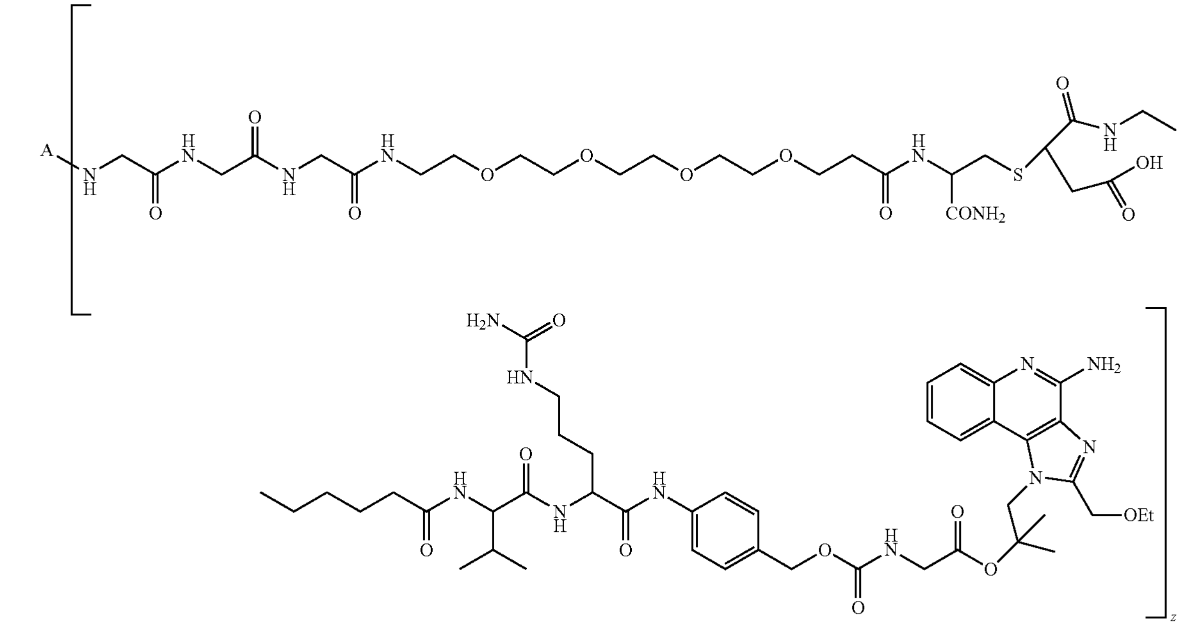
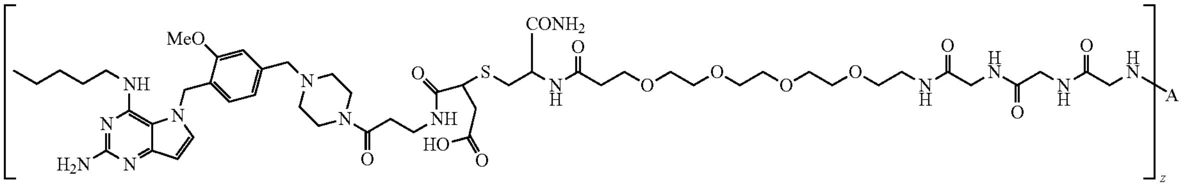
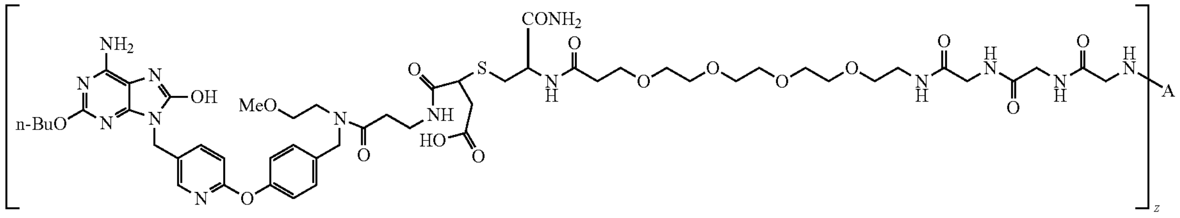
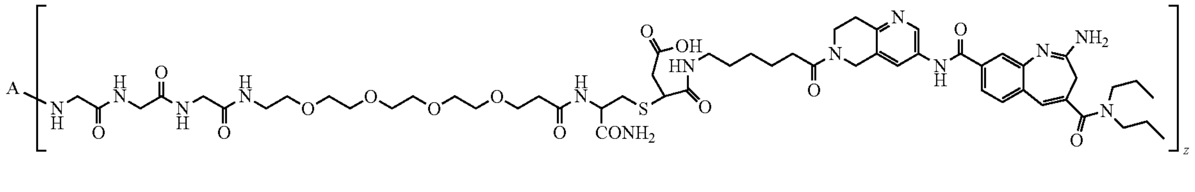

-continued

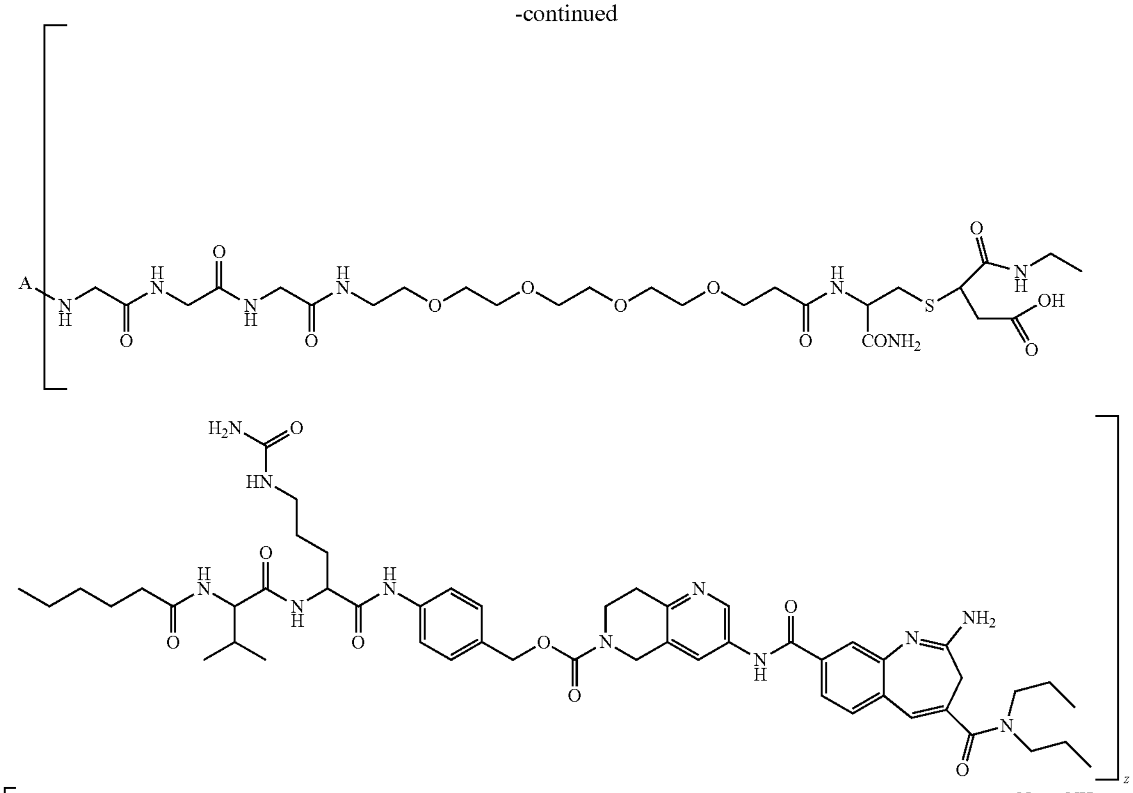

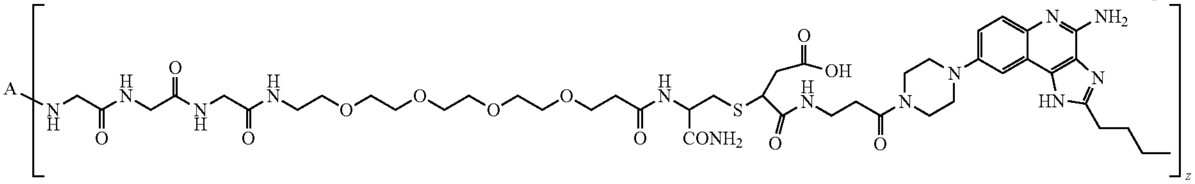

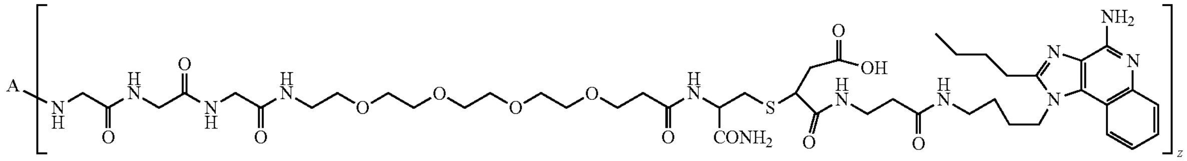

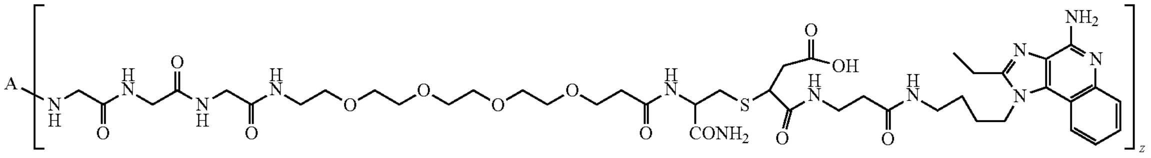

and

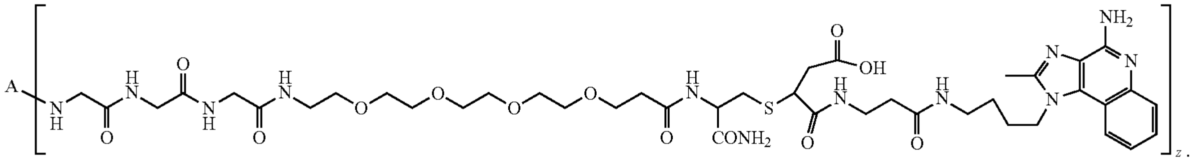

13. The antibody-drug conjugate of claim 1, wherein the immune agonist is selected from imidazoquinolines.

14. The antibody-drug conjugate of claim 1, wherein the antibody is an anti-human HER2 antibody.

15. The antibody-drug conjugate of claim 14, wherein the anti-human HER2 antibody comprises a light chain having the amino acid sequence of SEQ ID NO: 1 and comprises a heavy chain having the amino acid sequence of SEQ ID NO: 2; or comprises a light chain having the amino acid sequence of SEQ ID NO: 3 and comprises a heavy chain having the amino acid sequence of SEQ ID NO: 4; or comprises a light chain having the amino acid sequence of SEQ ID NO: 5 and comprises a heavy chain having the amino acid sequence of SEQ ID NO: 6; or comprises a light chain having the amino acid sequence of SEQ ID NO: 7 and comprises a heavy chain having the amino acid sequence of SEQ ID NO: 8; or comprises a light chain having the amino acid sequence of SEQ ID NO: 9 and comprises a heavy chain having the amino acid sequence of SEQ ID NO: 10; or comprises a light chain having the amino acid sequence of SEQ ID NO: 11 and comprises a heavy chain having the amino acid sequence of SEQ ID NO: 12; or comprises a light chain having the amino acid sequence of SEQ ID NO: 13 and comprises a heavy chain having the amino acid sequence of SEQ ID NO: 14; or comprises a light chain having the amino acid sequence of SEQ ID NO: 15 and comprises a heavy chain having the amino acid sequence of SEQ ID NO: 16.

16. The antibody-drug conjugate of claim 1, wherein the antibody is an anti-human TROP2 antibody.

17. The antibody-drug conjugate of claim 16, wherein the anti-human TROP2 antibody comprises a light chain having the amino acid sequence of SEQ ID NO: 17 and comprises a heavy chain having the amino acid sequence of SEQ ID NO: 18; or comprises a light chain having the amino acid sequence of SEQ ID NO: 19 and comprises a heavy chain having the amino acid sequence of SEQ ID NO: 20.

18. The antibody-drug conjugate of claim 1, wherein the antibody is an anti-human CLDN18.2 antibody.

19. The antibody-drug conjugate of claim 18, wherein the anti-human CLDN18.2 antibody comprises a light chain having the amino acid sequence of SEQ ID NO: 21 and comprises a heavy chain having the amino acid sequence of SEQ ID NO: 22; or comprises a light chain having the amino acid sequence of SEQ ID NO: 23 and comprises a heavy chain having the amino acid sequence of SEQ ID NO: 24.

20. The antibody-drug conjugate of claim 1, wherein the antibody-drug conjugate has a drug to antibody ratio (DAR) of an integer or non-integer of 1 to 20.

21. The antibody-drug conjugate of claim 1, wherein the immune agonist is selected from the following:

i-1 (Resiquimod)

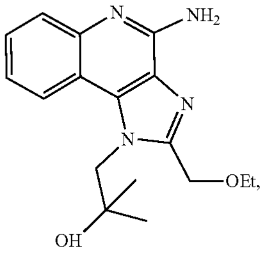

i-2

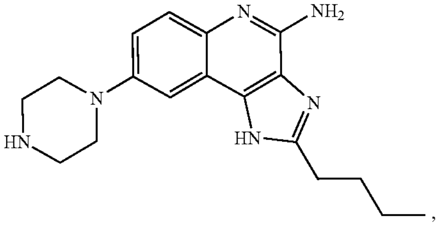

-continued i-3

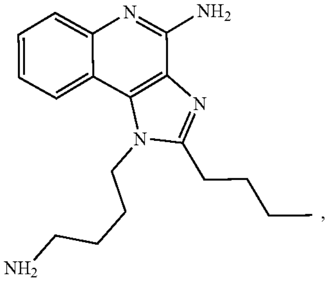

i-4

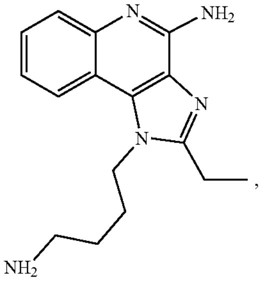

i-5

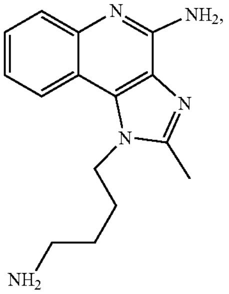

ii-1

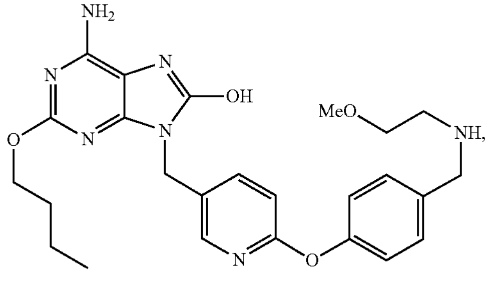

ii-2

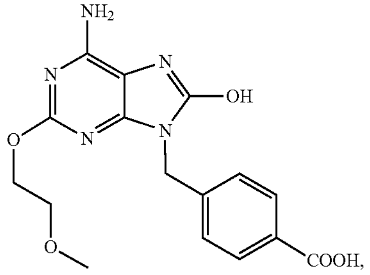

-continued
iii-1
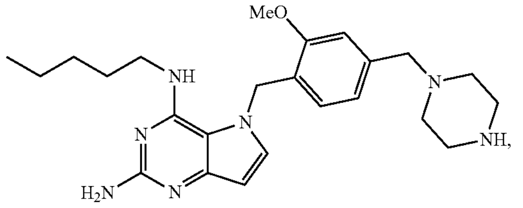
and
iv-1
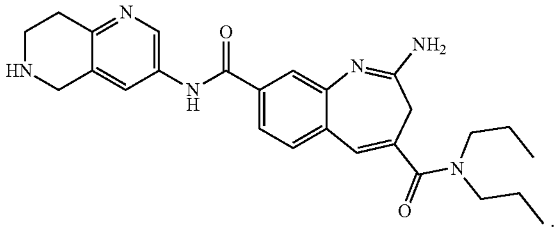
* * * * *